US011685738B2

(12) United States Patent
Askew et al.

(10) Patent No.: US 11,685,738 B2
(45) Date of Patent: *Jun. 27, 2023

(54) FLUORINATED TETRAHYDRONAPHTHYRIDINYL NONANOIC ACID DERIVATIVES AND USES THEREOF

(71) Applicant: OcuTerra Therapeutics, Inc., Boston, MA (US)

(72) Inventors: Ben C. Askew, Marshfield, MA (US); Takeru Furuya, Cambridge, MA (US)

(73) Assignee: OcuTerra Therapeutics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/076,891

(22) Filed: Oct. 22, 2020

(65) Prior Publication Data

US 2021/0277000 A1    Sep. 9, 2021

Related U.S. Application Data

(63) Continuation of application No. 16/373,780, filed on Apr. 3, 2019, now abandoned, which is a continuation of application No. 15/700,351, filed on Sep. 11, 2017, now Pat. No. 10,301,307, which is a continuation of application No. 15/047,717, filed on Feb. 19, 2016, now Pat. No. 9,790,222.

(60) Provisional application No. 62/118,303, filed on Feb. 19, 2015.

(51) Int. Cl.
  *C07D 471/04* (2006.01)
  *A61P 1/00* (2006.01)
  *A61P 27/00* (2006.01)

(52) U.S. Cl.
  CPC .............. *C07D 471/04* (2013.01); *A61P 1/00* (2018.01); *A61P 27/00* (2018.01)

(58) Field of Classification Search
  CPC .................................................. C07D 471/04
  See application file for complete search history.

(56) References Cited

U.S. PATENT DOCUMENTS

| | | | |
|---|---|---|---|
| 4,927,266 A | 5/1990 | Sugiura et al. | |
| 4,937,266 A | 6/1990 | Tomikawa et al. | |
| 5,374,660 A | 12/1994 | Murad et al. | |
| 5,501,969 A | 3/1996 | Hastings et al. | |
| 5,571,846 A | 11/1996 | Murad et al. | |
| 5,645,839 A | 7/1997 | Chobanian et al. | |
| 5,736,357 A | 4/1998 | Bromme et al. | |
| 6,017,926 A | 1/2000 | Askew et al. | |
| 6,066,648 A | 5/2000 | Duggan et al. | |
| 6,117,445 A | 9/2000 | Neely | |
| 6,139,847 A | 10/2000 | Chobanian et al. | |
| 6,211,184 B1 | 4/2001 | Duggan et al. | |
| 6,268,342 B1 | 7/2001 | Culler et al. | |
| 6,268,378 B1 | 7/2001 | Duggan et al. | |
| 6,291,503 B1 | 9/2001 | Schoop et al. | |
| 6,297,249 B1 | 10/2001 | Duggan et al. | |
| 6,303,126 B1 | 10/2001 | Nakamura et al. | |
| 6,407,241 B1 | 6/2002 | Jensen et al. | |
| 6,410,526 B1 | 6/2002 | Duggan et al. | |
| 6,426,353 B1 | 7/2002 | Arison et al. | |
| 6,472,403 B2 | 10/2002 | Duggan et al. | |
| 6,500,835 B2 | 12/2002 | Fukami et al. | |
| 6,664,227 B1 | 12/2003 | Wynn et al. | |
| 7,056,909 B2 | 6/2006 | Wang | |
| 8,901,144 B2 | 12/2014 | Askew et al. | |
| 9,266,884 B2 | 2/2016 | Askew et al. | |
| 9,518,053 B2 * | 12/2016 | Askew .................... | A61P 43/00 |
| 9,572,801 B2 | 2/2017 | Askew et al. | |
| 9,593,114 B2 | 3/2017 | Askew et al. | |
| 9,717,729 B2 * | 8/2017 | Askew ...................... | A61P 3/10 |
| 9,790,222 B2 * | 10/2017 | Askew .................... | A61P 27/00 |
| 9,802,933 B2 | 10/2017 | Askew et al. | |
| 10,106,537 B2 * | 10/2018 | Askew .................... | A61P 27/00 |
| 10,155,758 B2 | 12/2018 | Askew et al. | |
| 10,253,025 B2 * | 4/2019 | Furuya ................. | C07D 471/04 |
| 10,301,307 B2 * | 5/2019 | Askew ................ | C07D 471/04 |
| 10,752,625 B2 | 8/2020 | Furuya | |
| 2001/0053853 A1 | 12/2001 | Askew et al. | |
| 2002/0016461 A1 | 2/2002 | Albers et al. | |
| 2002/0037889 A1 | 3/2002 | Duggan et al. | |

(Continued)

FOREIGN PATENT DOCUMENTS

| CN | 1284955 A | 2/2001 |
|---|---|---|
| CN | 1589145 A | 3/2005 |

(Continued)

OTHER PUBLICATIONS

Registry No. 227963-76-0 (Entered STN Jul. 16, 1999) (Year: 1999).*
Abdollahi et al., "Inhibition of alpha(v)beta3 integrin survival signaling enhances antiangiogenic and antitumor effects of radiotherapy," Clin Cancer Res. Sep. 1, 2005;11(17):6270-9.
Adams J. et al., "Structure Activity Relationships of αv Integrin Antagonists for Pulmonary Fibrosis by Variation in Aryl Substituents", *ACS Medicinal Chemistry Letters*, vol. 5, No. 11, 2014, p. 1207-1212.
Ali, Y. et al., "Industrial perspective in ocular drug delivery," *Adv. Drug Deliv. Rev.* 2006, 58, 1258-1268.
Ando, M. et al., "Facile One-Pot Synthesis of N-Difluoromethyl-2-pyridone Derivatives", *Org. Lett.* 2006, 8(17), 3805-3808.

(Continued)

*Primary Examiner* — James D. Anderson
(74) *Attorney, Agent, or Firm* — Dechert LLP

(57) ABSTRACT

The present invention relates to fluorinated compounds of formula I and methods of synthesizing these compounds. The present invention also relates to pharmaceutical compositions containing the fluorinated compounds of the invention, and methods of treating fibrosis, macular degeneration, diabetic retinopathy (DR), macular edema, diabetic macular edema (DME), and macular edema following retinal vein occlusion (RVO), by administering these compounds and pharmaceutical compositions to subjects in need thereof.

20 Claims, 2 Drawing Sheets

(56) References Cited

U.S. PATENT DOCUMENTS

| | | |
|---|---|---|
| 2002/0040030 A1 | 4/2002 | Coleman et al. |
| 2002/0040039 A1 | 4/2002 | Hartman et al. |
| 2002/0049224 A1 | 4/2002 | Arison et al. |
| 2004/0038963 A1 | 2/2004 | Wang |
| 2004/0053968 A1 | 3/2004 | Hartman et al. |
| 2004/0249158 A1 | 12/2004 | Wells et al. |
| 2005/0004199 A1 | 1/2005 | Hartman et al. |
| 2005/0043344 A1 | 2/2005 | Boys et al. |
| 2006/0030581 A1 | 2/2006 | DeBusi et al. |
| 2007/0117849 A1 | 5/2007 | Goodman et al. |
| 2013/0129621 A1 | 5/2013 | Mackel et al. |
| 2016/0075698 A1 | 3/2016 | Askew et al. |
| 2016/0130270 A1 | 5/2016 | Askew et al. |
| 2017/0096427 A1 | 4/2017 | Askew et al. |
| 2017/0291900 A1 | 10/2017 | Askew et al. |
| 2018/0016276 A1 | 1/2018 | Askew et al. |
| 2019/0225609 A1 | 7/2019 | Askew et al. |
| 2019/0263810 A1 | 8/2019 | Askew et al. |
| 2021/0163473 A1 | 6/2021 | Askew et al. |
| 2021/0246132 A1 | 8/2021 | Askew et al. |

FOREIGN PATENT DOCUMENTS

| | | |
|---|---|---|
| EP | 1040098 A1 | 10/2000 |
| WO | WO-199613523 A1 | 5/1996 |
| WO | WO-199930709 A1 | 6/1999 |
| WO | WO-199931061 A1 | 6/1999 |
| WO | WO-199931099 A1 | 6/1999 |
| WO | WO-200147867 A1 | 7/2001 |
| WO | WO-200187840 A1 | 11/2001 |
| WO | WO-200207730 A1 | 1/2002 |
| WO | WO-2004058254 A1 | 7/2004 |
| WO | WO-2011060395 A1 | 5/2011 |
| WO | WO-2011150156 A2 | 12/2011 |
| WO | WO-2013000909 A1 | 1/2013 |
| WO | WO-2014124302 A1 | 8/2014 |

OTHER PUBLICATIONS

Bourges et al., "Ocular drug delivery targeting the retina and retinal pigment epithelium using polylactide nanoparticles," Invest Ophthalmol Vis Sci. Aug. 2003;44(8):3562-9.

Bradshaw et al., "Synthesis of 5-hydroxy-2,3,4,5-tetrahydro-[1H]-2-benzazepin-4-ones: selective antagonists of muscarinic (M3) receptors," Org Biomol Chem. Jun. 21, 2008;6(12):2138-57.

Brinkmann et al., "Fingolimod (FTY720): discovery and development of an oral drug to treat multiple sclerosis," NATURE Reviews, Drug Discovery, 9:883-897 (2010).

Bunz, "The Cancer Gene Theory," Principles of Cancer Genetics, 1:1-47 (2008).

Campochiaro, P.A., et al., "Reduction of Diabetic Macular Edema by Oral Administration of the Kinase Inhibitor PKC412," Invest. Ophthalmol. Vis. Sci., 45:922-931 (2004).

Cao, F., et al. "Zn—Al—NO3-layered double hydroxides with intercalated diclofenac for ocular delivery," International Journal of Pharmaceuticals, 404:250-256 (2011).

Chavakis, E. et al., "Kinetics of integrin expression in the mouse model of proliferative retinopathy and success of secondary intervention with cyclic RGD peptides", Diabetologla 2002, 45, 262-267.

Chen, H. et al., "FICA and BSEP defects in Taiwanese patients with chronic intrahepatic cholestasis with low y-glutamyltranspeptidase levels", J. Ped. 2002, 140, 119-124.

Chu et al., "Interaction of West Nile Virus with avb3 Integrin Mediates Virus Entry into Cells", The Journal of Biological Chemistry, vol. 279, No. 52, p. 54533-54541 (2004).

Coleman, P. et al., Nonpeptide avB3 Antagonists. Part II: Discovery and Preclinical Evaluation of Potent avB3 Antagonists for the Prevention and Treatment of Osteoporosis, J. Med Chem. 2004, 47, 4829-4837.

Coughlin et al., "Approaches and limitations of phosphatidylinositol-3-kinase pathway activation status as a predictive biomarker in the clinical development of targeted therapy", Breast Cancer Research Treatment, 1-11 (201 0).

D'Ambrosio et al., "Chemokine receptors in inflammation: an overview," Journal of Immunological Methods, 273:3-13 (2003).

Data from the National Cancer Institute (http://www.cancer.gov/) (Downloaded May 29, 2014).

Diebold, Y. et al., "Applications of nanoparticles in ophthalmology," Progress in Retinal and Eye Research, 29:596-609 (2010).

Dorrell, M., "Combination angiostatic therapy completely inhibits ocular and tumor angiogenesis," Proceedings of the National Academy of Sciences of the United States of America, 104(3):967-972 (2007).

Doukas, J., et al., "Topical Administration of a Multi-Targeted Kinase Inhibitor Suppresses Choroidal Neovascularization and Retinal Edema," Journal of Cellular Physiology, 216:29-37 (2008).

Duan et al., "Association of αvl33 integrin expression with the metastatic potential and migratory and chemotactic ability of human osteosarcoma cells," Clinical & Experimental Metastasis, 21:747-753 (2004).

Felding-Habermann, "Involvement of tumor cell integrin αvl33 in hematogenous metastasis of human melanoma cells," Clinical & Experimental Metastasis, 19:427-436 (2002).

Freund, K. et al., "Age-related Macular Degeneration and Choroidal Neovascularization" Am. J. Ophthalmol. 1993, 115(6), 786-791.

Friedlander, M. et al., "Involvement of integrins avB3 and avB5 in ocular neovascular diseases", Proc. Natl. Acad. Sci USA 1996, 93, 9764-9769.

Friedlander, P., Ber. Dtsch. Chern. Ges. 1882, 15, 2572.

Fu, Y., et al., "Angiogenesis Inhibition and Choroidal Neovascularization Suppression by Sustained Delivery of an Integrin Antagonist, EMD478761," Invest. Ophthalmol. Vis. Sci., 48(11):5184-5190 (2007).

Gaudana, R. et al., "Recent Perspectives in Ocular Drug Delivery", Pharm. Res.. 2009, 26(5), 1197-1216.

Hahm, K. et al., "avB6 Integrin Regulates Renal Fibrosis and Inflammation in Alport House", Am. J. Pathol. 2007, 170(1), 110-125.

Hallinan, E.A. et al., "N-Substituted dibenzoxazepine as analgesic PGE2 antagonists," J. Med. Chem., 36:3293-3299 (1993).

Hariharan et al., "Assessment of the biological and pharmacological effects of the αvl35 and αvl35 integrin receptor antagonist, cilengitide (EMD 121974), in patients with advanced solid tumors," Annals of Oncology, 18:1400-1407 (2006).

Haynes et al., Bone Resorption in, Wiley Encyclopedia of Biomedical Engineering (M. Akay ed., 2006).

Henderson, N. et al., "Targeting of av integrin identifies a core molecular pathway that regulates fibrosis in several organs", Nat. Med. 2013, 19(12), 1617-1627.

Hodlvala-Dilke, "av63 integrin and angiogenesis: a moody integrin in a changing Environment", Current Opinion in Cell Biology, 20:514-519 (2008).

Hutchison, John H., et al., Nonpeptide $\alpha v \beta 3$ Antagonists. 8. In Vitro and In Vivo Evaluation of a Potent $\alpha v \beta 3$ Antagonist for the Prevention and Treatment of Osteoporosis, J. Med. Chem., 46:4790-4798 (2003).

Hynes, "lIntegrins: bidirectional, allosteric signaling machines," Cell. Sep. 20, 2002;110(6):673-87.

Jacot, J.L. et al., "Potential Therapeutic Roles for Inhibition of the P13K/Akt/mTOR Pathway in the Pathophysiology of Diabetic Retinopathy," Journal of Ophthalmology, vol. 2011, Article ID 589813 (2011).

Jubb et al., "Predicting benefit from antiangiogenic agents in malignancy", Nature Reviews/Cancer, 6: 626-635 (2006).

Judge et al., "Potassium channel blockers in multiple sclerosis: Neuronal Kv channels and effects of symptomatic treatment," Pharmacology & Therapeutics, 111 :224-259 (2006).

Kamizuru, H. et al., "Monoclonal Antibody-Mediated Drug Targeting to Choroidal Neovascularization in the Rat", Invest. Ophthal. Vis. Sci. 2001, 42(11), 2664-2672.

Kaur, H. et al., "Niosomes: A Novel Drug Delivery System", Int. J. Pharm. Sci. Rev. Res. 2012, 15(1), 113-120.

(56) References Cited

OTHER PUBLICATIONS

Kern, T.S., et al., "Topical administration of nepafenac inhibits diabetes-induced retinal microvascular disease and underlying abnormalities of retinal metabolism and physiology," *Diabetes*, 56(2):373-379 (2007).
Klein, M. et al., "Heredity and Age-Related Macular Degeneration, Observations in Monozygotic Twins" *Arch. Ophthalmol.* 1994, 112(7), 932-937.
Klein, R. et al., "The Wisconsin Epidemiologic Study of diabetic retinopathy. XIV. Ten-year incidence and progression of diabetic retinopathy," *Arch Ophthalmol*, 12:1217-1228 (1994).
Koelink et al., "Targeting chemokine receptors in chronic inflammatory diseases: An extensive review," *Pharmacology & Therapeutics*, 133 :1-18 (2012).
Kumar, C. et al., "Biochemical Characterization of the Binding of Echistatin to Integrin avB3 Receptor", *J. Pharmacol. Exp. Ther.* 1997, 283(2), 843-853.
Kuppen et al., "Tumor structure and extracellular matrix as a possible barrier for therapeutic approaches using immune cells or adenoviruses in colorectal cancer," *Histochemistry and Cell Biology*, 115: 67-72 (2001).
Linderman, R.J., "Oxidation of Fluoroalkyl-Substituted Carbinols by the Dess-Martin Reagent," *J. Org. Chem.*, 54(3):661-668 (1989).
Lissoni et al., "Biotherapy with the pineal hormone melatonin plus aloe and myrrh tincture in untreatable metastatic cancer patients as an essence therapy of cancer," *Cancer Research*, 7:397-401 (2009).
Lorger et al., Activation of tumor cell integrin $\alpha v \beta 3$ controls angiogenesis and metastatic growth in the brain, *PNAS*, 106:10666-10671 (2009).
Luna, J. et al., "Antagonists of Integrin avB3 Inhibit Retinal Neovascularization in a Murine Model", *Lab. Invest.* 1996, 75(4), 563-573.
Luo et al., "Principles of Cancer Therapy: Oncogene and Non-oncogene Addiction," *Cell*, 136: 823-837 (2009).
Lyons et al., "Integrins in metastatic adenoid cystic carcinoma," *International Journal of Oral and Maxillofacial Surgery*, 34 :912-914 (2005).
Marelli et al., "Tumor targeting via integrin ligands," *Frontiers in Oncology*, 3:1-12 (2013).
Max et al., "Immunohistochemical analysis of integrin $\alpha v \beta 3$ expression on tumor-associated vessels of human carcinomas," *International Journal of Cancer*, 71:320-324 (1997).
McDermott et al., "Personalized Cancer Therapy With Selective Kinase Inhibitors: An Emerging Paradigm in Medical Oncology", *Journal of Clinical Oncology*, 27:5650-5659 (2009).
Meissner, R.S. et al., "Nonpeptide $\alpha v \beta 3$ Antagonists. Part 2: Constrained Glycyl Amides Derived from the RGD Tripeptide", *Bioorganic & Medicinal Chemistry Letters*, 12:25-29 (2002).
Millauer, B., et al., "Dominant-Negative Inhibition of Flk-1 Suppresses the Growth of Many Tumor Types in Vivo", *Cancer Research*, 56:1615-1620 (1996).
Moors et al. Journal of Medicinal Chemistry (2011), 54(17), 6098-6105.
Mousa, "Cell Adhesion Molecules: Potential Therapeutic & Diagnostic Implications," *Molecular Biotechnology*, 38:33-40 (2008).
Muller et al., Antiviral Strategies in, Antiviral Strategies 1-24, 4 (H.-G. Krausslich et al., eds., 2009).
Murphy, M.G., et al., "Effect of L-000845704, an $\alpha v \beta 3$ Integrin Antagonist, on Markers of Bone Turnover and Bone Mineral Density in Postmenopausal Osteoporotic Women," *The Journal of Clinical Endocrinology & Metabolism*, 90(4):2022-2028 (2005).
Nahm, S., et al., "N-methoxy-n-methyl amides as effective acylating agents," *Tetrahedron Letters*, 22(39):3815-3818 (1981).
Noutsias M. et al. "Human Coxsackie-Adenovirus Receptor is Colocalized with ayb3 and avb5 on the Cardiomyocyte Sarcolemma and Upregulated in Dilated Cardiomyopathy Implications for Cardiotropic Viral Infections", *Circulation*, vol. 104, p. 275-280 (2001).
Parry C. et al. "Herpes simplex virus type 1 glycoprotein H binds to aVB3 integrins", *Journal of General Virology*, vol. 86, p. 7-10 (2005).
Pialat, A. et al., "Oxidative para-Triflation of Acetanilides," *Organic Letters*, 15:1764-1767 (2013).
Poynard, T. et al., "Natural history of liver fibrosis progression in patients with chronic hepatitis C", *The Lancet* 1997, 349, 825-832.
Prasasya et al., "Analysis of cancer signaling networks by systems biology to develop therapies", *Seminars in Cancer Biology*, 21: 200-206 (2011).
Rabinow, Barrett E., "Nanosuspensions in Drug delivery," *Nature Reviews Drug Discovery*, 3:785-796 (2004).
Reinmuth et al., "av133 Integrin Antagonist S247 Decreases Colon Cancer Metastasis and Angiogenesis and Improves Survival in Mice", Cancer Research, 63:2079-2087 (2003).
Riecke, B. et al. "Topical Application of Integrin Antagonists Inhibit Proliferative Retinopathy," *Horm Metab Res*, 33:307-311 (2001).
Rognoni, E. et al., "Kindlin-1 controls Wnt and TGF-B availability to regulate cutaneous epithelial stem cell proliferation", *Nat. Med.* 2014, 20(4), 350-359.
Rolli et al., "Activated integrin $\alpha v \beta 3$ cooperates with metalloproteinase MMP-9 in regulating migration of metastatic breast cancer cells", *PNAS*, 100:9482-9487 (2003).
Rowe, Raymond C., "Handbook of Pharmaceutical Excipients", Fifth Edition, Pharmaceutical Press and American Pharmacists Association (2006).
Santulli et al., "Evaluation of the anti-angiogenic properties of the new selective av[33 integrin antagonist RGDechiHCit", Journal of Translational Medicine, 9:1-10 (2011.
Santulli, R. et al., "Studies with an Orally Bioavailable ?v Integrin Antagonist in Animal Models of Ocular Vasculopathy: Retinal Neovascularization in Mice and Retinal Vascular Permeability in Diabetic Rats," The Journal of Pharmacology and Experimental Therapeutics, 324:894-90 (2008).
Sato, I. et al., "Enantioselective Synthesis of Substituted 3-Quinolyl Alkanols and Their Application to Asymmetric Autocatalysis," *Synthesis*, 9:1419-1428 (2004).
Sawyers, "The Cancer Biomarker Problem", *Nature*, 548-552 (2008).
Seebach, D. et al., "Total Synthesis of Myxovirescin, 1 Strategy and Construction of the Southeastern Part [O(1)-C(14)]", Liebigs Ann. Chem., pp. 701-717 (1994).
Sondej, S.C. et al., "Gem-Difluoro Compounds: A Convenient Preparation from Ketones and Aldehydes by Halogen Fluoride Treatment of 1,3-dithiolanes," J. Org. Chem., 51:3508-3513 (1986).
Soussi, "p53 Antibodies in the Sera of Patients with Various Types of Cancer: A Review," *Cancer Research*, 60:1777-1788 (2000).
Speicher, M.A. et al. "Pharmacologic therapy for diabetic retinopathy," Expert Opin Emerging Drugs, 8(1):239-250 (2003).
Stragies, R. et al. "Design and Synthesis of a New Class of Selective Integrin $=5\beta1$ antagonists", J. Med. Chem., 50:3786-3794 (2007).
Stupp et al., "Integrin Inhibitors Reaching the Clinic", *Journal of Clinical Oncology*, 25 :1637-1638 (2007).
Summerford C. et al. "avB5 integrin: a co-receptor for adeno-associated virus type 2 infection", Nature Medicine, vol. 5, No. 1, p. 78-82 (1999).
Surendranan, K. et al., "A role for Wnt-4 in renal fibrosis", *Am. J. Physiol. Renal Physiol.* 2002, 46, 270-278.
Sutherland et al., "Management of Chronic Obstructive Pulmonary Disease," *The New England Journal of Medicine*, 350:2689-2697 (2004).
Takagi, H. et al., "Role of Vitronectin Receptor-Type Integrins and Osteopontin in Ischemia-Induced Retinal Neovascularization," *Japanese ODthalmological Society*, 46:270-278 (2002).
Takahashi, K et al. "Suppression and Regression of Choroidal Neovascularization by the Multitargeted Kinase Inhibitor Pazopanib," *Arch. Ophthalmol.*, 127(4): 494-499 (2009).
Takayama et al., "The Relationship Between Bone Metastasis from Human Breast Cancer and Integrin $\alpha v 133$ Expression," *Anticancer Research*, 25 :79-84 (2005).
Vandamme, Th.F., "Microemulsions as ocular drug delivery systems: recent developments and future challenges," *Progress in Retinal and Eye Research*, 21:15-34 (2002).

(56) References Cited

OTHER PUBLICATIONS

Wagh, V.D. et al. "Niosomes as ophthalmic drug delivery systems: a review," *Journal of Pharmacy Research*, 3(7):1558-1563 (2010).

Wang et al., "Mathematical modeling in cancer drug discovery," *Drug Discovery Today*, 19:145-150 (2014).

Wang, W. et al. "The Antiangiogenic Effects of Integrin =5β1 Inhibitor (ATN-161) In Vitro and In Vivo," *Invest. Ophthalmol. Vis. Sci.*, 52(10):7213-7220 (2011), Published online before print Aug. 3, 2011.

Ward et al., "Inflammation and ?v133 Integrin," American Journal of Respiratory and Critical Care Medicine, 85:5-6 (2012).

Wayner, E. et al., "Integrins avB5 and avB6 Contribute to Cell Attachment to Vitronectin but Differentially Distribute on the Cell Surface", J. Cell. Biol. 1991, 113(4), 919-929.

Wilder R. et al. "Integrin alpha V beta 3 as a target for treatment of rheumatoid arthritis and related rheumatic diseases", Ann Rheum Dis, vol. 61, Suppl. II, p. 96-99 (2002).

Williams, R. et al. "Epidemiology of diabetic retinopathy and madular oedema: a review," *Eye*, 18:963-983 (2004).

Yang, X.M., "Role of P13K/Akt and MEK/ERK in Mediating Hypoxia-Induced Expression of HIF-1? and VEGF in Laser-Induced Rat Choroidal Neovascularization," Investigative Ophthalmology & Visual Science, 50(4):1873-1879 (2009).

Yanni, S.E. et al., "The effects of nepafenac and amfenac on retinal angiogenesis," Elsevier, Brain Research Bulletin, 81:310-319 (2010).

Yasuda, N., et al., "An Efficient Synthesis of an αvβ3 Antagonist," *J. Org. Chem.*, 69:1959-1966 (2004).

Yasukawa, T, et al. "Inhibition of experimental choroidal neovascularization in rats by an αv-integrin antagonist," Current Eye Research, 28(5):359-366 (2004).

Zarbin, M.A. "Current Concepts in the Pathogenesis of Age-Related Macular Degeneration", Arch. Ophthalmol., 122:598-614 (2004).

Zhao et al., Journal of Physical Chemistry B (2009), 113(17). 5929-5937.

Zhou, Hong-Yan et al., "Nanoparticles in the ocular drug delivery," *Int. J. Ophthalmol*, 6(3):390-396 (2013).

\* cited by examiner

FLUORINATED TETRAHYDRONAPHTHYRIDINYL NONANOIC ACID DERIVATIVES AND USES THEREOF

RELATED APPLICATION

This application is a continuation of U.S. application Ser. No. 16/373,780, filed Apr. 3, 2019, which is a continuation of U.S. application Ser. No. 15/700,351, filed Sep. 11, 2017 (now U.S. Pat. No. 10,301,307), which is a continuation of U.S. application Ser. No. 15/047,717, filed Feb. 19, 2016 (now U.S. Pat. No. 9,790,222), which claims the benefit of and priority to U.S. provisional application No. 62/118,303, filed Feb. 19, 2015, the entire contents of each of which are incorporated herein by reference in their entireties.

BACKGROUND OF THE INVENTION

Fibrosis is characterized by excessive accumulation of collagen in the extracellular matrix of the involved tissue. It is a long-standing and challenging clinical problem for which no effective treatment is currently available. The production of collagen is a highly regulated physiological process, the disturbance of which may lead to the development of tissue fibrosis. The formation of fibrous tissue is part of the normal beneficial process of healing after injury. In some cases, however, an abnormal accumulation of fibrous material can severely interfere with the normal function of the affected tissue or even cause the complete loss of function of the affected organ.

A variety of compounds have been identified as anti-fibrosis agents via different mechanisms of action, including the suppression of collagen expression. For example, pantethine (D-bis-(N-pantothenyl-β-aminoethyl)-disulfide) has been reported to be effective for the inhibition of hepatic fibrosis (U.S. Pat. No. 4,937,266). Also, a hydrazine derivative, benzoic hydrazide, has been shown to be a powerful antifibrotic agent (U.S. Pat. Nos. 5,374,660 and 5,571,846). In addition, angiotensin inhibitors are used in combination with nitric oxide stimulators to inhibit the progression of fibrosis (U.S. Pat. Nos. 5,645,839 and 6,139,847). Further, $A_1$ adenosine receptor antagonists and/or $P_{2x}$ purinoceptor antagonists are described for treating or preventing fibrosis and sclerosis (U.S. Pat. No. 6,117,445). More recently, somatostatin agonists, hepatocyte growth factors (HGFs), chymase inhibitors, and antagonists of IL-13 have been reported to effectively inhibit fibrosis (U.S. Pat. Nos. 6,268,342, 6,303,126, 6,500,835, and 6,664,227).

Age-related macular degeneration (AMD) is the leading cause of blindness in people over 55; and diabetic retinopathy (DR) is the leading cause in people under 55 (Klein, 1994; Williams, 2004). Both diseases are characterized by new blood vessel growth (Freund, 1993; Speicher, 2003; Zarbin, 2004). Macular edema and Diabetic macular edema (DME) occur when fluid and protein deposits collect on or under the macula caused by leaking macular capillaries. Thrombosis of central retinal vein (CRV) and its branches is the second most prevalent vascular pathology after DR, and results in abrupt decrease in visual acuity and is accompanied by macular edema. Thus, anti-angiogenesis treatments are useful in combating all these conditions.

Integrins are heterodimeric transmembrane proteins through which cells attach and communicate with extracellular matrices and other cells. αv integrins are key receptors involved in mediating cell migration and angiogenesis. αv integrins have been shown to be involved in a number of diseases and conditions including ocular angiogenesis and fibrosis of organs. Expression of αv integrins is upregulated in various diseases or conditions, such as AMD and DR, and in mouse model of oxygen-induced retinopathy (OIR) or retinopathy of prematurity (ROP) model (Takagi, 2002). Also, αvβ3 is expressed in new vessels after photocoagulation, but not in normal choroidal vessels, in the laser-induced choroidal neovascularization model for AMD (Kamizuru, 2001). Administration of αv integrins antagonists, such as a cyclic RGD peptide, has been shown to inhibit retinal and choroidal neovascularization (Friedlander, 1996; Chavakis, 2002; Luna, 1996; Riecke, 2001; Yasukawa, 2004). Angiogenesis inhibitors targeting vascular endothelial growth factor (VEGF), other growth factors (e.g., fibroblast growth factor (FGF), platelet-derived growth factor (PDGF)), chemokines (e.g., IL8, SDF1, G-CSF), receptors (e.g., CXCR1, FGF-R, PlGFR, PDGFR, Tie-receptors), intracellular mediators (e.g., c-kit kinase, PI3 kinase, PKC), and extracellular mediators (e.g., integrins, cadherins), as well as inhibitors of pro-angiogenic targets (e.g., phosphoinositide 3 kinase), have been investigated for the treatment of AMD and DR. However, application of these drugs is limited.

Thus, there continues to be a need for compounds, compositions, and methods for treating fibrosis, AMD, DR, DME, and macular edema following retinal vein occlusion, that are safe, effective, and conveniently administered. The present invention addresses the need.

SUMMARY OF THE INVENTION

The present invention provides a compound of formula I:

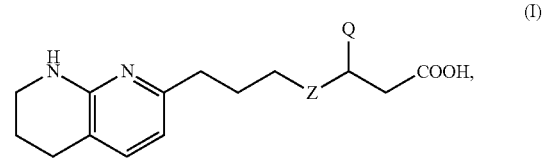

(I)

or a pharmaceutically acceptable salt or solvate thereof, wherein the compound of formula I is defined in detail herein below.

The present invention also provides a pharmaceutical composition comprising a compound of formula I or a pharmaceutically acceptable salt or solvate thereof, and a pharmaceutically acceptable carrier or excipient.

The present invention also provides a method of treating or preventing a fibrosis, comprising administering to a subject in need thereof a therapeutically effective amount of a compound of formula Ia:

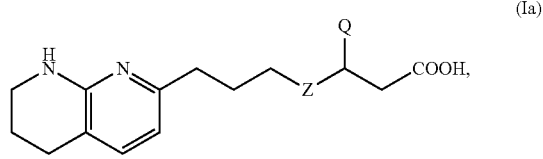

(Ia)

or a pharmaceutically acceptable salt or solvate thereof or a therapeutically effective amount of a pharmaceutical composition of the invention, wherein the compound of formula Ia is defined in detail herein below. In one aspect, the invention provides treating a fibrosis. In one aspect, the invention provides preventing a fibrosis.

The present invention also provides the use of a compound of formula Ia or a pharmaceutically acceptable salt or solvate thereof in the manufacture of a medicament for the treatment or prevention of a fibrosis in a subject. The present invention also provides the use of a compound of formula Ia or a pharmaceutically acceptable salt or solvate thereof in treating or preventing a fibrosis in a subject.

The present invention also provides a method of treating or preventing a disease or condition in a subject, comprising administering to a subject in need thereof a therapeutically effective amount of a compound of formula I or a pharmaceutically acceptable salt or solvate thereof or a therapeutically effective amount of a pharmaceutical composition comprising a compound of formula I or a pharmaceutically acceptable salt or solvate thereof. In one aspect, the invention provides treating a disease or condition. In one aspect, the invention provides preventing a disease or condition.

The present invention provides a method of treating or preventing a disease or condition mediated by an αv integrin in a subject, comprising administering to a subject in need thereof a therapeutically effective amount of a compound of formula I or a pharmaceutically acceptable salt or solvate thereof or a therapeutically effective amount of a pharmaceutical composition comprising a compound of formula I or a pharmaceutically acceptable salt or solvate thereof. In one aspect, the disease or condition is a disease or condition in which angiogenesis is involved. In a further aspect, the disease or condition is a disease or condition in which ocular angiogenesis is involved.

The present invention also provides a method of treating or preventing an αvβ3, αvβ5, αvβ6 and/or αvβ8 integrin-mediated disease or condition in a subject, comprising administering to a subject in need thereof a therapeutically effective amount of a compound of formula I or a pharmaceutically acceptable salt or solvate thereof or a therapeutically effective amount of a pharmaceutical composition comprising a compound of formula I or a pharmaceutically acceptable salt or solvate thereof. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO). In one aspect, the condition is fibrosis of the liver, kidney, intestine, lung, and heart. In one aspect, the disease is a renal disease, a respiratory disease, a gastrointestinal disease, a cardiovascular disease, a bone and articular disease, a skin disease, an obstetric disease, or a urologic disease.

The present invention provides the use of a compound of formula I or a pharmaceutically acceptable salt or solvate thereof in the manufacture of a medicament for the treatment or prevention of a disease or condition in a subject. The present invention provides the use of a compound of formula I or a pharmaceutically acceptable salt or solvate thereof in treating or preventing a disease or condition in a subject.

The present invention provides the use of a compound of formula I or a pharmaceutically acceptable salt or solvate thereof in the manufacture of a medicament for the treatment or prevention of a disease or condition mediated by an αv integrin in a subject. The present invention provides the use of a compound of formula I or a pharmaceutically acceptable salt or solvate thereof in treating or preventing a disease or condition mediated by an αv integrin in a subject. In one aspect, the disease or condition is a disease or condition in which angiogenesis is involved. In a further aspect, the disease or condition is a disease or condition in which ocular angiogenesis is involved.

The present invention also provides the use of a compound of formula I or a pharmaceutically acceptable salt or solvate thereof in the manufacture of a medicament for the treatment or prevention of an αvβ3, αvβ5, αvβ6 and/or αvβ8 integrin-mediated disease or condition in a subject. The present invention provides the use of a compound of formula I or a pharmaceutically acceptable salt or solvate thereof in treating or preventing of an αvβ3, αvβ5, αvβ6 and/or αvβ8 integrin-mediated disease or condition in a subject. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO). In one aspect, the condition is fibrosis of the liver, kidney, intestine, lung, and heart. In one aspect, the disease is a renal disease, a respiratory disease, a gastrointestinal disease, a cardiovascular disease, a bone and articular disease, a skin disease, an obstetric disease, or a urologic disease.

Unless otherwise defined, all technical and scientific terms used herein have the same meaning as commonly understood by one of ordinary skill in the art to which this invention belongs. In the case of conflict, the present specification, including definitions, will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In addition, the materials, methods, and examples are illustrative only and are not intended to be limiting.

Other features and advantages of the invention will be apparent from the following detailed description and claims.

DETAILED DESCRIPTION OF THE INVENTION

Compounds of the Invention

Figure 1:
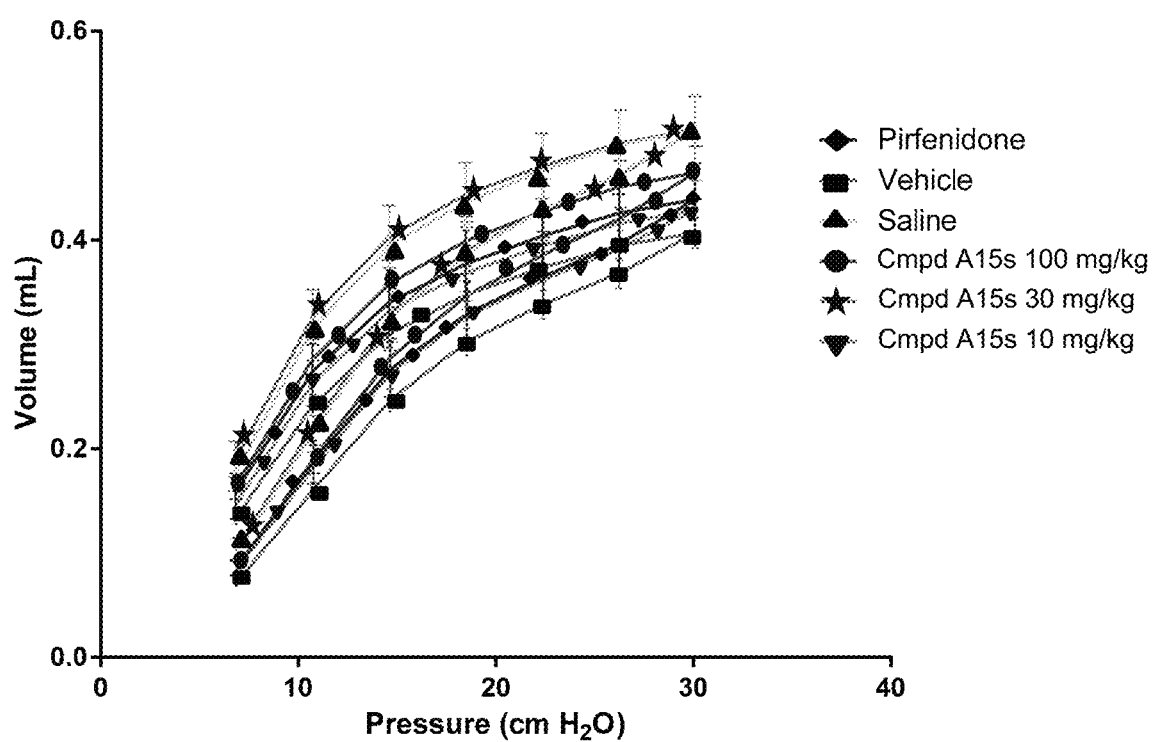
FIG. 1 shows lung stiffness as measured by the pressure volume curves in mice when dosed with 10 mg/kg, 30 mg/kg, and 100 mg/kg of Compound A15s, pirfenidone, saline, or vehicle.
Figure 2:
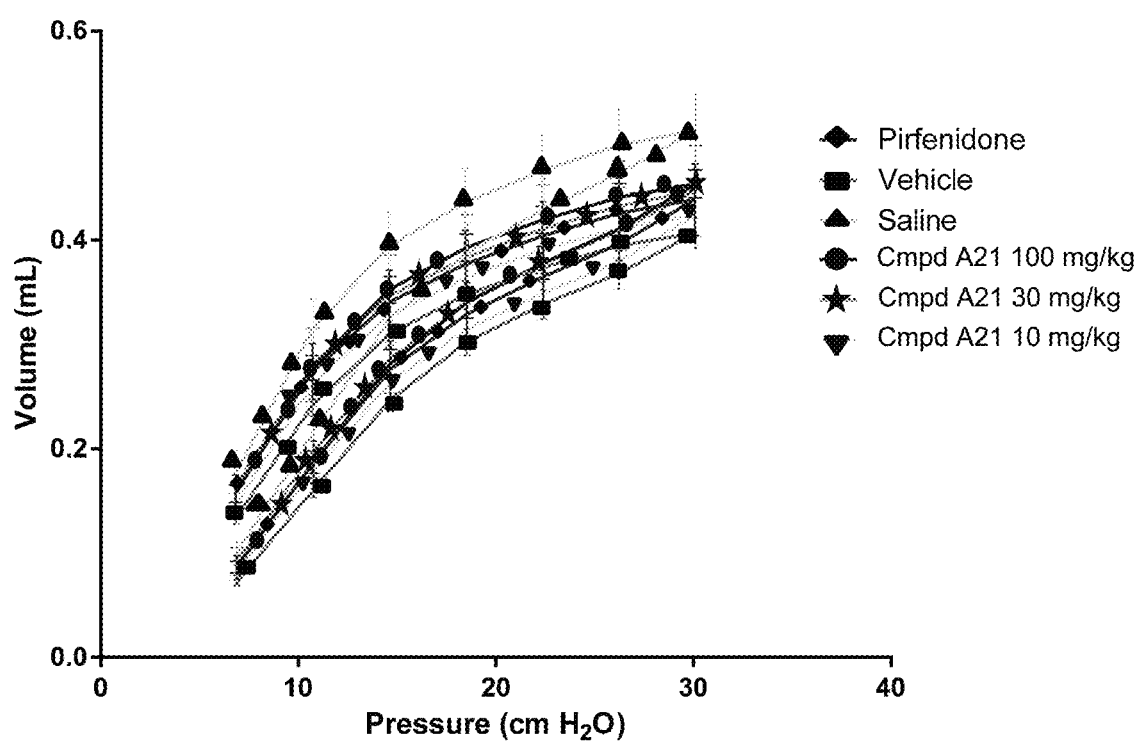
FIG. 2 shows lung stiffness as measured by the pressure volume curves in mice when dosed with 10 mg/kg, 30 mg/kg, and 100 mg/kg of Compound A21, pirfenidone, saline, or vehicle.

The present invention relates to novel fluorinated compounds of formula I:

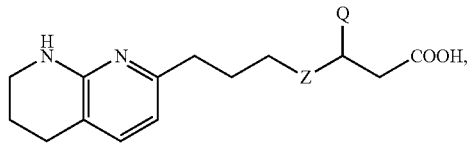
(I)

or a pharmaceutically acceptable salt or solvate thereof, wherein:

Z is

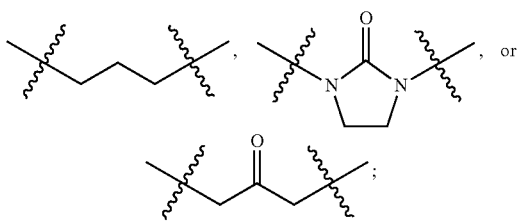, or

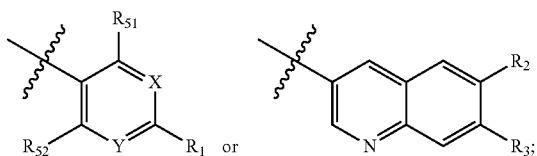;

Q is

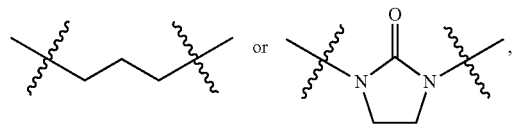 [SMILES: *CCC* ; *N1CCN(*)C1=O]

X is $CR_4$ or N;
Y is $CR_4$ or N;
$R_1$ is H, F, Cl, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms;
$R_2$ and $R_3$ are each independently H, F, $CH_2F$, $CHF_2$, or $CF_3$, provided that one of $R_2$ and $R_3$ is not H;
each $R_4$ is independently H, $CH_2F$, $CHF_2$, or $CF_3$; and
$R_{51}$ and $R_{52}$ are each independently H, F, or Cl;
provided that the compound of formula I contains at least one fluorine atom, and provided that when Z is

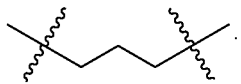 [SMILES: *CCC*] or 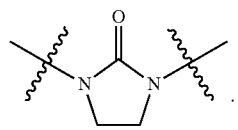 [SMILES: *N1CCN(*)C1=O], $R_1$ is not H, F, or Cl, and $R_{51}$ and $R_{52}$ are each H, then at least one of X and Y is $CR_4$, and $R_4$ is $CH_2F$, $CHF_2$, or $CF_3$.

The compounds of the present invention contain at least one fluorine atom. In one aspect, the compounds of the present invention contain at least one fluorine atom in the $R_1$ substituent. In another aspect, the compounds of the present invention contain at least one fluorine atom in the $R_2$ or $R_3$ substituent. In another aspect, the compounds of the present invention contain at least one fluorine atom in the $R_4$ substituent.

In one aspect, Z is

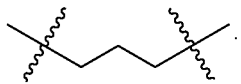 [SMILES: *CCC*]

In another aspect, Z is

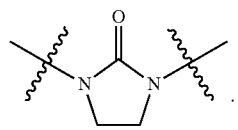 [SMILES: *N1CCN(*)C1=O].

In another aspect, Z is

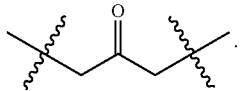 [SMILES: *CC(=O)C*]

In one aspect, Q is

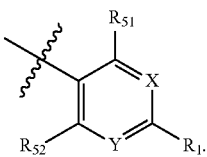.

In one aspect, X is N and Y is $CR_4$. In another aspect, X and Y are each $CR_4$. In another aspect, X and Y are each N.

In one aspect, at least one $R_4$ is H. In one aspect, at least one $R_4$ is $CH_2F$, $CHF_2$, or $CF_3$. In a further aspect, at least one $R_4$ is $CF_3$.

In one aspect, $R_1$ is H. In another aspect, $R_1$ is F, Cl, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is F or Cl. In another aspect, $R_1$ is $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms.

In a further aspect, $R_1$ is straight chain $C_1$-$C_4$ or branched $C_3$-$C_4$ alkyl, and is substituted with 1, 2, 3, 4, 5, 6, 7, 8, or 9 fluorine atoms. In a further aspect, $R_1$ is methyl, ethyl, propyl, or butyl, and is substituted with 1, 2, 3, 4, 5, 6, 7, 8, or 9 fluorine atoms. In a further aspect, $R_1$ is methyl substituted with 1, 2, or 3 fluorine atoms. In a further aspect, $R_1$ is $CF_3$.

In another further aspect, $R_1$ is straight chain $C_1$-$C_6$ or branched $C_3$-$C_6$ alkoxy, and is substituted with 0, 1, 2, 3, 4, 5, 6, or 7 fluorine atoms. In a further aspect, $R_1$ is methoxy, ethoxy, propoxy, or butoxy, and is substituted with 0, 1, 2, 3, 4, 5, 6, or 7 fluorine atoms. In a further aspect, $R_1$ is methoxy substituted with 0, 1, 2, or 3 fluorine atoms. In a further aspect, $R_1$ is $OCH_3$, $OCH_2F$, $OCHF_2$, or $OCF_3$. In a further aspect, $R_1$ is $OCHF_2$ or $OCF_3$.

In one aspect, $R_{51}$ and $R_{52}$ are each H. In another aspect, one of $R_{51}$ and $R_{52}$ is H, and the other is F or Cl. In a further aspect, one of $R_{51}$ and $R_{52}$ is H, and the other is F. In another aspect, $R_{51}$ and $R_{52}$ are each F or Cl.

In another aspect, Q is

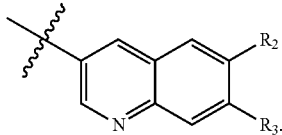

In one aspect, $R_2$ is F. In a further aspect, $R_2$ is F and $R_3$ is H. In another aspect, $R_2$ is $CH_2F$, $CHF_2$, or $CF_3$.

In one aspect, $R_3$ is F. In a further aspect, $R_3$ is F and $R_2$ is H. In another aspect, $R_3$ is $CH_2F$, $CHF_2$, or $CF_3$. In a further aspect, $R_3$ is $CF_3$. In a further aspect, $R_3$ is $CF_3$ and $R_2$ is H.

In one aspect, $R_2$ and $R_3$ are each F.

Any of the substituent groups illustrated above for any of X, Y, Z, Q, $R_1$, $R_2$, $R_3$, $R_4$, $R_{51}$, and $R_{52}$ can be combined with any of the substituent groups illustrated above for the remaining of X, Y, Z, Q, $R_1$, $R_2$, $R_3$, $R_4$, $R_{51}$, and $R_{52}$.

In one aspect, Q is

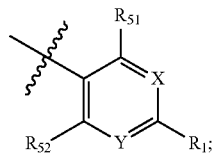

X is N or CH; Y is $CR_4$; $R_4$ is $CH_2F$, $CHF_2$, or $CF_3$; and $R_1$ is F or Cl. In a further aspect, $R_4$ is $CF_3$; and $R_1$ is F or Cl. In a further aspect, $R_1$ is F. In another further aspect, $R_1$ is Cl.

In one aspect, Z is

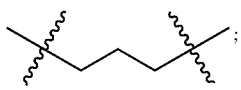

Q is

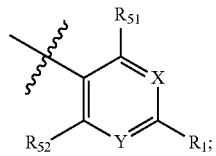

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In another further aspect, $R_1$ is methyl substituted with 1, 2, or 3 fluorine atoms or methoxy substituted with 0, 1, 2, or 3 fluorine atoms. In a further aspect, $R_1$ is $OCHF_2$ or $OCF_3$; X is N; and Y is CH. In another further aspect, $R_1$ is $CF_3$; X is N; and Y is N.

In one aspect, Z is

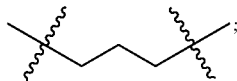 [SMILES: *CCC*]

Q is

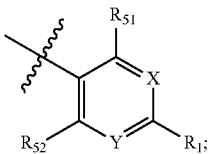

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In a further aspect, $R_4$ is $CH_2F$, $CHF_2$, or $CF_3$. In a further aspect, X is CH; Y is $CR_4$; $R_1$ is Cl; and $R_4$ is $CF_3$.

In one aspect, Z is

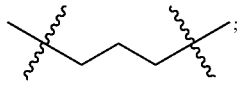 [SMILES: *CCC*]

Q is

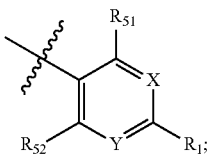

and $R_{51}$ and $R_{52}$ are each H. In another aspect, one of $R_{51}$ and $R_{52}$ is H, and the other is F or Cl. In a further aspect, one of $R_{51}$ and $R_{52}$ is H, and the other is F. In a further aspect, X is CH; Y is $CR_4$; and $R_4$ is $CF_3$.

In one aspect, Z is

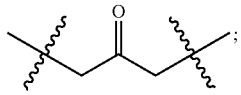 [SMILES: *CC(=O)C*]

Q is

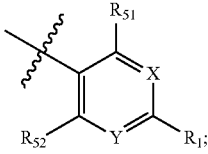

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In another aspect, $R_1$ is methyl substituted with 1, 2, or 3 fluorine atoms or methoxy substituted with 0, 1, 2, or 3 fluorine atoms. In a further aspect, $R_1$ is $OCHF_2$ or $OCF_3$; X is N; and Y is CH. In a further aspect, $R_1$ is $CF_3$; X is N; and Y is N.

In one aspect, Z is

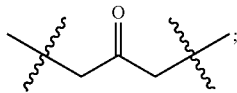 [SMILES: *CC(=O)C*]

Q is

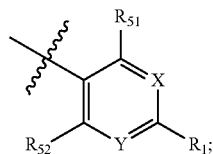

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In a further aspect, $R_4$ is $CH_2F$, $CHF_2$, or $CF_3$. In a further aspect, X is CH; Y is $CR_4$; $R_1$ is Cl; and $R_4$ is $CF_3$.

In one aspect, Z is

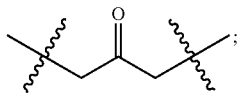 [SMILES: *CC(=O)C*]

Q is

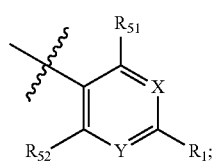

and $R_{51}$ and $R_{52}$ are each H. In another aspect, one of $R_{51}$ and $R_{52}$ is H, and the other is F or Cl. In a further aspect, one of $R_{51}$ and $R_{52}$ is H, and the other is F. In a further aspect, X is CH; Y is $CR_4$; and $R_4$ is $CF_3$.

In one aspect, Z is

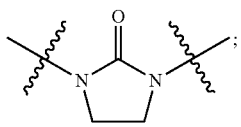 [SMILES: *N1CCN(*)C1=O]

Q is

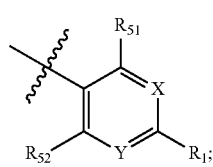

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In another aspect, $R_1$ is methyl substituted with 1, 2, or 3 fluorine atoms or methoxy substituted with 0, 1, 2, or 3 fluorine atoms. In a further aspect, $R_1$ is $OCHF_2$ or $OCF_3$; X is N; and Y is CH. In a further aspect, $R_1$ is $CF_3$; X is N; and Y is N.

In one aspect, Z is

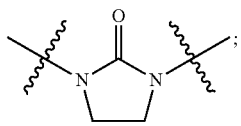 [SMILES: *N1CCN(*)C1=O]

Q is

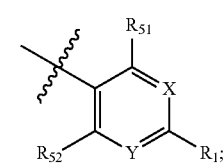

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In a further aspect, $R_4$ is $CH_2F$, $CHF_2$, or $CF_3$. In a further aspect, X is CH; Y is $CR_4$; $R_1$ is Cl; and $R_4$ is $CF_3$.

In one aspect, Z is

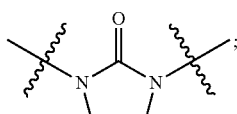

Q is

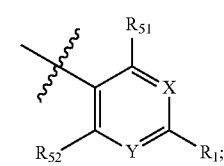

and $R_{51}$ and $R_{52}$ are each H. In another aspect, one of $R_{51}$ and $R_{52}$ is H, and the other is F or Cl. In a further aspect, one of $R_{51}$ and $R_{52}$ is H, and the other is F. In a further aspect, X is CH; Y is $CR_4$; and $R_4$ is $CF_3$.

In one aspect, a compound of present invention is of formula II:

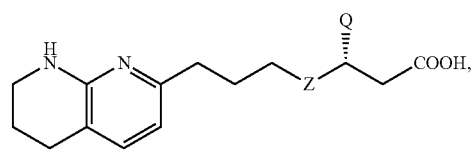

(II)

or a pharmaceutically acceptable salt or solvate thereof, wherein each of the variables is as defined above. Compounds of the present invention include compounds of formula II, wherein the variables and combinations thereof are illustrated in the various aspects of formula I above.

In one aspect, a compound of present invention is of formula IIIa or IIIb:

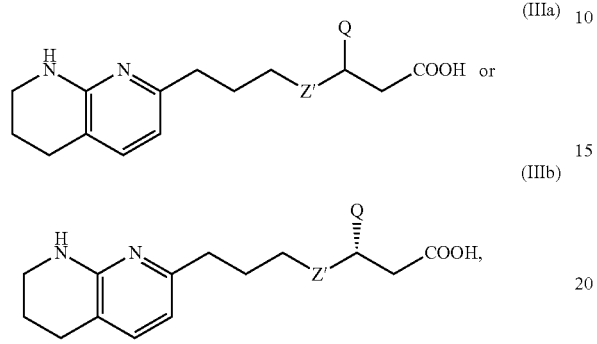

or a pharmaceutically acceptable salt or solvate thereof, wherein Z' is

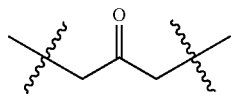 [SMILES: *CC(=O)C*]

and each of the other variables is as defined above. Compounds of the present invention include compounds of formula IIIa or IIIb, wherein the variables and combinations thereof are illustrated in the various aspects of formula I above.

In one aspect, Q is

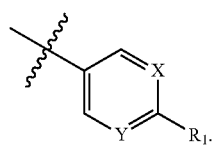

In one aspect, X is N and Y is $CR_4$. In another aspect, X and Y are each $CR_4$. In another aspect, X and Y are each N.

In one aspect, at least one $R_4$ is H. In one aspect, at least one $R_4$ is $CH_2F$, $CHF_2$, or $CF_3$. In a further aspect, at least one $R_4$ is $CF_3$.

In one aspect, a compound of present invention is of formula IVa or IVb:

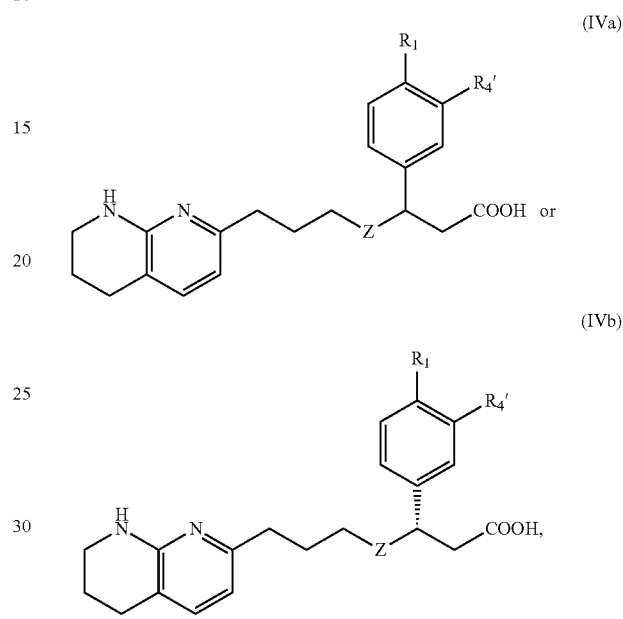

or a pharmaceutically acceptable salt or solvate thereof, wherein $R_4'$ is $CH_2F$, $CHF_2$, or $CF_3$, and each of the other variables are as defined above. Compounds of the present invention include compounds of formula IVa or IVb, wherein the variables and combinations thereof are illustrated in the various aspects of formula I above.

In one aspect, $R_1$ is H, F, or Cl. In a further aspect, $R_1$ is F or Cl. $R_1$ is Cl.

In one aspect, $R_4'$ is $CF_3$.

Representative compounds of the present invention include the compounds listed in Table 1.

TABLE 1

| Cmpd # | Chemical Structure |
|---|---|
| A15 | 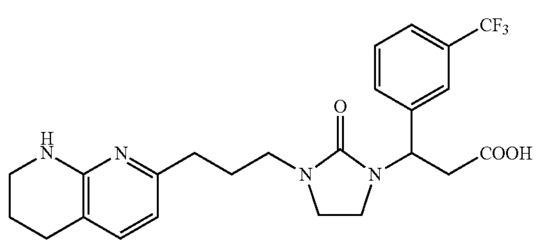 [SMILES: O=C(O)CC(c1cccc(C(F)(F)F)c1)N1CCN(CCCc2ccc3c(n2)NCCC3)C1=O] |

TABLE 1-continued

| Cmpd # | Chemical Structure |
| --- | --- |
| A15s | 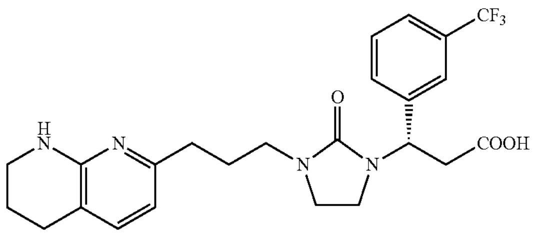 [SMILES: O=C(O)C[C@@H](c1cccc(C(F)(F)F)c1)N1CCN(CCCc2ccc3c(n2)NCCC3)C1=O] |
| A16 | 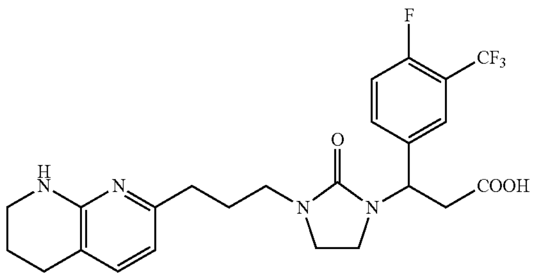 [SMILES: O=C(O)CC(c1ccc(F)c(C(F)(F)F)c1)N1CCN(CCCc2ccc3c(n2)NCCC3)C1=O] |
| A16s | 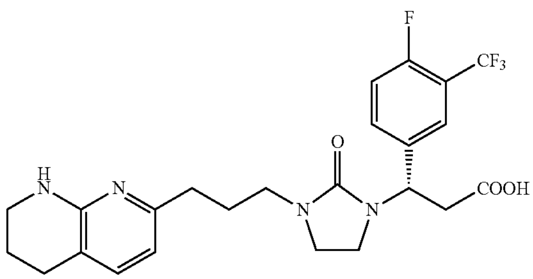 [SMILES: O=C(O)C[C@@H](c1ccc(F)c(C(F)(F)F)c1)N1CCN(CCCc2ccc3c(n2)NCCC3)C1=O] |
| A17 | 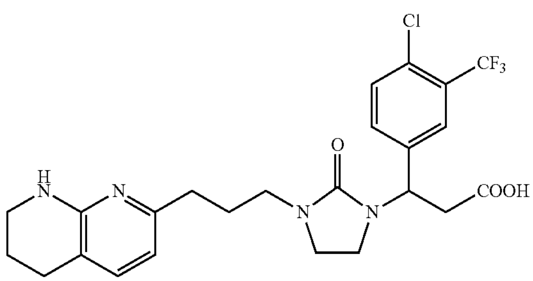 |
| A17s | 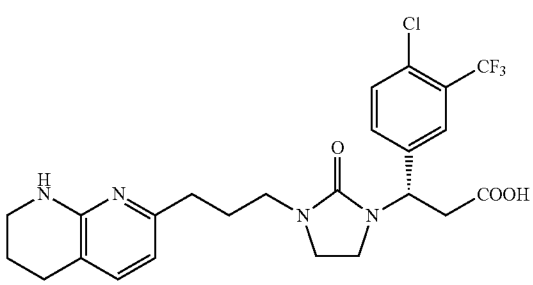 |
| A18 | 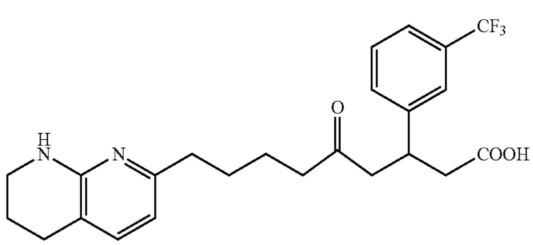 [SMILES: O=C(O)CC(CC(=O)CCCCc1ccc2c(n1)NCCC2)c1cccc(C(F)(F)F)c1] |

TABLE 1-continued
| Cmpd # | Chemical Structure |
|---|---|
| A18s | 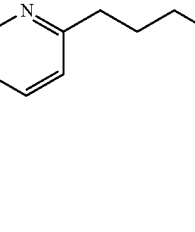 |
| A19 | 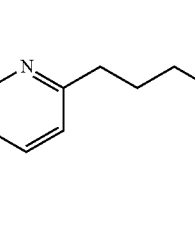 |
| A19s | 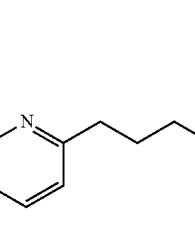 |
| A20 | 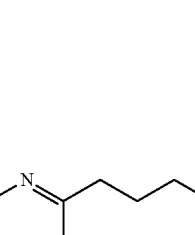 |
| A20s | 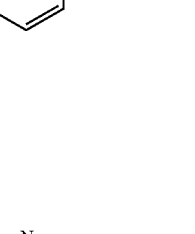 |
| A21 | 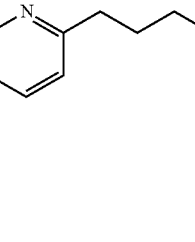 |

TABLE 1-continued

| Cmpd # | Chemical Structure |
|---|---|
| A21s | *(structure: 5,6,7,8-tetrahydro-1,8-naphthyridin-2-yl alkyl chain with (S)-configured CH bearing 3-CF₃-phenyl and CH₂COOH)* |
| A21-1 enantiomer 1 | *(structure: 5,6,7,8-tetrahydro-1,8-naphthyridin-2-yl alkyl chain with CH bearing 3-CF₃-phenyl and CH₂COOH)* |
| A21-2 enantiomer 2 | *(structure: 5,6,7,8-tetrahydro-1,8-naphthyridin-2-yl alkyl chain with CH bearing 3-CF₃-phenyl and CH₂COOH)* |
| A22 | *(structure: 5,6,7,8-tetrahydro-1,8-naphthyridin-2-yl alkyl chain with CH bearing 4-F-3-CF₃-phenyl and CH₂COOH)* |
| A22s | *(structure: 5,6,7,8-tetrahydro-1,8-naphthyridin-2-yl alkyl chain with (S)-configured CH bearing 4-F-3-CF₃-phenyl and CH₂COOH)* |
| A23 | *(structure: 5,6,7,8-tetrahydro-1,8-naphthyridin-2-yl alkyl chain with CH bearing 4-Cl-3-CF₃-phenyl and CH₂COOH)* |

TABLE 1-continued

| Cmpd # | Chemical Structure |
| --- | --- |
| A23s | (4-Cl, 3-CF3-phenyl) substituted 5,6,7,8-tetrahydro-1,8-naphthyridine alkanoic acid with (S)-configuration at the α-carboxy carbon |
| A24 | (3-Cl, 5-CF3-phenyl) substituted 5,6,7,8-tetrahydro-1,8-naphthyridine alkanoic acid |
| A24s | (3-Cl, 5-CF3-phenyl) substituted 5,6,7,8-tetrahydro-1,8-naphthyridine alkanoic acid with (S)-configuration |
| A25 | 2-(trifluoromethyl)pyrimidin-5-yl substituted keto-alkanoic acid with 5,6,7,8-tetrahydro-1,8-naphthyridine |
| A25s | 2-(trifluoromethyl)pyrimidin-5-yl substituted keto-alkanoic acid with 5,6,7,8-tetrahydro-1,8-naphthyridine, (S)-configuration |
| A26 | 6-(trifluoromethoxy)pyridin-3-yl substituted keto-alkanoic acid with 5,6,7,8-tetrahydro-1,8-naphthyridine |

TABLE 1-continued

| Cmpd # | Chemical Structure |
| --- | --- |
| A26s | 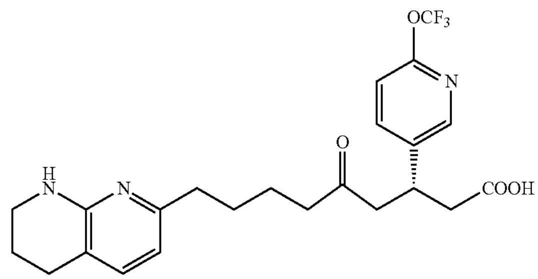 [SMILES: O=C(O)C[C@H](CC(=O)CCCCc1ccc2c(n1)NCCC2)c1ccc(OC(F)(F)F)nc1] |
| A27 | 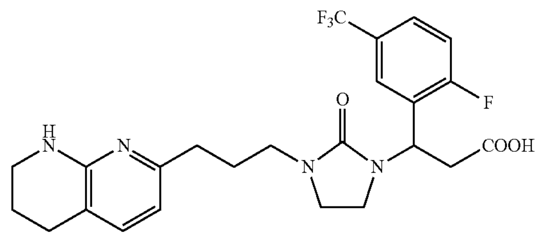 [SMILES: O=C(O)CC(c1cc(C(F)(F)F)ccc1F)N1CCN(CCCc2ccc3c(n2)NCCC3)C1=O] |
| A27s | 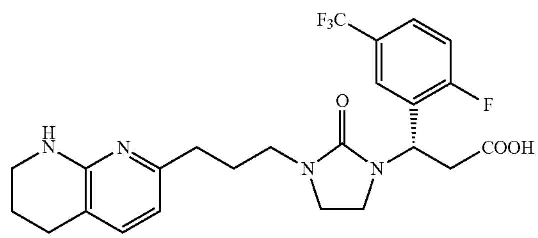 [SMILES: O=C(O)C[C@@H](c1cc(C(F)(F)F)ccc1F)N1CCN(CCCc2ccc3c(n2)NCCC3)C1=O] |
| A28 | 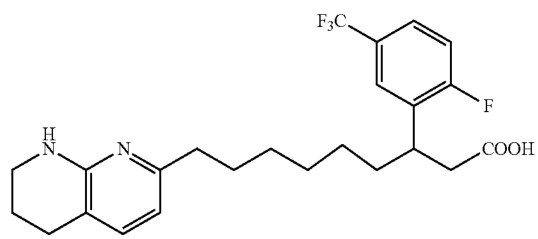 [SMILES: O=C(O)CC(CCCCCCc1ccc2c(n1)NCCC2)c1cc(C(F)(F)F)ccc1F] |
| A28s | 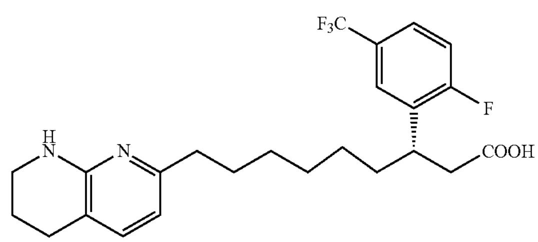 [SMILES: O=C(O)C[C@H](CCCCCCc1ccc2c(n1)NCCC2)c1cc(C(F)(F)F)ccc1F] |
| A29 | 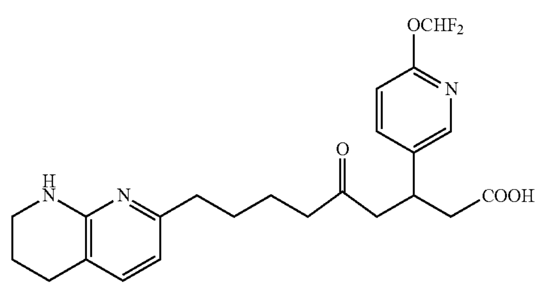 [SMILES: O=C(O)CC(CC(=O)CCCCc1ccc2c(n1)NCCC2)c1ccc(OC(F)F)nc1] |

TABLE 1-continued

| Cmpd # | Chemical Structure |
|---|---|
| A29s | 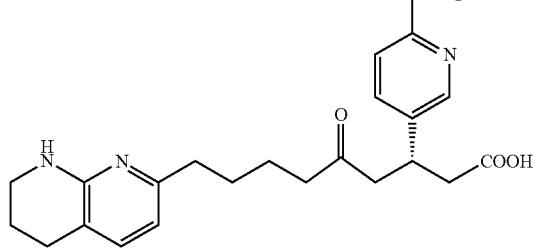 |
| A30 | 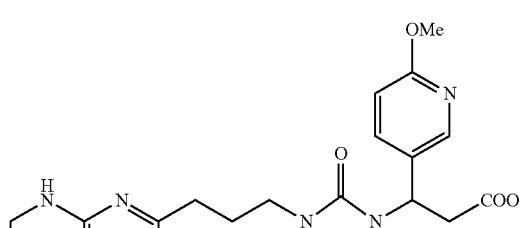 |
| A30s | 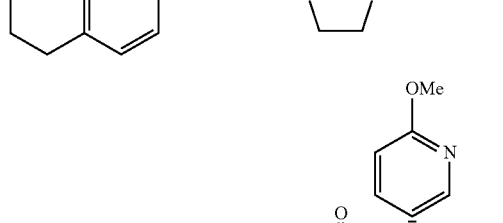 |

The present invention also relates to use of a compound of formula Ia:

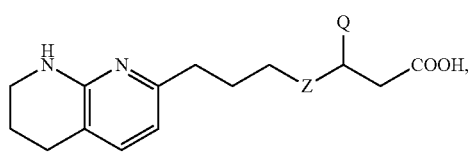

(Ia)

or a pharmaceutically acceptable salt or solvate thereof, for treating or preventing fibrosis, wherein:

Z is

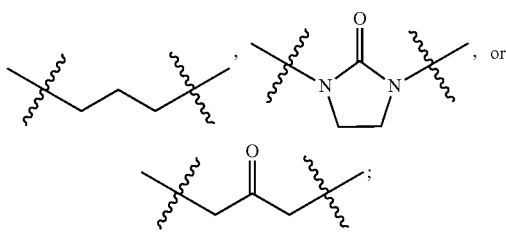, or

Q is

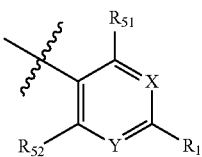

X is $CR_4$ or N;
Y is $CR_4$ or N;
$R_1$ is H, F, Cl, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms;
$R_2$ and $R_3$ are each independently H, F, $CH_2F$, $CHF_2$, or $CF_3$, provided that one of $R_2$ and $R_3$ is not H;
each $R_4$ is independently H, $CH_2F$, $CHF_2$, or $CF_3$; and
$R_{51}$ and $R_{52}$ are each independently H, F, or Cl;
provided that the compound of formula Ia contains at least one fluorine atom.

The compounds of the present invention contain at least one fluorine atom. In one aspect, the compounds of the present invention contain at least one fluorine atom in the $R_1$ substituent. In another aspect, the compounds of the present invention contain at least one fluorine atom in the $R_2$ or $R_3$ substituent. In another aspect, the compounds of the present invention contain at least one fluorine atom in the $R_4$ substituent.

In one aspect, Z is

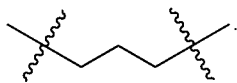 [SMILES: *CCC*]

In another aspect, Z is

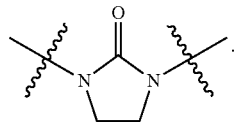 [SMILES: *N1CCN(*)C1=O]

In another aspect, Z is

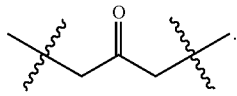 [SMILES: *CC(=O)C*]

In one aspect, Q is

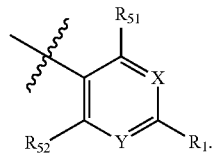

In one aspect, X is N and Y is $CR_4$. In another aspect, X and Y are each $CR_4$. In another aspect, X and Y are each N.

In one aspect, at least one $R_4$ is H. In one aspect, at least one $R_4$ is $CH_2F$, $CHF_2$, or $CF_3$. In a further aspect, at least one $R_4$ is $CF_3$.

In one aspect, $R_1$ is H. In another aspect, $R_1$ is F, Cl, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is F or Cl. In another aspect, $R_1$ is $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms.

In a further aspect, $R_1$ is straight chain $C_1$-$C_4$ or branched $C_3$-$C_4$ alkyl, and is substituted with 1, 2, 3, 4, 5, 6, 7, 8, or 9 fluorine atoms. In a further aspect, $R_1$ is methyl, ethyl, propyl, or butyl, and is substituted with 1, 2, 3, 4, 5, 6, 7, 8, or 9 fluorine atoms. In a further aspect, $R_1$ is methyl substituted with 1, 2, or 3 fluorine atoms. In a further aspect, $R_1$ is $CF_3$.

In another further aspect, $R_1$ is straight chain $C_1$-$C_6$ or branched $C_3$-$C_6$ alkoxy, and is substituted with 0, 1, 2, 3, 4, 5, 6, or 7 fluorine atoms. In a further aspect, $R_1$ is methoxy, ethoxy, propoxy, or butoxy, and is substituted with 0, 1, 2, 3, 4, 5, 6, or 7 fluorine atoms. In a further aspect, $R_1$ is methoxy substituted with 0, 1, 2, or 3 fluorine atoms. In a further aspect, $R_1$ is $OCH_3$, $OCH_2F$, $OCHF_2$, or $OCF_3$. In a further aspect, $R_1$ is $OCHF_2$ or $OCF_3$.

In one aspect, $R_{51}$ and $R_{52}$ are each H. In another aspect, one of $R_{51}$ and $R_{52}$ is H, and the other is F or Cl. In a further aspect, one of $R_{51}$ and $R_{52}$ is H, and the other is F. In another aspect, $R_{51}$ and $R_{52}$ are each F or Cl.

In another aspect, Q is

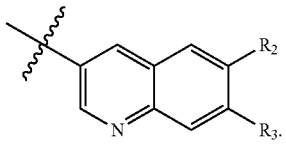

In one aspect, $R_2$ is F. In a further aspect, $R_2$ is F and $R_3$ is H. In another aspect, $R_2$ is $CH_2F$, $CHF_2$, or $CF_3$.

In one aspect, $R_3$ is F. In a further aspect, $R_3$ is F and $R_2$ is H. In another aspect, $R_3$ is $CH_2F$, $CHF_2$, or $CF_3$. In a further aspect, $R_3$ is $CF_3$. In a further aspect, $R_3$ is $CF_3$ and $R_2$ is H.

In one aspect, $R_2$ and $R_3$ are each F.

Any of the substituent groups illustrated above for any of X, Y, Z, Q, $R_1$, $R_2$, $R_3$, $R_4$, $R_{51}$, and $R_{52}$ can be combined with any of the substituent groups illustrated above for the remaining of X, Y, Z, Q, $R_1$, $R_2$, $R_3$, $R_4$, $R_{51}$, and $R_{52}$.

In one aspect, Q is

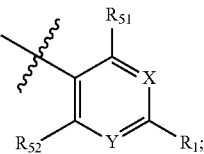

X is N or CH; Y is $CR_4$; $R_4$ is $CH_2F$, $CHF_2$, or $CF_3$; and $R_1$ is F or Cl. In a further aspect, $R_4$ is $CF_3$; and $R_1$ is F or Cl. In a further aspect, $R_1$ is F. In another further aspect, $R_1$ is Cl.

In one aspect, Z is

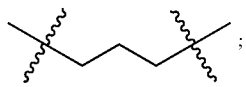 [SMILES: *CCC*]

Q is

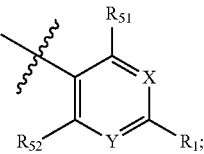

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In another further aspect, $R_1$ is methyl substituted with 1, 2, or 3 fluorine atoms or methoxy substituted with 0, 1, 2, or 3 fluorine atoms. In a further aspect, $R_1$ is $OCHF_2$ or $OCF_3$; X is N; and Y is CH. In another further aspect, $R_1$ is $CF_3$; X is N; and Y is N.

In one aspect, Z is

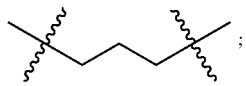 [SMILES: *CCC*]

Q is

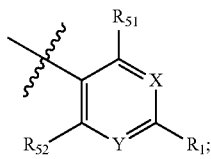

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In a further aspect, $R_4$ is $CH_2F$, $CHF_2$, or $CF_3$. In a further aspect, X is CH; Y is $CR_4$; $R_1$ is Cl; and $R_4$ is $CF_3$.

In one aspect, Z is

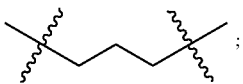 [SMILES: *CCC*]

Q is

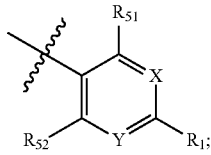

and $R_{51}$ and $R_{52}$ are each H. In another aspect, one of $R_{51}$ and $R_{52}$ is H, and the other is F or Cl. In a further aspect, one of $R_{51}$ and $R_{52}$ is H, and the other is F. In a further aspect, X is CH; Y is $CR_4$; and $R_4$ is $CF_3$.

In one aspect, Z is

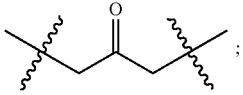 [SMILES: *CC(=O)C*]

Q is

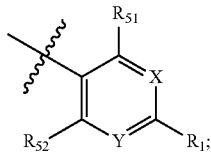

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In another aspect, $R_1$ is methyl substituted with 1, 2, or 3 fluorine atoms or methoxy substituted with 0, 1, 2, or 3 fluorine atoms. In a further aspect, $R_1$ is $OCHF_2$ or $OCF_3$; X is N; and Y is CH. In a further aspect, $R_1$ is $CF_3$; X is N; and Y is N.

In one aspect, Z is

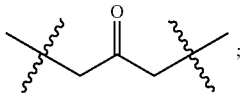 [SMILES: *CC(=O)C*]

Q is

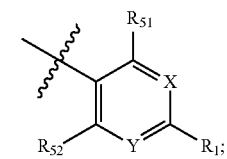

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In a further aspect, $R_4$ is $CH_2F$, $CHF_2$, or $CF_3$. In a further aspect, X is CH; Y is $CR_4$; $R_1$ is Cl; and $R_4$ is $CF_3$.

In one aspect, Z is

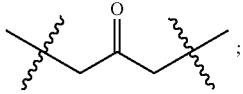 [SMILES: *CC(=O)C*]

Q is

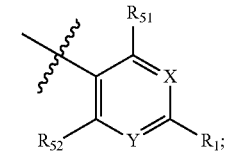

and $R_{51}$ and $R_{52}$ are each H. In another aspect, one of $R_{51}$ and $R_{52}$ is H, and the other is F or Cl. In a further aspect, one of $R_{51}$ and $R_{52}$ is H, and the other is F. In a further aspect, X is CH; Y is $CR_4$; and $R_4$ is $CF_3$.

In one aspect, Z is

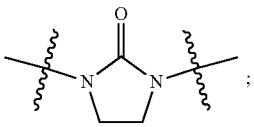 [SMILES: *N1CCN(*)C1=O]

Q is

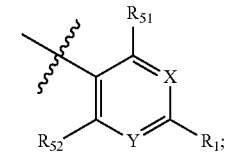

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In another aspect, $R_1$ is methyl substituted with 1, 2, or 3 fluorine atoms or methoxy substituted with 0, 1, 2, or 3 fluorine atoms. In a further aspect, $R_1$ is $OCHF_2$ or $OCF_3$; X is N; and Y is CH. In a further aspect, $R_1$ is $CF_3$; X is N; and Y is N.

In one aspect, Z is

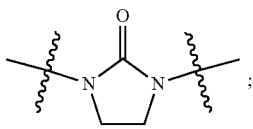 [SMILES: *N1CCN(*)C1=O]

Q is

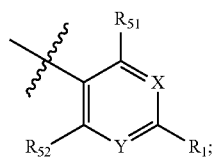

and $R_1$ is Cl, F, $C_1$-$C_4$ alkyl substituted with 1, 2, 3, 4, 5, 6, 7, 8, or 9 fluorine atoms, or $C_1$-$C_6$ alkoxy substituted with 0, 1, 2, 3, 4, 5, 6, or 7 fluorine atoms. In a further aspect, $R_1$ is Cl or F. In a further aspect, $R_4$ is $CH_2F$, $CHF_2$, or $CF_3$. In a further aspect, X is CH; Y is $CR_4$; $R_1$ is Cl; and $R_4$ is $CF_3$.

In one aspect, Z is

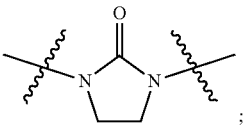

Q is

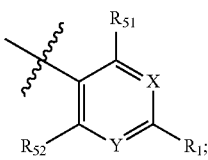

and $R_{51}$ and $R_{52}$ are each H. In another aspect, one of $R_{51}$ and $R_{52}$ is H, and the other is F or Cl. In a further aspect, one of $R_{51}$ and $R_{52}$ is H, and the other is F. In a further aspect, X is CH; Y is $CR_4$; and $R_4$ is $CF_3$.

Representative compounds of the present invention for use in treating or preventing fibrosis include the compounds listed in Table 1 above and Table 2 below.

TABLE 2

| Cmpd # | Chemical Structure |
|---|---|
| A1 | 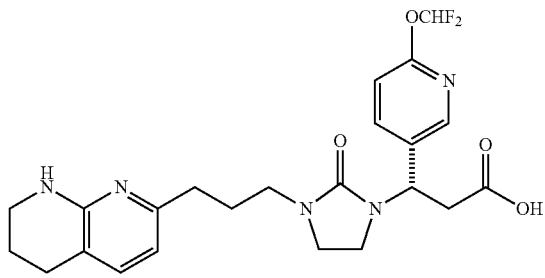 [SMILES: O=C(O)C[C@@H](c1ccc(OC(F)F)nc1)N1CCN(CCCc2ccc3c(n2)NCCC3)C1=O] |
| A2 | 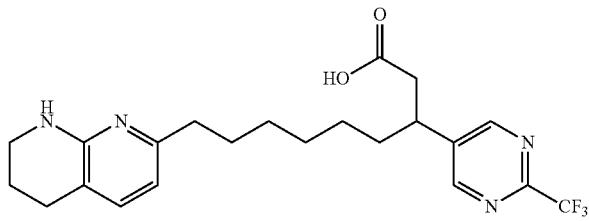 [SMILES: O=C(O)CC(CCCCCCc1ccc2c(n1)NCCC2)c1cnc(C(F)(F)F)nc1] |
| A3 | 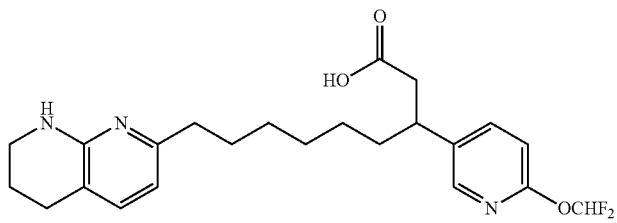 [SMILES: O=C(O)CC(CCCCCCc1ccc2c(n1)NCCC2)c1ccc(OC(F)F)nc1] |

TABLE 2-continued

| Cmpd # | Chemical Structure |
| --- | --- |
| A4 | (structure: tetrahydronaphthyridine–(CH2)5–CH(CH2COOH)–6-fluoroquinolin-3-yl) |
| A5 | (structure: tetrahydronaphthyridine–(CH2)5–CH(CH2COOH)–7-fluoroquinolin-3-yl) |
| A6 | (structure: tetrahydronaphthyridine–(CH2)5–CH(CH2COOH)–6,7-difluoroquinolin-3-yl) |
| A7 | (structure: tetrahydronaphthyridine–(CH2)5–CH(CH2COOH)–7-trifluoromethylquinolin-3-yl) |

In one aspect, a compound of the present invention inhibits the activity of one or more αv integrins (e.g., αvβ3, αvβ5, αvβ6, and αvβ8). In a further aspect, a compound of the present invention inhibits the activity of αvβ3. In another further aspect, a compound of the present invention inhibits the activity of αvβ5. In another further aspect, a compound of the present invention inhibits the activity of αvβ6. In another further aspect, a compound of the present invention inhibits the activity of αvβ8. In yet another further aspect, a compound of the present invention inhibits the activity of αvβ3 and αvβ5. In yet another further aspect, a compound of the present invention inhibits the activity of αvβ6 and αvβ8. In a further aspect, a compound of the present invention inhibits the activity of αvβ3, αvβ5, αvβ6, and/or αvβ8 at a submicromolar concentration, e.g., below 1 μM, 0.8 μM, 0.6 μM, 0.5 μM, 0.2 μM, or 0.1 μM.

In one aspect, a compound of the present invention inhibits cellular adhesion to vitronectin through the αv integrin (e.g., αvβ3 and αvβ5) at or below an $IC_{50}$ of 2.0E-07 M using a human dermal microvascular endothelial cell (HMVEC) assay. In a further aspect, a compound of the present invention inhibits cellular adhesion to vitronectin through the αv integrin (e.g., αvβ3 and αvβ5) at or below an $IC_{50}$ of 2.5E-08 M using an HMVEC assay. In a further aspect, a compound of the present invention inhibits cellular adhesion to vitronectin through the αv integrin (e.g., αvβ3 and αvβ5) at or below an $IC_{50}$ of 1.0E-08 M using an HMVEC assay. In one aspect, a compound of the present invention inhibits cellular adhesion to vitronectin through the αv integrin (e.g., αvβ3 and αvβ5) at or below an $IC_{50}$ of 2.5E-07 M using a rat lung microvascular endothelial cell (RLMVEC) assay. In a further aspect, a compound of the present invention inhibits cellular adhesion to vitronectin through the αv integrin (e.g., αvβ3 and αvβ5) at or below an $IC_{50}$ of 3.5E-08 M using an RLMVEC assay. In one aspect, a compound of the present invention inhibits cellular adhesion to vitronectin through the αv integrin (e.g., αvβ3 and αvβ5) at or below an $IC_{50}$ of 2.0E-08 M using a rabbit aortic endothelial cell (RAEC) assay. In a further aspect, a compound of the present invention inhibits cellular adhesion to vitronectin through the αv integrin (e.g., αvβ3 and αvβ5) at or below an $IC_{50}$ of 1.0E-08 M using an RAEC assay.

In one aspect, a compound of the present invention inhibits cellular adhesion to fibronectin through the αv integrin (e.g., αvβ6 and αvβ8) at a micromolar concentration (e.g., at or below an $IC_{50}$ of 1.0E-05 M using a fibronectin binding assay). In a further aspect, a compound of the present invention inhibits cellular adhesion to fibronectin through the αv integrin (e.g., αvβ6 and αvβ8) at a submicromolar concentration (e.g., at or below an $IC_{50}$ of 1.0E-06 M using a fibronectin binding assay). In one aspect, a compound of the present invention inhibits cellular adhesion to fibronectin through the αv integrin (e.g., αvβ6 and αvβ8) at a nanomolar concentration (e.g., at or below an IC$_{50}$ of 1.0E-08 M using a fibronectin binding assay). In a further aspect, a compound of the present invention inhibits cellular adhesion to fibronectin through the αv integrin (e.g., αvβ6 and αvβ8) at a subnanomolar concentration (e.g., at or below an IC$_{50}$ of 1.0E-09 M using a fibronectin binding assay).

In one aspect, the compounds of the present invention are selective for one αv integrin (e.g., αvβ3, αvβ5, αvβ6, or αvβ8) over other αv integrins (e.g., αvβ3, αvβ5, αvβ6, or αvβ8). As used herein, "selective" means that a compound, for example a compound of the invention, inhibits one αv integrin to a greater extent than other αv integrins.

A "selective αv integrin inhibitor" can be identified, for example, by comparing the ability of a compound to inhibit one αv integrin activity to its ability to inhibit other αv integrins. For example, a compound may be assayed for its ability to inhibit αvβ6 activity, as well as αvβ3, αvβ5, and αvβ8 or other αv integrins.

In certain embodiments, the compounds of the invention exhibit at least 1.2-fold, 1.5-fold, 2-fold, 3-fold, 5-fold, 10-fold, 25-fold, 50-fold or 100-fold selectivity for one αv integrin over other αv integrins as measured by IC$_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for one αv integrin over other αv integrins. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for one αv integrin over other αv integrins. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for one αv integrin over other αv integrins.

In one embodiment, the compounds of the invention exhibit at least 1.2-fold, 1.5-fold, 2-fold, 3-fold, 5-fold, 10-fold, 25-fold, 50-fold or 100-fold selectivity for αvβ3 over the αvβ5, αvβ6, and/or αvβ8 integrin (e.g., as measured by IC$_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ3 over the αvβ5, αvβ6, and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ3 over the αvβ5, αvβ6, and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ3 over the αvβ5, αvβ6, and/or αvβ8 integrin.

In another embodiment, the compounds of the invention exhibit at least 1.2-fold, 1.5-fold, 2-fold, 3-fold, 5-fold, 10-fold, 25-fold, 50-fold or 100-fold selectivity for αvβ5 over the αvβ3, αvβ6, and/or αvβ8 integrin (e.g., as measured by IC$_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ5 over the αvβ3, αvβ6, and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ5 over the αvβ3, αvβ6, and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ5 over the αvβ3, αvβ6, and/or αvβ8 integrin.

In another embodiment, the compounds of the invention exhibit at least 1.2-fold, 1.5-fold, 2-fold, 3-fold, 5-fold, 10-fold, 25-fold, 50-fold or 100-fold selectivity for αvβ6 over the αvβ3, αvβ5, and/or αvβ8 integrin (e.g., as measured by IC$_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ6 over the αvβ3, αvβ5, and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ6 over the αvβ3, αvβ5, and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ6 over the αvβ3, αvβ5, and/or αvβ8 integrin.

In another embodiment, the compounds of the invention exhibit at least 1.2-fold, 1.5-fold, 2-fold, 3-fold, 5-fold, 10-fold, 25-fold, 50-fold or 100-fold selectivity for αvβ6 over the αvβ8 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ6 over the αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ6 over the αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ6 over the αvβ8 integrin.

In another embodiment, the compounds of the invention exhibit at least 1.2-fold, 1.5-fold, 2-fold, 3-fold, 5-fold, 10-fold, 25-fold, 50-fold or 100-fold selectivity for αvβ8 over the αvβ3, αvβ5, and/or αvβ6 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ8 over the αvβ3, αvβ5, and/or αvβ6 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ8 over the αvβ3, αvβ5, and/or αvβ6 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ8 over the αvβ3, αvβ5, and/or αvβ6 integrin.

In another embodiment, the compounds of the invention exhibit at least 1.2-fold, 1.5-fold, 2-fold, 3-fold, 5-fold, 10-fold, 25-fold, 50-fold or 100-fold selectivity for αvβ8 over the αvβ6 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for αvβ8 over the αvβ6 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for αvβ8 over the αvβ6 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for αvβ8 over the αvβ6 integrin.

In another embodiment, the compounds of the invention exhibit at least 1.2-fold, 1.5-fold, 2-fold, 3-fold, 5-fold, 10-fold, 25-fold, 50-fold or 100-fold selectivity for each of αvβ6 and αvβ8 over the αvβ3 and/or αvβ5 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of αvβ6 and αvβ8 over the αvβ3 and/or αvβ5 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of αvβ6 and αvβ8 over the αvβ3 and/or αvβ5 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of αvβ6 and αvβ8 over the αvβ3 and/or αvβ5 integrin.

In another embodiment, the compounds of the invention exhibit at least 1.2-fold, 1.5-fold, 2-fold, 3-fold, 5-fold, 10-fold, 25-fold, 50-fold or 100-fold selectivity for each of αvβ3 and αvβ5 over the αvβ6 and/or αvβ8 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of αvβ3 and αvβ5 over the αvβ6 and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of αvβ3 and αvβ5 over the αvβ6 and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of αvβ3 and αvβ5 over the αvβ6 and/or αvβ8 integrin.

In another embodiment, the compounds of the invention exhibit at least 1.2-fold, 1.5-fold, 2-fold, 3-fold, 5-fold, 10-fold, 25-fold, 50-fold or 100-fold selectivity for each of αvβ5 and αvβ6 over the αvβ3 and/or αvβ8 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of αvβ5 and αvβ6 over the αvβ3 and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of αvβ5 and αvβ6 over the αvβ3 and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of αvβ5 and αvβ6 over the αvβ3 and/or αvβ8 integrin.

In another embodiment, the compounds of the invention exhibit at least 1.2-fold, 1.5-fold, 2-fold, 3-fold, 5-fold, 10-fold, 25-fold, 50-fold or 100-fold selectivity for each of αvβ3 and αvβ6 over the αvβ5 and/or αvβ8 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of αvβ3 and αvβ6 over the αvβ5 and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of αvβ3 and αvβ6 over the αvβ5 and/or αvβ8 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of αvβ3 and αvβ6 over the αvβ5 and/or αvβ8 integrin.

In another embodiment, the compounds of the invention exhibit at least 1.2-fold, 1.5-fold, 2-fold, 3-fold, 5-fold, 10-fold, 25-fold, 50-fold or 100-fold selectivity for each of αvβ3 and αvβ8 over the αvβ5 and/or αvβ6 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of αvβ3 and αvβ8 over the αvβ5 and/or αvβ6 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of αvβ3 and αvβ8 over the αvβ5 and/or αvβ6 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of αvβ3 and αvβ8 over the αvβ5 and/or αvβ6 integrin.

In another embodiment, the compounds of the invention exhibit at least 1.2-fold, 1.5-fold, 2-fold, 3-fold, 5-fold, 10-fold, 25-fold, 50-fold or 100-fold selectivity for each of αvβ5 and αvβ8 over the αvβ3 and/or αvβ6 integrin (e.g., as measured by $IC_{50}$). In various embodiments, the compounds of the invention exhibit up 1.2-fold to 1.5-fold, 1.2-fold to 2-fold, 1.2-fold to 5-fold, 1.2-fold to 10-fold, 1.2-fold to 25-fold, 1.2-fold to 50-fold, 1.2-fold to 100-fold, 1.2-fold to 500-fold, 1.2-fold to 1000-fold, 1.5-fold to 2-fold, 1.5-fold to 5-fold, 1.5-fold to 10-fold, 1.5-fold to 25-fold, 1.5-fold to 50-fold, 1.5-fold to 100-fold, 1.5-fold to 500-fold, 1.5-fold to 1000-fold, 2-fold to 5-fold, 2-fold to 10-fold, 2-fold to 25-fold, 2-fold to 50-fold, 2-fold to 100-fold, 2-fold to 500-fold, 2-fold to 1000-fold, 5-fold to 10-fold, 5-fold to 25-fold, 5-fold to 50-fold, 5-fold to 100-fold, 5-fold to 500-fold, 5-fold to 1000-fold, 10-fold to 25-fold, 10-fold to 50-fold, 10-fold to 100-fold, 10-fold to 500-fold, or 10-fold to 1000-fold selectivity for each of αvβ5 and αvβ8 over the αvβ3 and/or αvβ6 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, 10-fold to 25-fold, 25-fold to 50-fold, 50-fold to 100-fold, or 100-fold to 1000-fold selectivity for each of αvβ5 and αvβ8 over the αvβ3 and/or αvβ6 integrin. In various embodiments, the compounds of the invention exhibit up 1.2-fold to 1.5-fold, 1.2-fold to 2-fold, 1.5-fold to 2-fold, 2-fold to 5-fold, 5-fold to 10-fold, or 10-fold to 25-fold selectivity for each of αvβ5 and αvβ8 over the αvβ3 and/or αvβ6 integrin.

In one aspect, a compound of the present invention inhibits or decreases formation of blood vessels in a tissue or organ, in vivo or in vitro. In one aspect, a compound of the present invention decreases the formation of blood vessels below 90%, 80%, 70%, 60%, 50%, 40%, 30%, 20%, 10%, or 5%, as compared to that in an untreated control. In a further aspect, a compound of the present invention decreases the formation of blood vessels below 60%, 50%, 40%, 30%, 20%, 10%, or 5%, as compared to that in an untreated control. In a further aspect, a compound of the present invention decreases the formation of blood vessels below 40%, 30%, 20%, 10%, or 5%, as compared to that in an untreated control. In one aspect, the tissue is a tissue from the eye, such as a retinal tissue. In one aspect, the organ is the eye.

In one aspect, a compound of the present invention is efficiently distributed to the back of the eye, e.g., retina, after topical administration. In one aspect, a compound of the present invention is efficiently distributed to the retina within 12 hours, 10 hours, 8 hours, 6 hours, 4 hours, 2 hours, or 1 hour, after topical administration to the eye. In a further aspect, a compound of the present invention is efficiently distributed to the retina within 8 hours, 6 hours, 4 hours, 2 hours, or 1 hour, after topical administration to the eye.

In one aspect, a compound of the present invention inhibits or decreases formation of fibrotic tissue in an organ (e.g., kidney, lung, liver, and heart). In one aspect, a compound of the present invention decreases the formation of fibrotic tissue below 90%, 80%, 70%, 60%, 50%, 40%, 30%, 20%, 10%, or 5%, as compared to that in an untreated control. In a further aspect, a compound of the present invention decreases the formation of fibrotic tissue below 60%, 50%, 40%, 30%, 20%, 10%, or 5%, as compared to that in an untreated control. In a further aspect, a compound of the present invention decreases the formation of fibrotic tissue below 40%, 30%, 20%, 10%, or 5%, as compared to that in an untreated control.

Synthesis of the Compounds of the Invention

Compounds of the present invention can be conveniently prepared by a variety of methods familiar to those skilled in the art (e.g., according to the methods described in WO 2014/124302, the entire contents of which are incorporated by reference). The compounds of each of the formulae described herein may be prepared according to the following procedures from commercially available starting materials or starting materials which can be prepared using literature procedures. These procedures show the preparation of representative compounds of this invention. It is understood that compounds of the present invention other than those illustrated in the following schemes can be made using these schemes with modifications commonly known in the art (e.g., using different starting material, changing reaction solvents, or adjusting reaction duration or temperature).

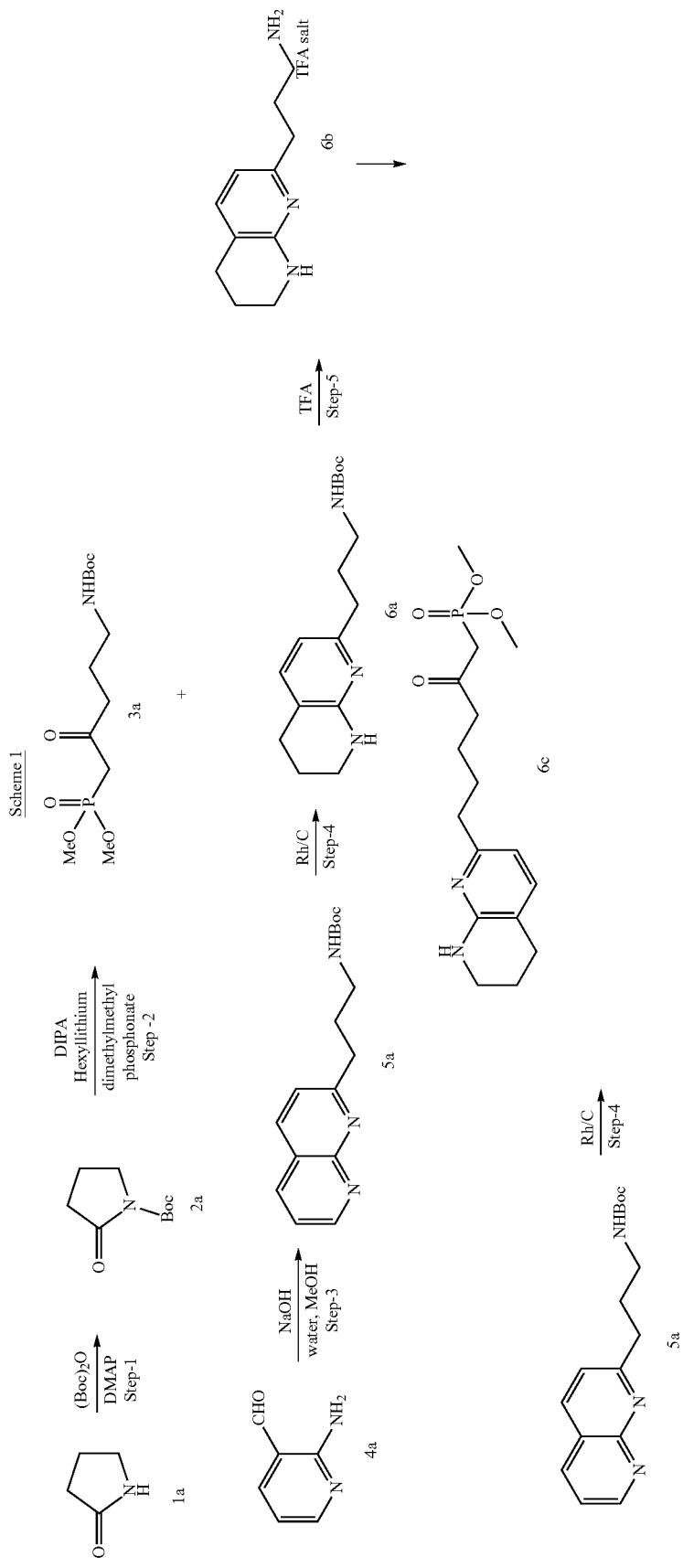

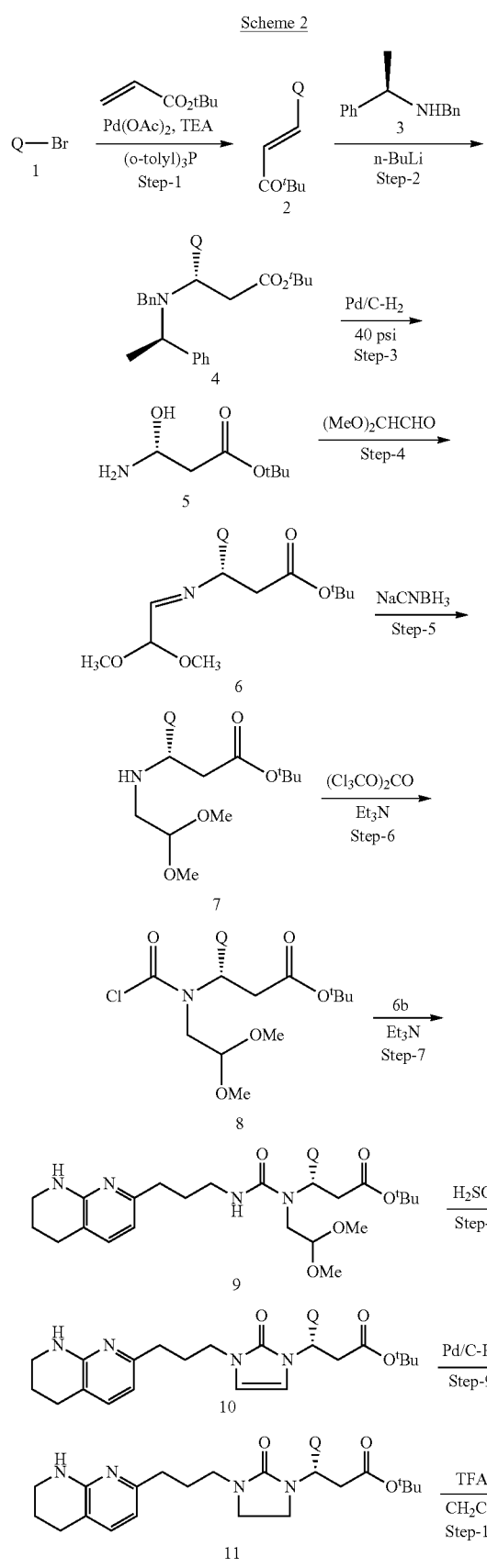
Scheme 2
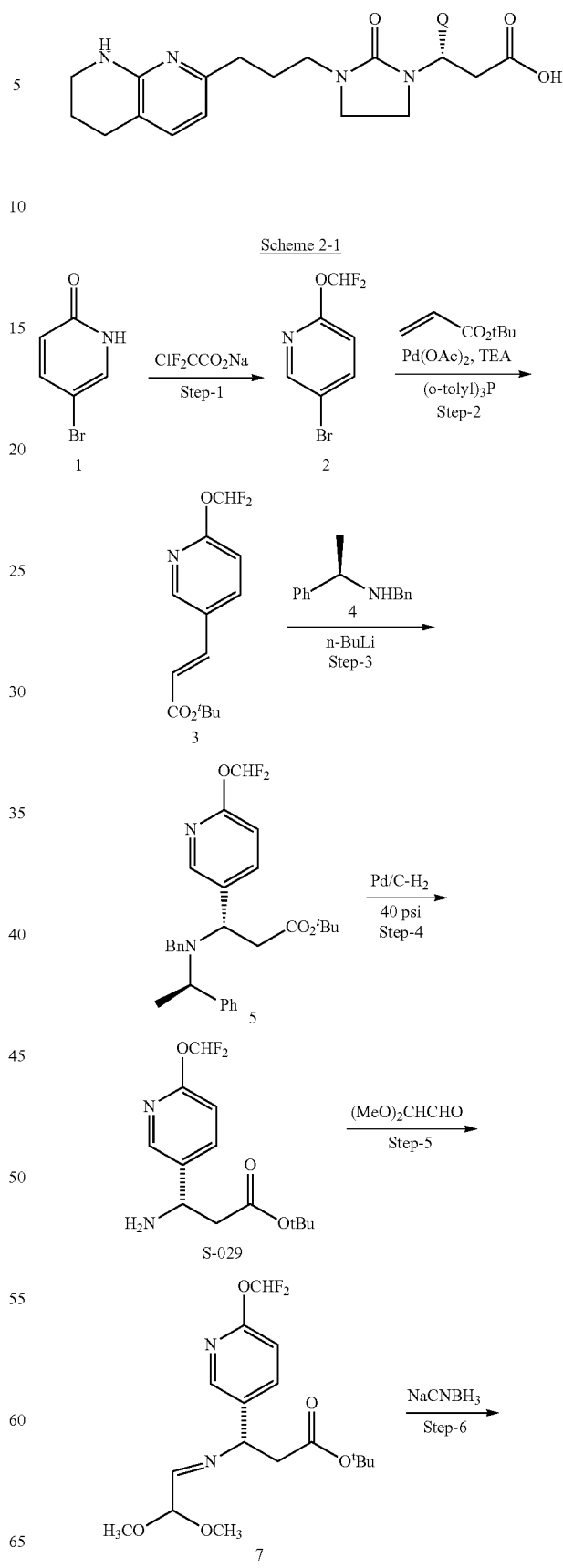
Scheme 2-1

45
-continued
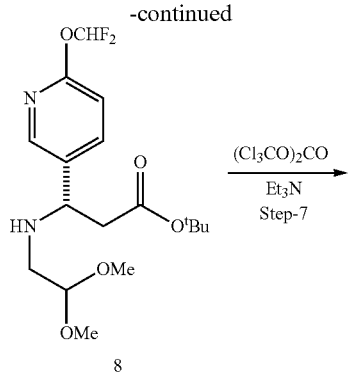
8
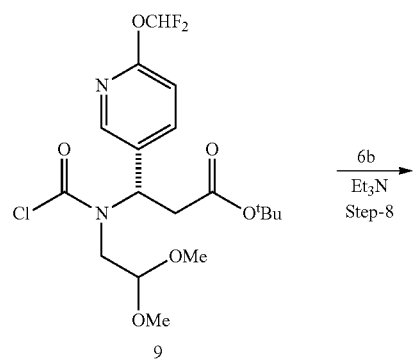
9
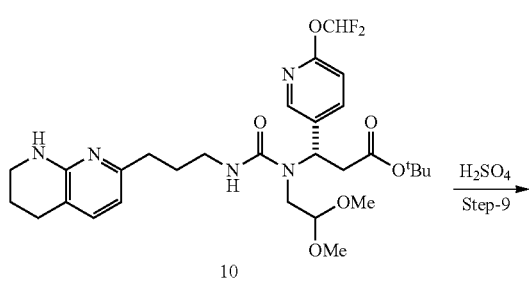
10
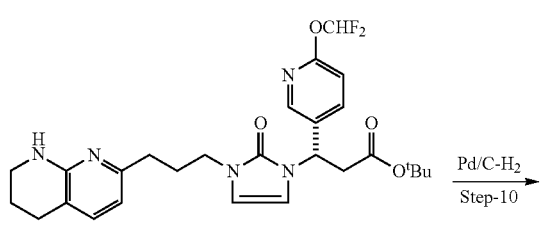
11
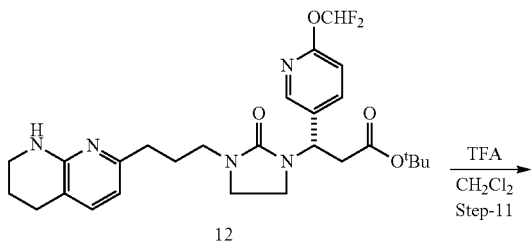
12
46
-continued
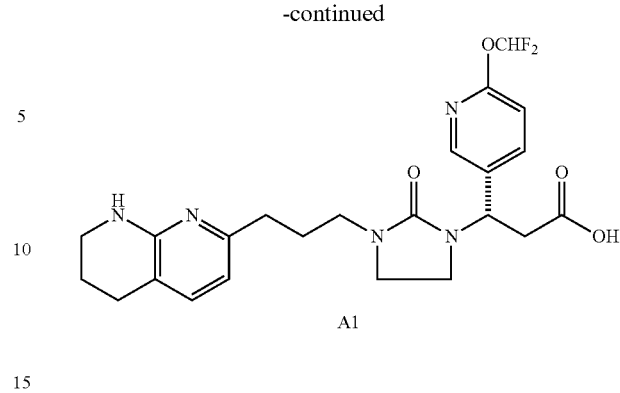
A1
Scheme 3
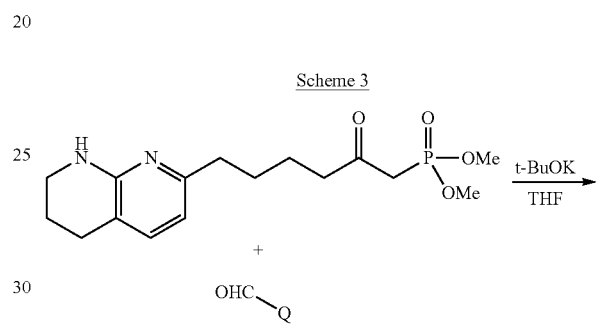
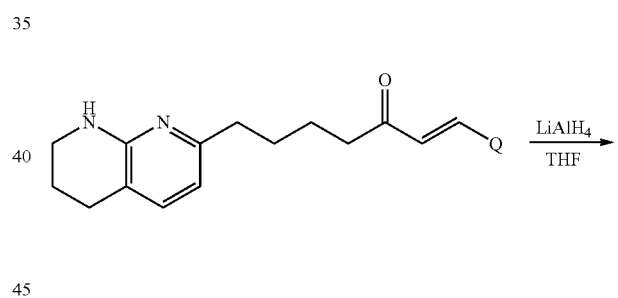
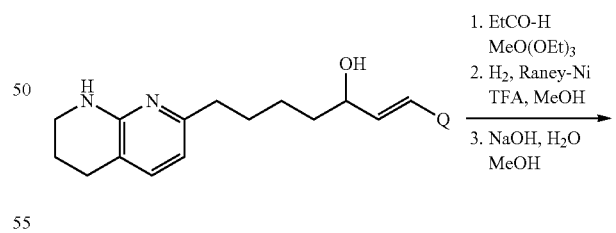
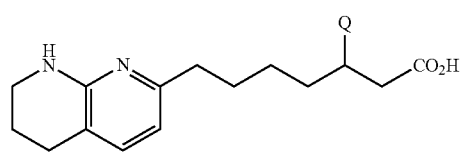

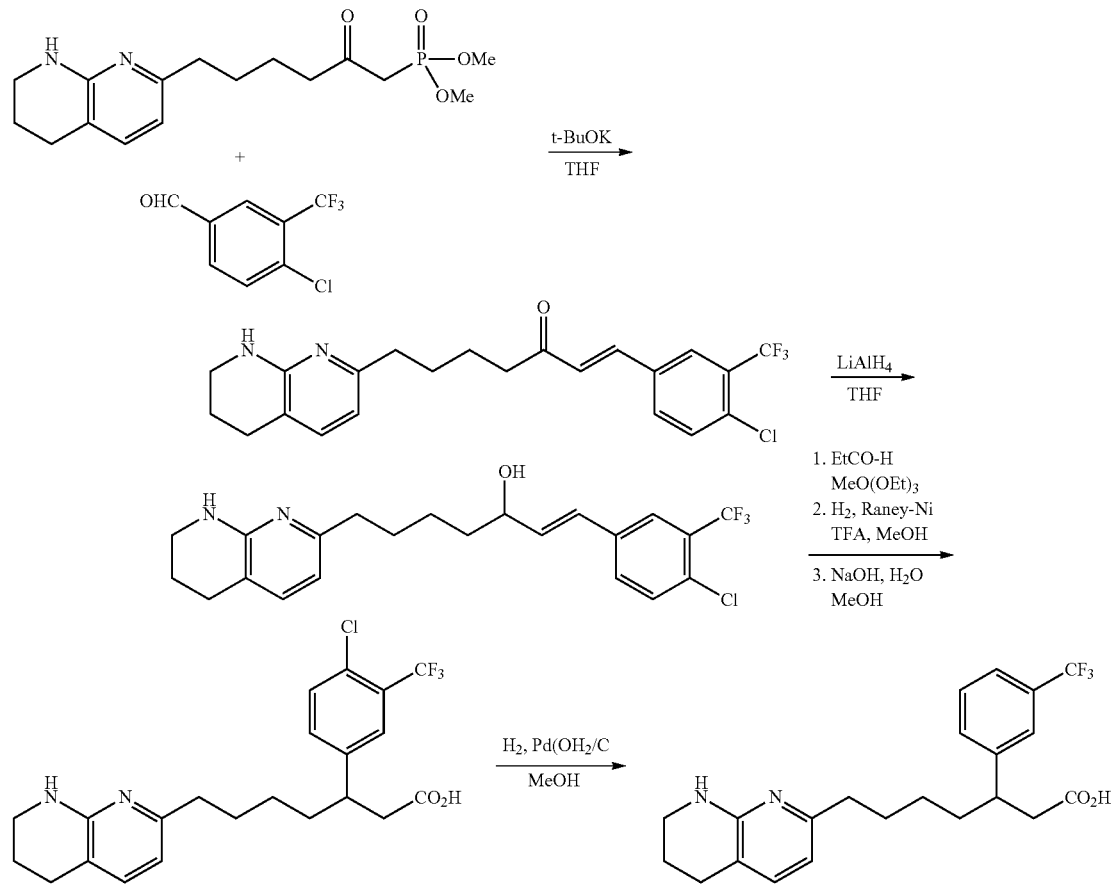
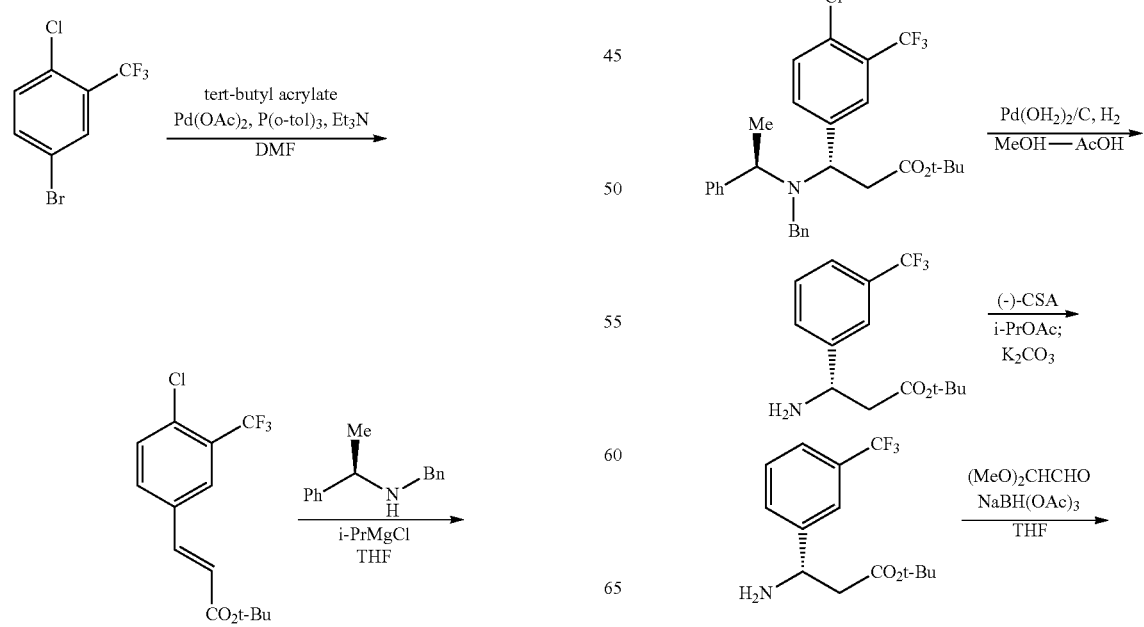

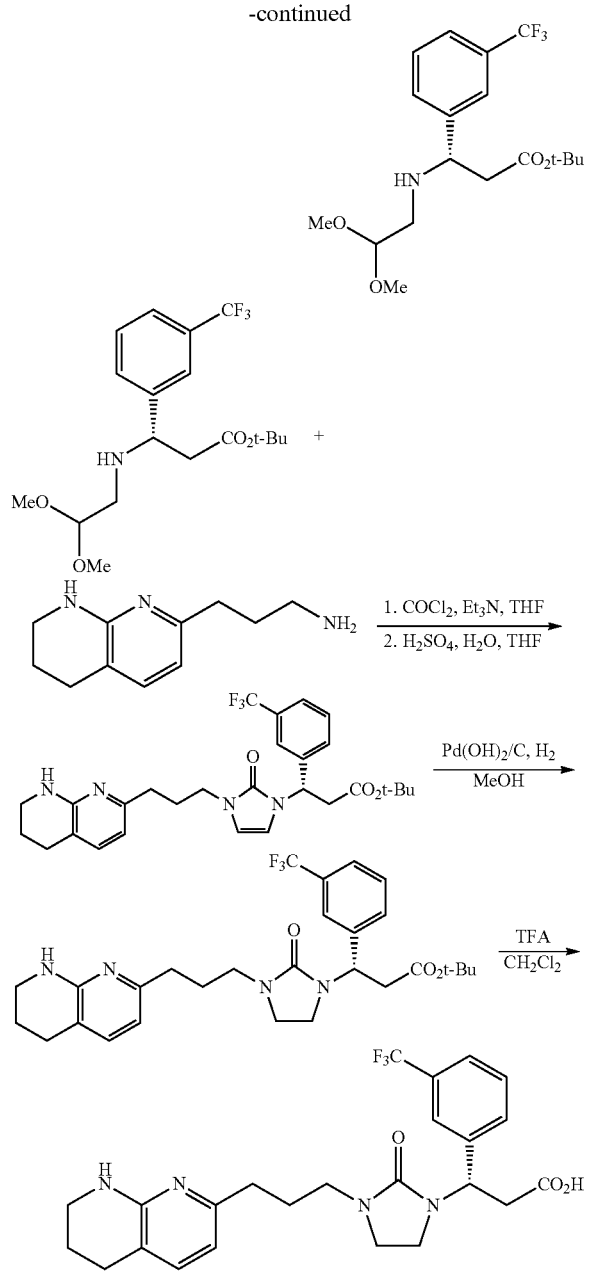

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers. It is intended that all of the possible optical isomers and diastereomers in mixtures and as pure or partially purified compounds are included within the ambit of the invention. The invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as contacting a racemic mixture of compounds with an enantiomerically pure compound to form a diastereomeric mixture, followed by separation of the individual diastereomers by standard methods, such as fractional crystallization or chromatography. The diastereomeric mixture is often a mixture of diastereomeric salts formed by contacting a racemic mixture of compounds with an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which are well known in the art.

Alternatively, any enantiomer of a compound may be obtained by stereoselective synthesis using optically pure starting materials or reagents of known configuration by methods well known in the art.

Some of the compounds of the invention may exist in unsolvated as well as solvated forms such as, for example, hydrates.

"Solvate" means a solvent addition form that contains either a stoichiometric or non-stoichiometric amounts of the solvent molecules. Some compounds have a tendency to trap a fixed molar ratio of the solvent molecules in the crystalline solid state, thus forming a solvate. If the solvent is water, the solvate formed is a hydrate. When the solvent is alcohol, the solvate formed is an alcoholate. Hydrates are formed by the combination of one or more molecules of water with one of the substances (e.g., a compound of the invention) in which the water retains its molecular state as $H_2O$, such combination being able to form one or more hydrate. In hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates include sesquihydrates, monohydrates, dehydrates, and trihydrates. Equally suitable are the hydrates of salts of the compounds of the invention.

For use in medicine, the salts of the compounds of the invention refer to non-toxic "pharmaceutically acceptable salts". Other salts may, however, be useful in the preparation of the compounds of the invention or pharmaceutically acceptable salts thereof. Salts encompassed within the term "pharmaceutically acceptable salts" refer to non-toxic salts of the compounds of the invention which can be prepared by reacting the free base with a suitable organic or inorganic acid. Representative salts include the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamottle (embonate), palmitate, pantothenate, phosphate/diphosphate, polygalacturonate, salicylate, stearate, sulfate, subacetate, succinate, tannate, tartrate, teoclate, tosylate, triethiodide, and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts which may be derived from ammonia or organic amines, such as, for example, diethylamine, triethylamine, ethyldiisopropylamine, procaine, dibenzylamine, N-methylmorpholine, dihydroabietylamine, or methylpiperidine.

The invention includes within its scope prodrugs of the compounds of the invention. In general, such prodrugs will be functional derivatives of the compounds of the invention which are readily convertible in vivo into the required compound. Thus, in the methods of treatment of the invention, the term "administering" shall encompass the treatment of the various disease and conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of the invention into the biological milieu.

The invention also includes one or more metabolites of a compound of the invention.

The present invention also comprehends deuterium labeled compounds of formula I or Ia or the compounds listed in Table 1 and Table 2, wherein a hydrogen atom is replaced by a deuterium atom. The deuterium labeled compounds comprise a deuterium atom having an abundance of deuterium that is substantially greater than the natural abundance of deuterium, e.g., 0.015%.

The term "deuterium enrichment factor" as used herein means the ratio between the deuterium abundance and the natural abundance of a deuterium. In one aspect, a compound of the invention has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Deuterium labeled compounds can be prepared using any of a variety of art-recognized techniques. For example, deuterium labeled compounds of formula I or II or the compounds listed in Table 1 can generally be prepared by carrying out the procedures disclosed in the Schemes and/or Examples described herein, by substituting a readily available deuterium labeled reagent for a non-deuterium labeled reagent.

A compound of the invention or a pharmaceutically acceptable salt or solvate thereof that contains the aforementioned deuterium atom(s) is within the scope of the invention. Further, substitution with deuterium, i.e., $^2$H, can afford certain therapeutic advantages resulting from greater metabolic stability, for example, increased in vivo half-life and/or reduced dosage requirements.

In one aspect, the present invention relates to a method of synthesizing a compound of the invention or a pharmaceutically acceptable salt or solvate thereof.

Biological Assays of the Invention

Cell Adhesion Assays

The ability of compounds of the invention to block cell adhesion to vitronectin and/or fibronectin may be tested with methods or techniques known in the art, for example, the procedure described below.

Adhesion plates preparation: Cell culture plates are coated with vitronectin or fibronectin.

Cell culturing and loading: Exemplary cells (e.g., HMVEC cells, RLMVEC cells, and RAEC cells) are used for the compound testing. Cells are grown and then suspended for testing.

Adhesion assay: Test compounds are added to the cell suspension. After incubation, the cells that do not adhere to vitronectin- or fibronectin-coated plates are removed by gentle washing. The number of the remaining cells is measured. $IC_{50}$ values are calculated.

αV/β6/αVβ8-LAP-TGF β1 Binding Assay

Integrins αVβ6/αVβ8 coupled beads are treated with an αVβ6/αVβ8 ligand (e.g., LAP TGF-β1 (LAP1)), and the complex is incubated with a primary antibody (Ab), which can be labeled for detection (e.g., fluorescently labeled), and optionally with a secondary antibody, which can be labeled for detection (e.g., fluorescently labeled). Reaction between integrin coupled beads and the ligand was considered as the full reaction, and reaction without the ligand or a compound of the disclosure was considered as the blank reaction. The complex is analyzed, e.g., by either plate reader or Flow Cytometer, to determine modulation of binding between αVβ6/αVβ8 and the ligand (e.g., LAP-TGF β1) by the compounds of the present application.

αV/β3/αV/β5-LAP-TGF β1 Binding Assay

Integrins αVβ3/αVβ5 coupled beads are treated with an αVβ3/αVβ5 ligand (e.g., vitronectin), and the complex is treated with a primary antibody (Ab), which can be labeled for detection (e.g., fluorescently labeled), and optionally with a secondary antibody, which can be labeled for detection (e.g., fluorescently labeled). Reaction between integrin coupled beads and the ligand was considered as the full reaction, and reaction without the ligand or a compound of the disclosure was considered as the blank reaction. The complex is analyzed, e.g., by either plate reader or Flow Cytometer, to determine modulation of binding between αVβ3/αVβ5 and the ligand (e.g., vitronectin) by the compounds of the present application.

Anti-Angiogenic Activity Assay

The anti-angiogenic ability of compounds of the invention may be tested with methods or techniques known in the art, for example, the procedure described below.

Chick chorioallantoic membrane (CAM) is grafted with gelatin sponges impregnated with the test compounds and VEGF. Untreated CAM received only VEGF.

Albumin is removed from hen eggs and incubated. Grafts are placed on developing CAMs and further incubated. CAMs are then fixed, dissected and imaged for blood vessel growth.

Distribution in plasma, aqueous humor, vitreous humor, and retina of the compounds of the invention, and the in vivo safety and efficacy of the compounds of the invention may be tested using animals after administration of the compounds to the animals.

Fibrosis can be generally recognized based on the distinct morphology of fibrous tissue in a biopsy of the organ in which fibrosis is suspected. Other means for detecting the presence of fibrosis or developing fibrosis include computerized axial tomography (CAT or CT) scan, ultrasound, magnetic resonance imaging (MRI), and monitoring the level of one or more serum markers known to be indicative of fibrosis (e.g., various types of collagens). The precise manner of diagnosing fibrosis also varies depending on the organ where the fibrotic process takes place. For instance, biopsies are generally effective for diagnosing fibrosis of most organs, whereas endoscopy involving a fiber optic instrument (e.g., a sigmoidoscope or a colonoscope) can be a less traumatic alternative to detect fibrosis of certain organs such as the intestine.

Biopsy for Detecting Fibrosis

Procedures for obtaining biopsy from a given organ or tissue are known, e.g., through exploratory surgery, or a biopsy needle. Upon obtaining a biopsy, the sample is examined and given a score to indicate the presence and level of fibrosis in the sample. Frequently used scoring systems include: the METAVIR scoring system, modified HAI (ISHAK) scoring system, and the Knodell scoring system. The criteria used in scoring are well established and known to those of skilled in the art.

Fibrosis Markers

There are numerous known serum markers whose level can be indicative of the presence and/or severity of fibrosis, including hyaluronic acid, laminin, undulin (type IV collagen) pro-peptides from types I, II, and IV collagens, lysyl oxidase, prolyl hydroxylase, lysyl hydroxylase, PIIINP, PICP, collagen VI, tenascin, collagen XIV, laminin P1, TIMP-1, MMP-2, α2 macroglobulin, haptoglobin, gamma glutamyl transpeptidase, γ globulin, total bilirubin, and apolipoprotein A1.

In Vivo Bleomycin Induced Pulmonary Fibrosis Model.

Experimental animals are randomly and prospectively assigned to groups. On day 0 and prior to bleomycin induction, animals are administered the first dose of vehicle or a compound of the present disclosure. Following dosing, all animals are anesthetized. A small diameter cannula is inserted into the trachea and saline or bleomycin is slowly infused into the lungs. Group 1 serves as an untreated control group and receives saline only (no bleomycin) on day 0. The other groups receive bleomycin on day 0. Treatments with vehicle (e.g., methylcellulose), positive control (e.g., Pirfenidone), or a compound of the present disclosure are administered once or twice daily via oral gavage (PO). All animals are weighed and evaluated daily for respiratory distress.

Prior to sacrifice, animals are anesthetized and once the animal is determined to be non-responsive a shallow incision is made. The trachea is isolated and a transverse cut is made between tracheal rings approximately half-way through the trachea. A tracheotomy is performed by the insertion of a cannula through the incision secured with surgical suture to the trachea. Following cannulation, the adapter end of the cannula is attached to the mechanical ventilator. The animal is ventilated and following an acclimation period, lung volume is standardized and each animal undergoes a measure of total respiratory impedance.

Pharmaceutical Compositions of the Invention

The present invention relates to pharmaceutical compositions comprising a compound of the invention as an active ingredient. In one aspect, the invention provides a pharmaceutical composition comprising at least one compound of formula I, or a pharmaceutically acceptable salt or solvate thereof and one or more pharmaceutically acceptable carriers or excipients. In one aspect, the invention provides a pharmaceutical composition comprising at least one compound of formula II, IIIa, IIIb, IVa, or IVb, or a pharmaceutically acceptable salt or solvate thereof and one or more pharmaceutically acceptable carriers or excipients. In one aspect, the invention provides a pharmaceutical composition comprising at least one compound selected from Table 1.

As used herein, the term "composition" is intended to encompass a product comprising the specified ingredients in the specified amounts, as well as any product which results, directly or indirectly, from combination of the specified ingredients in the specified amounts.

The compounds of the invention can be formulated for oral administration in forms such as tablets, capsules (each of which includes sustained release or timed release formulations), pills, powders, granules, elixirs, tinctures, suspensions, syrups and emulsions. The compounds of the invention can also be formulated for intravenous (bolus or in-fusion), intraperitoneal, topical (e.g., ocular eye-drop), subcutaneous, intramuscular or transdermal (e.g., patch) administration, all using forms well known to those of ordinary skill in the pharmaceutical arts. For example, compounds of the invention for the treatment of macular degeneration, DR, DME, or macular edema following RVO, are formulated for topical administration, for example, in the form of eye-drops.

For topical ocular administration, the compositions are provided as ophthalmic formulation comprising a compound of the present invention in concentration between about 0.01 and about 5 weight percent, preferably between about 0.1 and about 5.0 weight percent, more preferably between about 0.5 and about 5.0 weight percent, and most preferably between about 0.8 and about 3.0 weight percent.

The ophthalmic formulation of the present invention may be in the form of an aqueous solution comprising an aqueous vehicle.

The aqueous vehicle component of the ophthalmic formulation may comprise water and at least one ophthalmically acceptable excipient. Preferably, the aqueous vehicle comprises a solution of the one or more ophthalmically acceptable excipients in water.

Suitable ophthalmically acceptable excipients include those selected from the group consisting of a solubility enhancing agent, chelating agent, preservative, tonicity agent, viscosity/suspending agent, buffer, and pH modifying agent, and a mixture thereof. Preferably, the ophthalmically acceptable excipient is selected from the group consisting of a solubility enhancing agent, chelating agent, preservative, tonicity agent, viscosity/suspending agent, and pH modifying agent, and a mixture thereof.

Any suitable ophthalmically acceptable solubility enhancing agent can be used. Examples of a solubility enhancing agent include cyclodextrin, such as those selected from the group consisting of hydroxypropyl-β-cyclodextrin, methyl-β-cyclodextrin, randomly methylated-3-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S-(3-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof. Preferably, solubility enhancing agent includes β-cyclodextrin sulfobutyl ether, hyrdoxypropyl-β-cyclodextrin, sulphated β-cyclodextrin (S-β-CD), and maltosyl-β-cyclodextrin, and mixtures thereof. β-cyclodextrin sulfobutyl ether is a particularly preferred solubility enhancing agent. The solubility enhancing agent(s) may be added in an amount of about 1 to about 20 wt %, preferably about 1 to about 10 wt %, and more preferably about 5 to about 10 wt %.

Any suitable ophthalmically acceptable chelating agent can be used. Examples of a suitable ophthalmically acceptable chelating agent include those selected from the group consisting of ethylenediaminetetraacetic acid and metal salts thereof, disodium edetate, trisodium edetate, and tetrasodium edetate, and mixtures thereof. Disodium edetate is a particularly preferred chelating agent. The chelating agent(s) may be added in an amount of about 0.001 to about 0.05 wt %, preferably about 0.001 to about 0.02 wt %, more preferably about 0.002 to about 0.01 wt %, and most preferably about 0.002 to about 0.005 wt %.

Preferably, the aqueous vehicle includes a preservative. Preferred preservatives include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, sorbic acid, and mixtures thereof. More preferably, the preservative is a quaternary ammonium salt such as benzalkonium halides (preferably benzalkoniurn chloride), chlorhexidine gluconate, benzethonium chloride, cetyl pyridinium chloride, potassium sorbate, sodium benzoate, ethyl p-hydroxybenzoate, butyl p-hydroxybenzoate, or propylaminopropyl biguanide, or mixtures thereof. Propylaminopropyl biguanide is an especially preferred preservative. The preservative(s) may be used in an amount of about 0.00001 to about 0.0001 wt %, preferably about 0.00001 to about 0.00008 wt %, and more preferably about 0.00002 to about 0.00005 wt %.

The aqueous vehicle may also include a tonicity agent to adjust the tonicity (osmotic pressure) in order to achieve an ophthalmically compatible formulation. The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof. Preferably, the tonicity agent is selected from the group consisting of glycerin, mannitol, potassium chloride, and sodium chloride. More preferably mannitol and/or sodium chloride (and most preferably a mixture thereof) are employed. The tonicity agent(s) may be used in an amount of about 0.05 to about 8 wt %, preferably about 0.1 to about 6 wt %, more preferably about 0.1 to about 4 wt %, and most preferably about 0.2 to about 4 wt %.

When a mixture of mannitol and sodium chloride is used as tonicity agents, preferably the weight ratio of mannitol: sodium chloride is about 4:1 to about 15:1, more preferably about 6:1 to about 14:1, or 8:1 to about 14:1 and particularly about 10:1 to about 12:1. If mannitol alone is used as the tonicity agent, it is preferably used in an concentration of about 4.5 to about 6.5 wt %, and more preferably in a concentration of about 5.0 to about 5.5 wt %. If sodium chloride alone is used as the tonicity agent, it is used in a concentration of about 0.05 to about 8 wt %, preferably about 0.1 to about 6 wt %, more preferably about 0.1 to about 4 wt %, and most preferably about 0.2 to about 4 wt %.

The aqueous vehicle preferably also contains a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof. In preferred embodiments of the present invention, the viscosity/suspending agent is a carbomer, more preferably Carbopol 974P. The viscosity/suspending agent(s) may be present in an amount of about 0.05 to about 2 wt %, preferably 0.1 to about 1 wt %, more preferably about 0.2 to about 0.8 wt %, and most preferably about 0.3 to about 0.5 wt %.

In order to adjust the formulation to an ophthalmically acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target ophthalmically acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof. The buffer agent(s) may be present in an amount of about 0.05 to about 5 wt %, preferably 0.1 to about 5 wt %, more preferably about 0.2 to about 5 wt %, and most preferably about 0.5 to about 5 wt %.

The ophthalmic formulation for topical administration to the eye may further comprise a wetting agent. In any embodiment of the present invention the wetting agent is preferably a nonionic wetting agent. More preferably, the wetting agent is water soluble or swellable. Most preferably the wetting agent is water soluble. "Water soluble" is to be understood in the manner used in standard texts such as the "Handbook of Pharmaceutical Excipients" (Raymond C Rowe, Paul J Sheskey and Sian C Owen, Fifth Edition, Pharmaceutical Press and American Pharmacists Association 2006). Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Specific examples of suitable wetting agents include those selected from the group consisting of: polyoxyethylene-polyoxypropylene block copolymers (poloxamers) such as: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127], polyoxyethylene (20) polyoxypropylene

(20) glycol [Pluronic L44], polyoxyethylenated sorbitan esters (polysorbates) such as poly(oxyethylene)sorbitan monopalmitate (polysorbate 40), poly(oxyethylene)sorbitan monostearate (polysorbate 60), poly(oxyethylene)sorbitan tri stearate (polysorbate 65), poly(oxyethylene) sorbitan monooleate (polysorbate 80), poly(oxyethylene) sorbitan monolaurate, poly(oxyethylene) sorbitan trioleate, polyethoxylated ethers of castor oils such as polyoxyethylene hydrogenated castor oil 10, polyoxyethylene hydrogenated castor oil 40, polyoxyethylene hydrogenated castor oil 50 and polyoxyethylene hydrogenated castor oil 60, polyoxyl 40 stearate, sucrose fatty esters, and polyoxyethylene fatty esters, and mixtures thereof.

Preferably, the wetting agent is selected from the group consisting of: polyoxyethylene-polyoxypropylene block copolymers (poloxamers) such as: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127], and polyoxyethylene (20) polyoxypropylene (20) glycol [Pluronic L44], polyoxyethylenated sorbitan esters (polysorbates) such as poly(oxyethylene)sorbitan monopalmitate (polysorbate 40), poly(oxyethylene)sorbitan monosteaxate (polysorbate 60), poly(oxyethylene)sorbitan tri stearate (polysorbate 65), poly (oxyethylene) sorbitan monooleate (polysorbate 80), poly (oxyethylene) sorbitan monolaurate, and poly(oxyethylene) sorbitan trioleate and mixtures thereof.

More preferably, the wetting agent is a polyoxyethylene-polyoxypropylene block copolymer (poloxamer). Examples of suitable poloxamers include: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127] and polyoxyethylene (20) polyoxypropylene (20) glycol [Pluronic L44] or a mixture thereof.

Further preferred are wetting agents selected from the group consisting of polyoxyethylene (42) polyoxypropylene (67) glycol [Pluronic PI 23], polyoxyethylene (54) polyoxypropylene (39) glycol [Pluronic P85], polyoxyethylene (196) polyoxypropylene (67) glycol [Poloxamer 407, Pluronic F127] and mixtures thereof.

An especially preferred wetting agent is polyoxyethylene (196) polyoxypropylene (67) glycol [Poloxamer 407, Pluronic F127].

Particularly preferred formulations for topical administration to the eye of the present invention comprise a compound of the present invention, a solubility enhancing agent, a cheating agent, a preservative, a tonicity agent, a viscosity/suspending agent, a buffer, and a pH modifying agent. More particularly preferred formulations are comprised of an aqueous solution of a β-cyclodextrin, a borate salt, boric acid, sodium chloride, disodium edetate, and propylaminopropyl biguanide.

In one aspect, the ophthalmic formulation of the present invention is in the form of a solution, such as one of the following:

| Solution Composition | | |
|---|---|---|
| a compound of the invention | 0.1-5.0 | g |
| a solubility enhancing agent | 1-20 | g |
| a buffering agent | 0.05-5.0 | g |
| an tonicity agent | 0.05-8 | g |
| a chelating agent | 1-50 | mg |
| a preservative | 0.01-0.1 | mg |
| water | 100 | ml |
| a compound of the invention | 0.8-3.0 | g |
| a solubility enhancing agent | 5-10 | g |
| a buffering agent | 0.5-5.0 | g |
| an tonicity agent | 0.2-4 | g |
| a chelating agent | 2-5 | mg |
| a preservative | 0.02-0.05 | mg |
| water | 100 | ml |

| Solution Composition | I | II | III | IV |
|---|---|---|---|---|
| a compound of the invention | 2.5 g | 2.0 g | 1.5 g | 1.0 g |
| a solubility enhancing agent | 10 g | 10 g | 10 g | 5 g |
| buffering agent 1 | 1.05 g | 1.05 g | 1.05 g | 1.05 g |
| buffering agent 2 | 0.285 g | 0.285 g | 0.285 g | 0.285 g |
| an tonicity agent | 0.25 g | 0.25 g | 0.25 g | 0.25 g |
| a chelating agent | 2.5 mg | 2.5 mg | 2.5 mg | 2.5 mg |
| a preservative | 0.03 mg | 0.03 mg | 0.03 mg | 0.03 mg |
| water | 100 ml | 100 ml | 100 ml | 100 ml |

The ophthalmic formulation of the present invention may also be in the form of a gel or a semi-gel, or both; a jelly; a suspension; an emulsion; an oil; an ointment; a cream; or a spray.

The ophthalmic gel, semi-gel, jelly, suspension, emulsion, oil, ointment, cream, or spray may contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and propylene glycol, salts such as sodium chloride), preservatives or antiseptics (e.g., benzalkonium chloride, benzalkonium chloride, P-oxybenzoates such as methyl p-oxybenzoate or ethyl p-oxybenzoate, benzyl alcohol, phenethyl alcohol, sorbic acid or its salt, thimerosal, chlorobutanol and the like), solubilizing enhancing agents (e.g., cyclodextrins and their derivative, water-soluble polymers such as polyvinyl pyrrolidone, surfactants such as tyloxapol, polysorbates), pH modifiers (e.g., hydrochloric acid, acetic acid, phosphoric acid, sodium hydroxide, potassium hydroxide, ammonium hydroxide and the like), thickening agents (e.g., HEC, hydroxypropyl cellulose, methyl cellulose, HPMC, carboxymethyl cellulose and their salts), chelating agents (e.g., sodium edetate, sodium citrate, condensed sodium phosphate) and the like. Each of these additives may be in the amount or concentration similar to those described for the ophthalmic formulation in the form of a solution above.

Furthermore the compounds of the invention may be formulated for topical administration by incorporation into novel ophthamlic formulations including but not limited to: microemulsions, liposomes, niosomes, gels, hydrogel, nanoparticles, and nanosuspension.

1. Microemulsions

Microemulsions are dispersion of water and oil facilitated by a combination of surfactant and cosurfactant in a manner to reduce interfacial tension. These systems are usually characterized by higher thermodynamic stability, small droplet size (approximately 100 nm) and clear appearance. Their transparent appearance is due to the high level of dispersion of the internal phase, and the size of it ranges from 100-1000 angstroms. Processes for forming microemulsions suitable for use in ophthalmic formulations are described in Vandamne, T. F. *Prog Retinal Eye Res* 2002; 21:15-34, which is incorporated by reference.

2. Liposomes

Liposomes are lipid vesicles containing aqueous core and have been widely exploited in ocular delivery for various drug substances. Depending on the nature of the lipid composition selected, liposomes can provide extended release of the drug.

3. Niosomes

Niosomes are bilayered structural vesicles made up of nonionic surfactant and are capable of encapsulating both lipophilic and hydrophilic compounds. They can release the drug independent of pH and enhance ocular bioavailability. Niosomes are microscopic lamellar structures that are formed on the admixture of nonionic surfactant of the alkyl or dialkyl polyglycerol ether class and cholesterol with subsequent hydration in aqueous media. Structurally niosomes are similar to liposomes, in that they are also made up of a bilayer. However, the bilayer in the case of nisomes is made up of nonionic surface-active agents rather than phospholipids as in the case of liposomes. Niosomes may be unilamellar or multilamellar depending on the method used to prepare them. They are capable of entrapping hydrophilic and hydrophobic solutes. They possess great stability and lack many disadvantages associate with liposomes such as high cost and the variable purity of phospholipids. The properties of niosomes and process for preparing them are well known in the art, see e.g., Wagh, V. D. et al., *J Pharm Res* 2010; 3(7):1558-1563; Kaur, H. et al., *Int J Pharm Sci Rev Res* 2012; 15(1):113-120, each of which is incorporated by reference.

4. Gels

Ophthalmic gels are composed of mucoadhesive polymers that provide localized delivery of an active ingredient to the eye. Such polymers have a property known as bioadhesion, meaning attachment of a drug carrier to a specific biological tissue. These polymers are able to extend the contact time of the drug with the biological tissues and thereby improve ocular bioavailability. The choice of the polymer plays a critical role in the release kinetics of the drug from the dosage form. Several bioadhesive polymers are available with varying degree of mucoadhesive performance. Some examples are carboxymethylcellulose, carbopol, polycarbophil, and sodium alginate. The use of gel formulations in ocular drug deliver has been reviewed in Ali, Y. et al., *Adv Drug Deliv Rev* 2006; 58: 1258-1268, which is incorporated by reference.

5. Hydrogels

Hydrogels are three-dimensional, hydrophilic, polymeric networks capable of taking in large amounts of water or biological fluids. Residence time can be significantly enhanced with a hydrogel formulation. The gelation can be obtained by changing temperature and pH. Poloxamers, the most widely used polymer, contains the hydrophobic part in the center surrounded by a hydrophilic part. Though they are widely employed to enhance the residence time. Recent perspectives in the use of hydrogels in ocular drug deliver are described by Gaudana, R., Jwala, J., Boddu, S. H. S., Mitra, A. K. *Pharm Res.* 2009; 26(5):1197-1216 which is incorporated by reference.

6. Nanoparticles

Nanoparticles are defined as particles with a diameter of less than 1 μm, comprising of various biodegradable or non biodegradable polymers, lipids, phospholipids or metals. They can be classified as nanospheres or nanocapsules depending upon whether the drug has been uniformly dispersed or coated within polymeric material. The uptake and distribution of nanoparticles is dependent on their size. The use of nanoparticles in ocular drug delivery has recently been reviewed by Hing et al., *Int. J. Ophthalmol* 2013; 6:390-396, which is incorporated by reference.

7. Nanosuspensions

Nanosuspensions are defined as sub-micron colloidal systems that consist of poorly water soluble drugs suspended in an appropriate dispersion medium stabilized by surfactants. Usually, nanosuspensions consist of colloidal carriers like polymeric resins which are inert in nature. Nanosuspensions enhance drug solubility and thus bioavailability. Unlike microemulsions, nanosuspensions are non-irritant. Charge on the surface of nanoparticles facilitates their adhesion to the cornea. The use of nanosuspensions in drug delivery is reviewed in Rabinow, *Nature Rev Drug Disc* 2004; 785-796, which is incorporated by reference.

The compounds of the present invention can also be administered in the form of a formulation suitable for ocular topical delivery. Detailed descriptions of formulation suitable for ocular topical delivery are described in Bartlett, J. D. and Jaanus, S. D., *Clinical Ocular Pharmacology,* 2008, Elsevier Health Sciences, which is incorporated by reference.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, and polyethyleneoxide-polylysine substituted with palmitoyl residues. Furthermore, the compounds of the invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The present invention also provides a pharmaceutical composition comprising a compound of the invention or a pharmaceutically acceptable salt or solvate thereof, and a pharmaceutically acceptable carrier or excipient, and further an active ingredient selected from the group consisting of a) an antagonist of integrin α5β1, b) a cytotoxic/antiproliferative agent, c) an inhibitor of epidermal-derived, fibroblast-derived, or platelet-derived growth factor, d) an inhibitor of VEGF, e) an inhibitor of Flk-1/KDR, Flt-1, Tck/Tie-2, or Tic-1, and f) an inhibitor of phosphoinositide 3-kinase, and a mixture thereof.

The present invention further provides a pharmaceutical composition comprising a compound of the invention or a pharmaceutically acceptable salt or solvate thereof, and a pharmaceutically acceptable carrier or excipient, and further an active ingredient selected from the group consisting of a) an antagonist of integrin α5β1, b) a cytotoxic/antiproliferative agent, c) an inhibitor of epidermal-derived, fibroblast-derived, or platelet-derived growth factors, d) an inhibitor of VEGF, and e) an inhibitor of phosphoinositide 3-kinase, and a mixture thereof.

Nonlimiting examples of antagonists of integrin α5β1 are (S)-2-((R)-2-((S)-2-((S)-2-((S)-1-acetylpyrrolidine-2-carboxamido)-3-(1H-imidazol-5-yl)propanamido)-3-hydroxypropanamido)-3-mercaptopropanamido)succinamide, and JSM6427, described in Stragies, R. et al., *J. Med. Chem.* 2007, 50:3786-3794, herein incorporated by reference.

Nonlimiting examples of cytotoxic/antiproliferative agents are taxol, vincristine, vinblastine, and doxorubicin.

Nonlimiting examples of inhibitors of epidermal-derived, fibroblast-derived, or platelet-derived growth factors are pazopanib, and sunitinib, Nonlimiting examples of inhibitors of vascular endothelial derived growth factor (VEGF) are bevacizumab and ranibizumab, Nonlimiting examples of inhibitors of phosphoinositide 3-kinase are indelalisib and 2-morpholin-4-yl-8-phenylchroman-4-one.

Methods of Use

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

Fibrosis of organs or tissues is involved in various diseases or disorders, such as (1) renal diseases (e.g., tubulointerstitial nephritis), (2) respiratory diseases (e.g., interstitial pneumonia (pulmonary fibrosis)), (3) gastrointestinal diseases (e.g., hepatocirrhosis, chronic pancreatitis and scirrhous gastric cancer), (4) cardiovascular diseases (myocardial fibrosis), (5) bone and articular diseases (e.g., bone marrow fibrosis and rheumatoid arthritis), (6) skin diseases (e.g., post surgical scar, burn scar, keloid, hypertrophic scar and scleroderma), (7) obstetric diseases (e.g., hysteromyoma), (8) urologic diseases (prostatic hypertrophy), (9) other diseases (e.g., Alzheimer's disease, sclerosing peritonitis, type I diabetes and post surgical adhesion). Accordingly, the tissue fibrosis may be cardiac fibrosis, scleroderma, skeletal muscle fibrosis, hepatic fibrosis, kidney fibrosis, pulmonary fibrosis, intestinal fibrosis, or diabetic fibrosis. For example, a fibrosis may be ongenital hepatic fibrosis (CHF); renal tubulointerstitial fibrosis; pulmonary fibrosis associated with an autoimmune disorder (e.g. rheumatoid arthritis, lupus and sarcoidosis); interstitial fibrosis associated with diabetic cardiomyopathy; skeletal muscle fibrosis associated with muscular dystrophies (e.g., Becker muscular dystrophy and Duchenne muscular dystrophy), denervation atrophies, neuromuscular diseases (e.g., acute polyneuritis, poliomyelitis, Werdig/Hoffman disease, amyotrophic lateral sclerosis, progressive bulbar atrophy disease), Mediastinal fibrosis (soft tissue of the mediastinum), myelofibrosis (bone marrow), retroperitoneal fibrosis (soft tissue of the retroperitoneum), progressive massive fibrosis (lungs), nephrogenic systemic fibrosis (skin), Crohn's Disease (intestine), Keloid (skin), scleroderma/systemic sclerosis (skin, lungs), arthrofibrosis (knee, shoulder, other joints), Peyronie's disease (penis), dupuytren's contracture (hands or fingers), Some forms of adhesive capsulitis (shoulder).

"Hepatic fibrosis" or "fibrosis of the liver" is the excessive accumulation of extracellular matrix proteins including collagen that occurs in most types of chronic liver diseases. Advanced liver fibrosis results in cirrhosis, liver failure, and portal hypertension and often requires liver transplantation. Activated hepatic stellate cells, portal fibroblasts, and myofibroblasts of bone marrow origin have been identified as major collagen-producing cells in the injured liver. These cells are activated by fibrogenic cytokines such as TGF-β1, angiotensin II, and leptin. The main causes of liver fibrosis in industrialized countries include chronic alcohol abuse, nonalcoholic steatohepatitis (NASH), iron and copper overload, alcohol-induced liver injury, chronic infection of hepatitis C, B, and D, hemochromatosis, secondary biliary cirrhosis, NASH, and autoimmune hepatitis.

"Pulmonary fibrosis" or "fibrosis of the lung" is a respiratory disease in which scars are formed in the lung tissues, leading to serious breathing problems. The accumulation of excess fibrous connective tissue leads to thickening of the walls, and causes reduced oxygen supply in the blood. As a consequence patients suffer from perpetual shortness of breath. Pulmonary fibrosis may be a secondary effect of other diseases. Most of these are classified as interstitial lung diseases. Examples include autoimmune disorders, viral infections and bacterial infection like tuberculosis which may cause fibrotic changes in both lungs upper or lower lobes and other microscopic injuries to the lung. Idiopathic pulmonary fibrosis can also appear without any known cause. Diseases and conditions that may cause pulmonary fibrosis as a secondary effect include: inhalation of environmental and occupational pollutants, hypersensitivity pneumonitis, cigarette smoking, some typical connective tissue diseases (such as rheumatoid arthritis, SLE and scleroderma), other diseases that involve connective tissue (such as sarcoidosis and Wegener's granulomatosis), infections, and certain medications (e.g., amiodarone, bleomycin (pingyangmycin), busulfan, methotrexate, apomorphine, and nitrofurantoin).

"Cardiac fibrosis" or "fibrosis of the heart" may refer to an abnormal thickening of the heart valves due to inappropriate proliferation of cardiac fibroblasts, but more commonly refers to the proliferation of fibroblasts in the cardiac muscle. Fibrotic cardiac muscle is stiffer and less compliant and is seen in the progression to heart failure. Fibrocyte cells normally secrete collagen, and function to provide structural support for the heart. When over-activated this process causes thickening and fibrosis of the valve, with white tissue building up primarily on the tricuspid valve, but also occurring on the pulmonary valve. The thickening and loss of flexibility eventually may lead to valvular dysfunction and right-sided heart failure.

"Renal fibrosis" or "fibrosis of the kidney", characterized by glomerulosclerosis and tubulointerstitial fibrosis, is the final common manifestation of a wide variety of chronic kidney diseases (CKD). Progressive CKD often results in widespread tissue scarring that leads to the complete destruction of kidney parenchyma and end-stage renal failure.

Cystic fibrosis (CF) is a genetic disorder that affects mostly the lungs but also the pancreas, liver, kidneys and intestine. Patients experience symptoms including difficulty breathing and coughing up sputum as a result of frequent lung infections. CF is an autosomal recessive disorder, caused by mutations in both copies of the gene for the protein cystic fibrosis transmembrane conductance regulator (CFTR). CFTR is involved in production of sweat, digestive fluids, and mucus.

A compound of formula Ia modulates (e.g., inhibits the activity of, decreases the expression of, and/or increases the degradation of) a factor (e.g., collagen, TGF-β1) that is involved in the regulation of the fibrosis process. For example, a compound of formula Ia is capable of reducing collagen synthesis. In another example, a compound of formula Ia can decrease the production of fibrogenic cytokines (e.g., TGF-β1). In another example, a compound of formula Ia can reduce the accumulation of extracellular matrix protein. In yet another example, a compound of formula Ia can inhibit the proliferation of fibroblast cells.

In another example, a compound of formula Ia may inhibit processes mediated by αv integrins. Inhibition and blockade of αvβ6 and/or αvβ8 result in a phenotype similar to all of the development effects of loss of TGF-β1 and TGF-β3, suggesting that these integrins are required for most or all important roles of these TGF-β isoforms in development of fibrosis. Antagonists of the integrins αvβ6 and/or αvβ8 are thus useful for treating and preventing fibrotic activity. For example, TGF-β activation by the αvβ6 integrin has been shown to play an important role in models of fibrosis in the lungs, biliary tract, and kidney (Henderson et al., Nat Med 19, 617 (2013)). The αvβ6 integrin has further been shown to be overexpressed in human kidney epithelium in membranous glomerulonephritis, diabetes mellitus, IgA nephropathy, Goodpasture's syndrome, and Alport syndrome renal epithelium (*Am. Journal of Pathology,* 2007). In one aspect, a compound of formula Ia treats or prevents fibrosis by inhibiting αvβ6 and/or αvβ8.

Over expression of the αvβ6 integrin has also been shown to play a role in certain cancers, including but not limited to colorectal carcinomas, thyroid carcinomas, cervical squamous cell carcinomas, and certain breast carcinomas. Over expression of the αvβ8 integrin has been associated with a variety of Th17-drive autoimmune diseases, including psoriasis, multiple sclerosis, rheumatoid arthritis, and inflammatory bowel disease. A number of integrin receptors have also been shown to play a role in foot and mouth disease virus (FMDV).

Thus, in one aspect, the present invention provides a method of treating or preventing a fibrosis, comprising administering to a subject in need thereof a therapeutically effective amount of a compound of formula Ia or a pharmaceutically acceptable salt or solvate thereof or a therapeutically effective amount of a pharmaceutical composition of the invention. In one aspect, the invention provides treating a fibrosis. In one aspect, the invention provides preventing a fibrosis.

In another aspect, the present invention also provides the use of a compound of formula Ia or a pharmaceutically acceptable salt or solvate thereof in the manufacture of a medicament for the treatment or prevention of a fibrosis in a subject. The present invention also provides the use of a compound of formula Ia or a pharmaceutically acceptable salt or solvate thereof in treating or preventing a fibrosis in a subject.

In one aspect, the fibrosis is fibrosis of the liver, kidney, intestine, lung, or heart. In a further aspect, the fibrosis is involved in various diseases or disorders, such as (1) renal diseases (e.g., tubulointerstitial nephritis), (2) respiratory diseases (e.g., interstitial pneumonia (pulmonary fibrosis)), (3) gastrointestinal diseases (e.g., hepatocirrhosis, chronic pancreatitis and scirrhous gastric cancer), (4) cardiovascular diseases (myocardial fibrosis), (5) bone and articular diseases (e.g., bone marrow fibrosis and rheumatoid arthritis), (6) skin diseases (e.g., post surgical scar, burn scar, keloid, hypertrophic scar and scleroderma), (7) obstetric diseases (e.g., hysteromyoma), (8) urologic diseases (prostatic hypertrophy), (9) other diseases (e.g., Alzheimer's disease, sclerosing peritonitis, type I diabetes and post surgical adhesion).

Diabetic retinopathy, a closely related condition, is the result of microvascular retinal changes. Hyperglycemia-induced intramural pericyte death and thickening of the basement membrane lead to incompetence of the vascular walls in the retina, which affects the blood-retinal barrier and makes the retinal blood vessels more permeable. Damaged blood vessels leak fluid and lipids onto the macula, the part of the retina that provides us with detailed vision, causing the macula to swell. Eventually this can progress to develop a condition called macular edema.

Accordingly, AMD, DR, DME, and macular edema following central retinal vein occlusion (thrombosis) can be treated or prevented through administration (e.g., topical administration) of the compounds or pharmaceutical compositions of the present invention.

The present invention provides a method of treating or preventing a disease or condition in a subject, comprising administering to a subject in need thereof a therapeutically effective amount of a compound of the invention or a pharmaceutically acceptable salt or solvate thereof or a therapeutically effective amount of a pharmaceutical composition of the invention. In one aspect, the invention provides treating a disease or condition. In one aspect, the invention provides preventing a disease or condition.

In one aspect, the compound or pharmaceutical composition of the invention is administered topically. In a further aspect, the compound or pharmaceutical composition of the invention is administered as an ophthalmic solution. In another aspect, the compound or pharmaceutical composition of the invention is administered as an ophthalmic emulsion, suspension, gel, or semi-gel. In another aspect, the compound or pharmaceutical composition of the invention is administered as an ophthalmic jelly, oil, ointment, cream, or spray.

The compounds or pharmaceutical compositions of the invention are administered in dosages effective to inhibit the function of αvβ3, αvβ5, αvβ6 and/or αvβ8 integrins and thus treat or prevent a disease condition mediated by the αvβ3, αvβ5, αvβ6 and/or αvβ8 integrin.

The present invention provides a method of treating or preventing a disease or condition mediated by an αv integrin in a subject, comprising administering to a subject in need thereof a therapeutically effective amount of a compound of formula I or a pharmaceutically acceptable salt or solvate thereof or a therapeutically effective amount of a pharmaceutical composition a compound of formula I or a pharmaceutically acceptable salt or solvate thereof. In one aspect, the disease or condition is a disease or condition in which angiogenesis is involved. In a further aspect, the disease or condition is a disease or condition in which ocular angiogenesis is involved.

The present invention also provides a method of treating or preventing an αvβ3, αvβ5, αvβ6 and/or αvβ8 integrin-mediated disease or condition in a subject, comprising administering to a subject in need thereof a therapeutically effective amount of a compound of formula I or a pharmaceutically acceptable salt or solvate thereof or a therapeutically effective amount of a pharmaceutical composition comprising a compound of formula I or a pharmaceutically acceptable salt or solvate thereof. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO). In one aspect, the condition is fibrosis of the liver, kidney, intestine, lung, and heart. In one aspect, the disease is a renal disease, a respiratory disease, a gastrointestinal disease, a cardiovascular disease, a bone and articular disease, a skin disease, an obstetric disease, or a urologic disease.

The present invention also provides a method of treating or preventing an $\alpha v\beta 3$ and/or $\alpha v\beta 5$ integrin-mediated disease or condition in a subject, comprising administering to a subject in need thereof a therapeutically effective amount of a compound of formula I or a pharmaceutically acceptable salt or solvate thereof or a therapeutically effective amount of a pharmaceutical composition a compound of formula I or a pharmaceutically acceptable salt or solvate thereof. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO).

The present invention provides the use of a compound of formula I or a pharmaceutically acceptable salt or solvate thereof in the manufacture of a medicament for the treatment or prevention of a disease or condition in a subject. The present invention provides the use of a compound of formula I or a pharmaceutically acceptable salt or solvate thereof in treating or preventing a disease or condition in a subject.

The present invention provides the use of a compound of formula I or a pharmaceutically acceptable salt or solvate thereof in the manufacture of a medicament for the treatment or prevention of a disease or condition mediated by an $\alpha v$ integrin in a subject. The present invention provides the use of a compound of formula I or a pharmaceutically acceptable salt or solvate thereof in treating or preventing a disease or condition mediated by an $\alpha v$ integrin in a subject. In one aspect, the disease or condition is a disease or condition in which angiogenesis is involved. In a further aspect, the disease or condition is a disease or condition in which ocular angiogenesis is involved.

The present invention also provides the use of a compound of formula I or a pharmaceutically acceptable salt or solvate thereof in the manufacture of a medicament for the treatment or prevention of an $\alpha v\beta 3$, $\alpha v\beta 5$, $\alpha v\beta 6$ and/or $\alpha v\beta 8$ integrin-mediated disease or condition in a subject. The present invention provides the use of a compound of formula I or a pharmaceutically acceptable salt or solvate thereof in treating or preventing of an $\alpha v\beta 3$, $\alpha v\beta 5$, $\alpha v\beta 6$ and/or $\alpha v\beta 8$ integrin-mediated disease or condition in a subject. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO). In one aspect, the condition is fibrosis of the liver, kidney, intestine, lung, and heart. In one aspect, the disease is a renal disease, a respiratory disease, a gastrointestinal disease, a cardiovascular disease, a bone and articular disease, a skin disease, an obstetric disease, or a urologic disease.

The present invention provides a compound of formula I or a pharmaceutically acceptable salt or solvate thereof for use in treating or preventing of a disease or condition in a subject.

The present invention provides a compound of formula I or a pharmaceutically acceptable salt or solvate thereof for use in treating or preventing of a disease or condition mediated by an $\alpha v$ integrin in a subject. In one aspect, the disease or condition is a disease or condition in which angiogenesis is involved. In a further aspect, the disease or condition is a disease or condition in which ocular angiogenesis is involved.

The present invention also provides a compound of formula I or a pharmaceutically acceptable salt or solvate thereof for use in treating or preventing of an $\alpha v\beta 3$, $\alpha v\beta 5$, $\alpha v\beta 6$ and/or $\alpha v\beta 8$ integrin-mediated disease or condition in a subject. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO). In one aspect, the condition is fibrosis of the liver, kidney, intestine, lung, and heart. In one aspect, the disease is a renal disease, a respiratory disease, a gastrointestinal disease, a cardiovascular disease, a bone and articular disease, a skin disease, an obstetric disease, or a urologic disease.

Administration of the second therapy in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner.

In accordance with the method of the invention, the individual components of the combination can be administered separately at different times during the course of therapy or concurrently in divided or single combination forms. The instant invention is therefore to be understood as embracing all such regimens of simultaneous or alternating treatment, and the term "administering" is to be interpreted accordingly. It will be understood that the scope of combinations of the compounds of the invention with other agents useful for treating $\alpha v$ integrin-mediated conditions includes in principle any combination with any pharmaceutical composition useful for treating fibrosis, macular degeneration, DR, DME, or macular edema following RVO. When the method of the invention is a combination treatment of a formulation of the present invention topically administered to the eyes and an anti-VEGF protein or aptamer, the procedures, dosages and frequencies of the anti-VEGF protein or aptamer are as described in the package inserts for those agents.

The dosage regimen utilizing the compounds of the invention is selected in accordance with a variety of factors including type, species, age, weight, sex and medical condition of the patient; the severity of the condition to be treated; and the particular compound or salt thereof employed. An ordinary skilled physician, veterinarian or clinician can readily determine and prescribe the effective amount of the drug required to prevent, counter or arrest the progress of the condition.

In the methods of the invention, the compounds herein described in detail can form the active ingredient, and are typically administered in admixture with suitable pharmaceutical diluents, excipients or carriers (collectively referred to herein as "carrier") suitably selected with respect to the intended topical administration to the eye and consistent with conventional pharmaceutical practices.

For purposes of the invention, the following definitions will be used (unless expressly stated otherwise):

"A compound of the invention", "compounds of the invention", "a compound of the present invention", or "compounds of the present invention" refers to a compound(s) disclosed herein, e.g., a compound(s) of the invention includes a compound(s) of any of the formulae described herein including formula I and Ia and/or a compound(s) explicitly disclosed herein. Whenever the term is used in the context of the invention it is to be understood that the reference is being made to the free base and the corresponding pharmaceutically acceptable salts or solvates thereof, provided that such is possible and/or appropriate under the circumstances.

"Pharmaceutical" or "pharmaceutically acceptable" when used herein as an adjective, means substantially non-toxic and substantially non-deleterious to the recipient.

By "pharmaceutical composition" it is further meant that the carrier, diluent, solvent, excipient, and salt must be compatible with the active ingredient of the formulation (e.g., a compound of the invention). It is understood by those of ordinary skill in this art that the terms "pharmaceutical formulation" and "pharmaceutical composition" are generally interchangeable, and they are so used for the purposes of this application.

"Solution" refers to a clear, homogeneous liquid dosage form that contains one or more chemical substances dissolved in a solvent or mixture of mutually miscible solvents. Because molecules of a therapeutic agent substance in solution are uniformly dispersed, the use of solutions as dosage forms generally provides assurance of uniform dosage upon administration and good accuracy when the solution is diluted or otherwise mixed. "Solution" as disclosed herein contemplates any variations based on the current state of the art or variations achieved by one skilled in the art.

"Suspension" refers to a liquid dosage form that contains solid particles dispersed in a liquid vehicle. "Suspension" as disclosed herein contemplates any variations based on the current state of the art or variations achieved by one skilled in the art.

"Excipient" is used herein to include any other compound that is not a therapeutically or biologically active compound and may be contained in or combined with one or more of the compounds of the present invention. As such, an excipient should be pharmaceutically or biologically acceptable or relevant (for example, an excipient should generally be non-toxic to the subject). "Excipient" includes a single such compound and is also intended to include a plurality of excipients. For the purposes of the present disclosure the term "excipient" and "carrier" are used interchangeably throughout the description of the present application.

"Therapeutically effective amount" refers to that amount of a drug or pharmaceutical agent that will elicit the biological or medical response of a tissue, system, animal, or human that is being sought by a researcher or clinician.

"Treat," "treating," or "treatment" refers to decreasing the symptoms, markers, and/or any negative effects of a disease or condition in any appreciable degree in a subject who currently has the disease or condition. In some embodiments, treatment may be administered to a subject who exhibits only early signs of a disease or condition for the purpose of decreasing the risk of developing the disease or condition. In some embodiments, "Treat," "treating," or "treatment" refers to amelioration of one or more symptoms of a disease or condition. For example, amelioration of one or more symptoms of a disease or condition includes a decrease in the severity, frequency, and/or length of one or more symptoms of a disease or condition.

"Prevent," "prevention," or "preventing" refers to any method to partially or completely prevent or delay the onset of one or more symptoms or features of a disease or condition. Prevention may be administered to a subject who does not exhibit any sign of a disease or condition.

"Subject" means a human or animal (in the case of an animal, more typically a mammal). In one aspect, the subject is a human.

The term "symptom" is defined as an indication of disease, illness, injury, or that something is not right in the body. Symptoms are felt or noticed by the individual experiencing the symptom, but may not easily be noticed by others. Others are defined as non-health-care professionals.

"αv integrin antagonist" refers to a compound which binds to and inhibits or interferes with the function of one or more of αvβ3, αvβ5, αvβ6, and αvβ8, a compound which binds to and inhibits or interferes with the function of both αvβ3 and αvβ5 (i.e., a dual αvβ3/αvβ5 antagonist), or a compound which binds to and inhibits or interferes with the function of both αvβ6 and αvβ8 (i.e., a dual αvβ6/αvβ8 antagonist). The compounds bind to the receptors as antagonists, blocking or interfering with the binding of the native agonist, such as vitronectin, while not provoking a biological response themselves.

"Bone resorption" refers to the process by which osteoclasts degrade bone.

"Alkyl" refers to straight chain or branched alkyl of the number of carbon atoms specified (e.g., $C_1$-$C_4$ alkyl), or any number within this range (methyl, ethyl, propyl, i-propyl, butyl, i-butyl, t-butyl, etc.).

"Alkoxy" refers to straight chain or branched alkoxides of the number of carbon atoms specified (e.g., $C_1$-$C_6$ alkoxy), or any number within this range (methoxy, ethoxy, propoxy, i-propoxy, butoxy, i-butoxy, t-butoxy, etc.).

"Carbocyclic ring" refers to saturated cycloalkyl of the number of carbon atoms specified (i.e., $C_3$ or $C_4$), such as cyclopropyl and cyclobutyl.

"Heterocyclic ring" refers to saturated heterocyclic ring of the number of carbon atoms specified (i.e., $C_3$ or $C_4$), further comprising one additional heteroatoms selected from N, O, and S.

The term "about" refers to a range of values which can be 15%, 10%, 8%, 5%, 3%, 2%, 1%, or 0.5% more or less than the specified value. For example, "about 10%" can be from 8.5% to 11.5%. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

EXAMPLES

Abbreviations used in the following examples and elsewhere herein are:
AcOH acetic acid
Boc$_2$O di-tert-butyl dicarbonate
DCM dichloromethane
equiv equivalent(s)
EtCO$_2$H propionic acid
EtOAc ethyl acetate
EtOH ethanol
Et$_2$O diethyl ether
Et$_3$N triethyl amine
hr hour(s)
HPLC high-performance liquid chromatography
iPrOAc isopropyl acetate
iPrMgCl isopropyl magnesium chloride
iPr$_2$NH diisopropyl amine
LCMS liquid chromatography-mass spectrometry
MeCN acetonitrile
n-BuLi n-butyl lithium
NMP N-methyl-2-pyrrolidone
Pd(OAc)$_2$ palladium (II) acetate
PhMe toluene
P(o-tol)$_3$ tri(O-tolyl)phosphine
RT retention time
t-BuLi tert-butyl lithium
t-BuOK potassium tert-butoxide
TFA trifluoroacetic acid
THF tetrahydrofuran
TLC thin layer chromatography Example 1. Synthesis of (S)-3-(6-(difluoromethoxy)-pyridine-3-yl)-3-(2-oxo-3-(3-(5,6,7,8-tetrahydro-1,8-naphthyridin-2-yl)propyl)imidazolidin-1-yl) propanoic acid (Compound A1)

Compound A1 was made using a convergent synthesis scheme as shown in Scheme 2-1: fragment 6b is reacted with fragment 9 to form compound 10, which is further reacted in three steps to form Compound A1.

Synthesis of Fragment 6b (Scheme 1)

tert-butyl 2-oxopyrrolidine-1-carboxylate (2a)

To a stirred solution of compound 1a (10.0 g, 117 mmol, 1.0 equiv) in CH$_2$Cl$_2$, were added (Boc)$_2$O (25.5 g, 117 mmol, 1.00 equiv) and DMAP (0.022 g, 0.180 mmol, 0.001 equiv) at room temperature and the resulting mixture was stirred for 12 hr. After consumption of the starting material (monitored by TLC), volatiles were removed under reduced pressure to afford compound 2a (19.6 g, 90.3%) as a brown syrup. TLC: 50% EtOAc/Hexane (R$_f$: 0.40).

NMR Spectroscopy: $^1$H NMR (400 MHz, CDCl$_3$): δ 3.74 (t, J=6.8 Hz, 50 (t, J=8.0 Hz, 2H), 2.01 (t, J=7.6 Hz, 2H), 1.52 (s, 9H).

tert-butyl (5-(dimethoxyphosphoryl)-4-oxopentyl)carbamate (3a)

To a stirred solution of iPr$_2$NH (2.99 mL, 21.8 mmol, 1.35 equiv) in THF and cooled to −10° C., was slowly added hexyl lithium (8.79 mL, 20.0 mmol, 1.24 equiv). The reaction mixture was cooled to −60° C., dimethylmethyl phosphonate (2.20 mL, 20.9 mmol, 1.29 equiv) was added and the resulting mixture was stirred for 1 h. Then, the temperature was raised to −40° C., and compound 2a (3.0 g, 16.2 mmol, 1.0 equiv) was added and the reaction mixture was stirred for an additional 1 hr. After consumption of the starting material, 2N H$_2$SO$_4$ solution (20 mL) was added slowly to the reaction and the resulting mixture was stirred at 0° C. for 15 minutes. The aqueous layer was extracted with EtOAc (2×25 mL), and the combined organic extracts were washed with water (25 mL), brine (25 ml), dried over Na$_2$SO$_4$, filtered, and evaporated under reduced pressure to afford compound 3a as a brown liquid (5.0 g, crude).

TLC: 80% EtOAc/Hexane (R$_f$: 0.30).

NMR Spectroscopy: $^1$H NMR (400 MHz, CDCl$_3$): δ 4.85 (brs, 1H, Exc), 3.80-3.72 (m, 8H), 3.13-3.07 (m, 2H), 2.67 (t, J=6.8 Hz, 2H), 1.87-1.76 (m, 2H), 1.43 (s, 9H).

LC-MS: m/z=308.3 [M+H]$^+$ at RT 2.67 (99.1% purity).

tert-butyl (3-(1,8-naphthyridin-2-yl)propyl)carbamate (5a)

To a stirred solution of compound 4a (0.500 g, 4.09 mmol, 1.0 equiv) and compound 3a (1.26 g, crude, 1.0 equiv) in MeOH (9.17 mL), was added 50% NaOH solution (0.314 mL) and the reaction mixture was stirred at 50° C. for 10 hr. After consumption of the starting material (by TLC), the volatiles were removed, the crude residue was diluted with EtOAc (15 mL), and the organic layer was washed with water (2×15 mL). The separated organic layer was dried over Na$_2$SO$_4$, filtered, and concentrated under reduced pressure to afford brown syrup, which was purified by column chromatography on neutral alumina (80% EtOAc: Hexane) to provide compound 5a (0.980 g, 83.3%) as an off-white solid.

TLC: EtOAc.

NMR Spectroscopy: $^1$H NMR (500 MHz, CDCl$_3$): δ 9.09 (s, 1H), 8.17-8.15 (m, 1H), 8.10 (d, J=8.0 Hz, 1H), 7.45 (t, J=8.0 Hz, 1H), 7.41 (t, J=15.0, 1H), 4.76 (brs, 1H, Exc), 3.25-3.21 (m, 2H), 3.09 (t, J=10.0 Hz, 2H), 2.14-2.08 (m, 2H), 1.42 (s, 9H).

LC-MS: m/z=288 [M−H]$^−$ at RT 2.86 (94.7%).

tert-butyl (3-(5,6,7,8-tetrahydro-1,8-naphthyridin-2-yl)propyl)carbamate (6a)

To a stirred solution of compound 5a (0.25 g, 0.87 mmol, 1.00 equiv) in MeOH (5 mL), Rh/C (catalytic, 5 wt %) was added under N$_2$ atmosphere and stirred at room temperature for 8 h under hydrogen (balloon pressure) atmosphere. After consumption of the starting material, the reaction mixture was filtered through a pad of CELITE® and the pad was washed with MeOH (5 mL). The filtrate was evaporated under reduced pressure to afford compound 6a (0.18 g, 71.1%) as a white solid.

TLC: EtOAc.

NMR Spectroscopy: $^1$H NMR (400 MHz, CDCl$_3$): δ 7.05 (d, J=7.6 Hz, 1H), 6.34 (d, J=7.2 Hz, 1H), 5.44 (s, 1H), 4.78 (brs, 1H, Exc), 3.41-3.38 (m, 2H), 3.16 (d, J=6.0 Hz, 2H), 2.68 (t, J=6.0 Hz, 2H), 2.59 (t, J=7.6 Hz, 2H), 1.93-1.81 (m, 4H), 1.44 (s, 9H).

LC-MS: m/z=292.3 [M+H]$^+$ at RT 3.41 (97.9% purity).

3-(5,6,7,8-tetrahydro-1,8-naphthyridin-2-yl)propan-1-amine (6b)

To a stirred solution of 6a (0.25 g, 0.85 mmol, 1.00 equiv) in CH$_2$Cl$_2$ (5 mL) and cooled to 0° C., was added TFA (0.13 mL, 1.69 mmol, 2.00 equiv). The reaction was warmed to room temperature and then stirred for 4 h. After consumption of the starting material (by TLC), the reaction mixture was concentrated under reduced pressure to afford crude compound 6b (0.30 g) as a thick syrup which was used in the next step without purification.

Synthesis of Fragment 9 and Completion of the Synthesis 5-bromo-2-(difluoromethoxy)pyridine (2)

To a stirred solution of compound 1 (4.50 g, 25.8 mmol, 1.0 equiv) in anhydrous MeCN (80 mL), was added sodium 2-chloro-2,2-difluoroacetate (4.89 g, 31.0 mmol, 1.20 equiv) at room temperature and resulting mixture was stirred at 70° C. for 48 hr. After consumption of the starting material (by TLC), the reaction mixture was cooled to room temperature and diluted with NH$_4$Cl solution (30 mL). The aqueous layer was extracted with EtOAc (2×40 mL). The combined organic layers were washed with brine solution (2×50 mL), dried over anhydrous Na$_2$SO$_4$, filtered and concentrated under reduced pressure to give the crude compound which was purified by silica gel column chromatography (2% EtOAc/hexane) to afford compound 2 (3.2 g, 57%) as pale yellow syrup. TLC: 5% EtOAc/Hexane (R$_f$: 0.5).

NMR Spectroscopy: $^1$H NMR (400 MHz, CDCl$_3$): δ 8.25 (d, J=2.8 Hz, 1H), 7.82 (dd, J=2.4, 6.4 Hz, 1H), 7.40 (t, J=72.8 Hz, 1H), 6.83 (d, J=8.8 Hz, 1H).

LC-MS: m/z=224.7 [M+H]$^+$ at RT 4.22 (98.2% purity).

(E)-tert-butyl 3-(6-(difluoromethoxy)pyridin-3-yl)acrylate (3)

To a stirred solution of tert-butyl acrylate (9.99 g, 78.1 mmol, 3.50 equiv), Et$_3$N (8.5 mL, 60.2 mmol, 2.70 equiv), and N-methyl pyrrolidine (20 mL), was added tritolylphosphine (1.17 g, 3.52 mmol, 0.16 equiv) followed by Pd(OAc)$_2$ (0.50 g, 2.22 mmol, 0.09 equiv). The temperature was gradually warmed to 90° C. and compound 2 (5.00 g, 22.3 mmol, 1.0 equiv) in NMP (10 mL) was then added drop wise and the resulting mixture was stirred at 90° C. for 12 hr. After consumption of the starting material (by TLC), the reaction mixture was filtered through a pad of CELITE® and the pad was washed with EtOAc (50 mL). The filtrate was washed with cold water (2×50 mL) followed by NaOCl (50 mL), and brine solution (50 mL). The organic layer was dried over anhydrous Na$_2$SO$_4$, filtered, and concentrated under reduced pressure to give the crude residue which was purified by silica gel column chromatography (3% EtOAc/hexane) to afford compound 3 (4.0 g, 66%) as yellow solid.

TLC: 5% EtOAc/Hexane (R$_f$: 0.5).

NMR Spectroscopy: $^1$H NMR (400 MHz, CDCl$_3$): δ 8.28 (d, J=2.4 Hz, 1H), 7.88 (dd, J=2.0, 6.4 Hz, 1H), 7.56 (d, J=16.0 Hz, 1H), 7.55 (t, J=45.6 Hz, 1H), 6.91 (d, J=8.4 Hz, 1H), 6.34 (d, J=16.0 Hz, 1H), 1.53 (s, 9H).

LC-MS: m/z=272 [M+H]$^+$ at RT 4.16 (99.5% purity).

(S)-tert-butyl 3-(benzyl ((R)-1-phenylethyl)amino)-3-(6-methoxypyridin-3-yl)propanoate (5)

To a stirred solution of compound 4 (0.39 g, 1.85 mmol, 2.0 equiv) in THF (5 mL) and cooled to −30° C., was added n-BuLi (0.66 mL, 1.65 mmol, 1.79 equiv) and the resulting mixture was then cooled to −78° C. Compound 3 (0.25 g, 0.92 mmol, 1.0 equiv) dissolved in THF (3 mL) was added and the reaction mixture was stirred for 30 min and then quenched with saturated ammonium chloride. The reaction mixture was extracted with EtOAc (2×20 mL). The combined organic extracts were washed with 10% AcOH and brine solution, dried over anhydrous Na$_2$SO$_4$, filtered, and concentrated under reduced pressure to give the crude compound (mixture of 3 and 5, 0.17 g) as thick syrup, which was directly used in the next step.

TLC: 5% EtOAc/Hexane (R$_f$: 0.5).

LC-MS: m/z=483 [M+H]$^+$ at RT 4.66 (75.1% purity).

Synthesis of (s)-tert-butyl 3-amino-3-(6-(difluoromethoxy)pyridin-3-yl)propanoate (S-029)

To a stirred solution of compound 5 (0.80 g, crude mixture) in EtOAc (5 mL) and AcOH (0.5 mL) under N$_2$ atmosphere, was added 20% Pd(OH)$_2$ (50 mg). The resulting mixture was then stirred under H$_2$ atmosphere (40 psi) at room temperature for 2 hr. After consumption of the starting material (monitored by TLC), the reaction mixture was filtered through a pad of CELITE® and the filtrate was concentrated under reduced pressure to afford crude compound which was purified by silica gel column chromatography (2% MeOH/CH$_2$Cl$_2$) to furnish S-029 (0.3 g, 63%) as yellow syrup.

TLC: 5% MeOH/CH$_2$Cl$_2$ (R$_f$: 0.3).

NMR Spectroscopy: $^1$H NMR (400 MHz, CDCl$_3$): δ 8.17 (d, J=2.8 Hz, 1H), 7.78 (dd, J=2.4, 6.4 Hz, 1H), 7.44 (t, 73.2 Hz, 1H), 6.88 (d, J=8.4 Hz, 1H), 4.43-4.40 (m, 1H), 2.65-2.56 (m, 2H), 1.42 (s, 9H).

LC-MS: m/z=274 [M+H]$^+$ at RT 2.76 (99.8% purity).

(S,E)-tert-Butyl 3-(6-(tert-butoxy) pyridin-3-yl)-3-((2,2-dimethoxyethylidene)amino)propanoate (7)

To a stirred solution of dimethoxy acetaldehyde (0.44 mL, 2.50 mmol, 1.20 equiv, 60% in water) in CH$_2$Cl$_2$ (10 mL) and cooled to 0° C., was added anhydrous MgSO$_4$ (10 g) followed by S-029 (600 mg, 2.08 mmol, 1.0 equiv) in CH$_2$Cl$_2$ (5 mL). The reaction mixture was stirred at room temperature for 2 hr and then filtered through a pad of CELITE®. The filtrate was concentrated under reduced pressure to afford compound 7 (650 mg, crude) as a yellow liquid which was used in the next step without further purification. TLC: 5% MeOH/CH$_2$Cl$_2$ (R$_f$: 0.5).

(S)-tert-butyl 3-(6-(difluoromethoxy)pyridin-3-yl)-3-((2,2-dimethoxyethyl) amino) propanoate (8)

To a stirred solution of compound 7 (0.65 g, crude, 1.0 equiv) in MeOH (7 mL) and cooled to 0° C., was added NaBH(CN)$_3$ (0.13 g, 2.09 mmol, 1.20 equiv) and the resulting mixture was stirred at room temperature for 2 hr. After consumption of the starting material (by TLC), the MeOH was removed under reduced pressure to give the crude residue which was diluted with water (10 mL) and extracted with EtOAc (2×10 ml). The combined organic extracts were dried over anhydrous $Na_2SO_4$, filtered, and concentrated under reduced pressure to give the crude material which was purified by silica gel column chromatography (2% MeOH/$CH_2Cl_2$) to afford compound 8 (0.52 g, 79%) as a thick syrup.

TLC: 5% MeOH/$CH_2Cl_2$ ($R_f$: 0.7).

NMR Spectroscopy: $^1$H NMR (400 MHz, $CDCl_3$): δ 8.13 (d, J=2.0 Hz, 1H), 7.75 (dd, J=2.4, 6.0 Hz, 1H), 7.44 (t, J=73.2 Hz, 1H), 6.87 (d, J=8.4 Hz, 1H), 4.43-4.37 (m, 2H), 4.06-4.02 (m, 1H), 3.60-3.54 (m, 2H), 3.35 (s, 3H) 3.31 (s, 3H), 2.66-2.57 (m, 2H), 1.39 (s, 9H).

LC-MS: m/z=377 [M+H]$^+$ at RT 2.96 (92.3% purity).

(S)-tert-butyl 3-(6-(difluoromethoxy) pyridin-3-yl)-3-(1-(2,2-dimethoxyethyl)-3-(3-(5,6,7,8-tetrahydro-1,8-naphthyridin-2-yl)propyl)ureido)propanoate (10)

To a stirred solution of compound 8 (375 mg, 0.99 mmol, 1.0 equiv) in dry $CH_2Cl_2$ (5 mL) and cooled to 0° C., was added triphosgene (1.50 mL, 2.99 mmol, 3.00 equiv, 20% in PhMe) followed by $Et_3N$ (0.30 mL, 2.09 mmol, 2.10 equiv). The reaction mixture was slowly warmed to room temperature and then stirred for 2 hr. After consumption of the starting material, the volatiles were evaporated to afford the crude compound 9, which was used directly in the next step without purification.

A solution of compound 9 in DCE (2 mL) was added to a solution of compound 6b (400 mg, 1.32 mmol, 1.32 equiv) in $CH_2Cl_2$ (5 mL) and $Et_3N$ (0.55 mL, 3.98 mmol, 4.00 equiv) at 0° C. and the resulting mixture was stirred at room temperature for 4 hr. After consumption of the starting material (monitored by TLC), the reaction mixture was concentrated under reduced pressure to give the crude residue which was purified by silica gel column chromatography (2% MeOH/$CH_2Cl_2$) to afford compound 10 (0.40 g, 67%) as a thick syrup.

TLC: 5% MeOH/$CH_2Cl_2$ ($R_f$: 0.2).

NMR Spectroscopy: $^1$H NMR (400 MHz, $CDCl_3$): δ 8.13 (d, J=2.8 Hz, 1H), 7.79 (dd, J=2.4, 6.4 Hz, 1H), 7.62 (tt, J=72.8 Hz, 1H), 7.12 (d, J=6.4 Hz, 1H), 6.86 (d, J=8.4 Hz, 1H), 6.36 (d, J=3.6 Hz, 1H), 6.22 (t, J=4.8 Hz, 1H), 5.75 (t, J=7.6 Hz, 1H), 4.26 (t, J=5.2 Hz, 1H), 3.45-3.38 (m, 8H), 3.27-3.13 (m, 3H), 2.99-2.93 (m, 2H), 2.71-2.59 (m, 5H), 1.93-1.83 (m, 5H), 1.39 (s, 9H).

LC-MS: m/z=594 [M+H]$^+$ at RT 3.42 (88.1% purity).

(S)-tert-Butyl 3-(6-(difluoromethoxy) pyridin-3-yl)-3-(2-oxo-3-(3-(5,6,7,8-tetrahydro-1,8-naphthyridin-2-yl)propyl)-2,3-dihydro-1H-imidazol-1-yl)propanoate (11)

To a stirred solution of compound 10 (0.20 g, 0.34 mmol, 1.0 equiv) in THF (4 mL) and at −10° C., was added 1 M sulfuric acid (0.8 mL). The reaction mixture was slowly warmed to room temperature and then stirred for 10 hr. After consumption of the starting material (monitored by LCMS), the THF was removed and the crude residue was neutralized with sodium hydroxide (50 wt %) to a pH of ~7. The aqueous layer was extracted with 5% MeOH/$CH_2Cl_2$ (3×20 mL) and the combined organic extracts were dried over anhydrous $Na_2SO_4$, filtered, and concentrated under reduced pressure to furnish compound 11 (0.22 g, crude) as a syrup.

TLC: 10% MeOH/$CH_2Cl_2$ ($R_f$: 0.5).

LC-MS: m/z=530 [M+H]$^+$ at RT 4.06 (72.8% purity).

(S)-tert-Butyl 3-(6-(difluoromethoxy) pyridin-3-yl)-3-(2-oxo-3-(3-(5,6,7,8-tetrahydro-1,8-naphthyridin-2-yl)propyl) imidazolidin-1-yl)propanoate (12)

To a stirred solution of compound 11 (0.45 g, crude, 1.0 equiv) in EtOH (8 mL) under $N_2$ atmosphere, was added 20% Pd/C (200 mg). The resulting mixture was stirred under $H_2$ atmosphere (40 psi) at room temperature for 36 hr. After consumption of the starting material the reaction mixture was filtered through a pad of CELITE®, and the filtrate was concentrated under reduced pressure to afford crude compound 12, which was purified by chiral preparative HPLC to afford compound 12 (450 mg, crude) as an off-white solid.

TLC: 10% MeOH/$CH_2Cl_2$ ($R_f$: 0.5).

LC-MS: m/z=532.6 [M+H]$^+$ at RT 3.99 (80.1% purity).

(S)-3-(6-(difluoromethoxy)pyridin-3-yl)-3-(2-oxo-3-(3-(5,6,7,8-tetrahydro-1,8-naphthyridin-2-yl)propyl) imidazolidin-1-yl)propanoic acid (Compound A1)

To a stirred solution of compound 12 (0.40 g, crude, 1.0 equiv) in $CH_2Cl_2$ (2 mL), cooled to −10° C., and under $N_2$ atmosphere, was added TFA (0.5 mL). The reaction mixture was slowly warmed to room temperature and then stirred for 2 hr. After consumption of the starting material, the volatiles were evaporated to afford crude (400 mg) compound, which was purified by chiral preparative HPLC to afford compound A1 as an off-white solid.

TLC: 10% MeOH/$CH_2Cl_2$ ($R_f$: 0.3).

NMR Spectroscopy: $^1$H NMR (400 MHz, $CD_3OD$): δ 8.20 (d, J=2.4 Hz, 1H), 7.85 (dd, J=2.4, 6.4 Hz, 1H), 7.53 (t, J=2.4 Hz, 1H), 7.50 (d, J=7.2 Hz, 1H), 6.98 (d, J=8.4 Hz, 1H), 6.57 (d, J=7.2 Hz, 1H), 5.51 (dd, J=3.6, 8.0 Hz, 1H), 3.68-3.61 (m, 1H), 3.52-3.46 (m, 3H), 3.38 (m, 1H), 3.24-3.17 (m, 1H), 3.07-2.98 (m, 2H), 2.90-2.62 (m, 6H), 2.09-1.81 (m, 4H).

LC-MS: m/z=476 [M+H]$^+$ at RT 2.78 (97.9% purity).

HPLC purity: 96.4%; Chiral Purity: 99%.

The compounds of the present invention described in Examples 2-7 in which Z is —$CH_2CH_2CH_2$— were synthesized using the general reaction scheme shown in Scheme 3. Dimethyl (2-oxo-6-(5,6,7,8-tetrahydro-1,8-naphthyridin-2-yl)hexyl)phosphonate was added to the fluorinated nitrogen heterocycle (Q) aldehyde to form the hept-1-en-3-one. The hept-1-en-3-one was reduced to the corresponding hept-1-en-3-ol using lithium aluminum hydride or sodium borohydride. The hept-1-en-3ol was then reacted with propionic acid in 1,1,1-triethoxyethane and the resulting crude rearrangement product was reduced with hydrogen and palladium on carbon catalyst to the corresponding olefin reduction product which was then reacted with aqueous base to form the final nonanoic acid compounds.

Example 2. Synthesis of 9-(5,6,7,8-tetrahydro-1,8-naphthyridin-2-yl)-3-(2-(trifluoromethyl)pyrimidin-5-yl)nonanoic acid (Compound A2)

(E)-7-(5,6,7,8-tetrahydro-1,8-naphthyridin-2-yl)-1-(2-(trifluoromethyl)pyrimidin-5-yl)hept-1-en-3-one

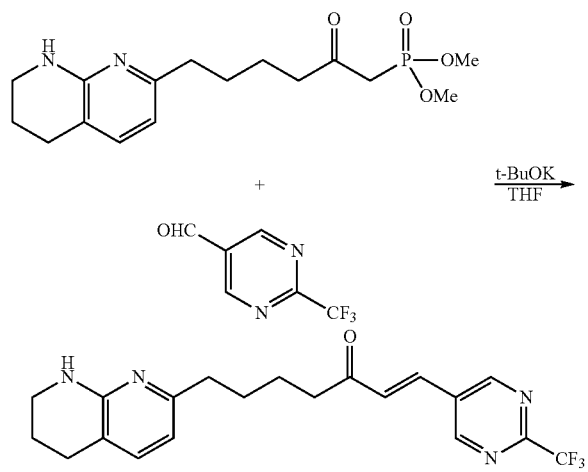

To dimethyl (2-oxo-6-(5,6,7,8-tetrahydro-1,8-naphthyridin-2-yl)hexyl)phosphonate (3.40 g, 10.0 mmol, 1.00 equiv; Coleman, P. J. et al., *J. Med. Chem.* 2004, 47:4829-4837) in THF (10 mL) at 23° C. and under $N_2$ atmosphere, was added 2-(trifluoromethyl)pyrimidine-5-carbaldehyde (1.76 g, 10.0 mmol, 1.00 equiv) and t-BuOK (1.01 g, 9.00 mmol, 0.900 equiv). After stirring for 10 min at 23° C., the reaction mixture was purified by silica gel column chromatography eluting with $CH_2Cl_2$/MeOH to afford 2.10 g of the title compound (54% yield). NMR Spectroscopy: $^1$H NMR (300 MHz, $CDCl_3$): δ 9.03 (s, 2H), 7.50 (d, J=16.2 Hz, 1H), 7.07 (d, J=7.2 Hz, 1H), 6.93 (d, J=16.2 Hz, 1H), 6.35 (d, J=7.2 Hz, 1H), 5.17 (br s, 1H), 3.42-3.37 (m, 2H), 2.79-2.64 (m, 4H), 2.62-2.55 (m, 2H), 1.95-1.85 (m, 2H), 1.77-1.66 (m, 4H). $^{19}$F NMR (282 MHz, $CDCl_3$): δ −70.3 (s, 3F).

(E)-7-(5,6,7,8-tetrahydro-1,8-naphthyridin-2-yl)-1-(2-(trifluoromethyl)pyrimidin-5-yl)hept-1-en-3-ol

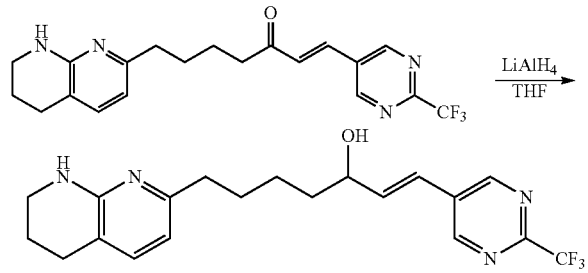

To (E)-7-(5,6,7,8-tetrahydro-1,8-naphthyridin-2-yl)-1-(2-(trifluoromethyl)pyrimidin-5-yl)hept-1-en-3-one (1.20 g, 3.07 mmol, 1.00 equiv) in THF (15 mL) at −78° C. and under $N_2$ atmosphere, was added $LiAlH_4$ (1.0 M in THF, 3.07 mL, 3.07 mmol, 1.00 equiv). After stirring for 10 min at −78° C., $H_2O$ (116 μL) 15% NaOH aq (116 and $H_2O$ (348 μL) were added sequentially. The reaction mixture was then warmed to 23° C. and filtered through a pad of CELITE®. The filtrate was concentrated in vacuo and the residue was purified by silica gel column chromatography eluting with $CH_2Cl_2$/MeOH to afford 560 mg of the title compound (46% yield).
NMR Spectroscopy: $^1$H NMR (300 MHz, $CDCl_3$): δ 8.86 (s, 2H), 7.06 (d, J=7.2 Hz, 1H), 6.66 (d, J=16.2 Hz, 1H), 6.53 (dd, J=16.2 Hz, 4.5 Hz, 1H), 6.34 (d, J=7.2 Hz, 1H), 4.81 (br s, 1H), 4.50-4.40 (m, 1H), 3.42-3.37 (m, 2H), 2.70-2.50 (m, 4H), 1.96-1.40 (m, 8H). $^{19}$F NMR (282 MHz, $CDCl_3$): δ −70.1 (s, 3F).

9-(5,6,7,8-tetrahydro-1,8-naphthyridin-2-yl)-3-(2-(trifluoromethyl)pyrimidin-5-yl)nonanoic acid (Compound A2)

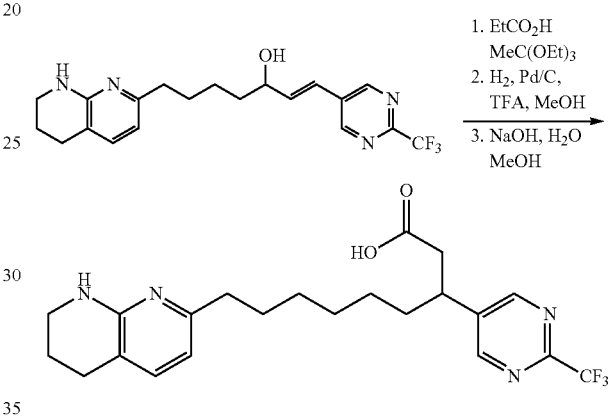

To (E)-7-(5,6,7,8-tetrahydro-1,8-naphthyridin-2-yl)-1-(2-(trifluoromethyl)pyrimidin-5-yl)hept-1-en-3-ol (560 mg, 1.43 mmol, 1.00 equiv) in $MeC(OEt)_3$ (14 mL) at 23° C. and under $N_2$ atmosphere, was added $EtCO_2H$ (107 μL, 1.43 mmol, 1.00 equiv). After stirring for 2 hr at 140° C., the reaction mixture was purified by silica gel column chromatography eluting with hexanes/EtOAc to afford a crude rearrangement product, which was used in the next step without further purification.

To the above obtained residue in MeOH-TFA (10 mL-1 mL) at 23° C. and under an atmosphere of air, was added 10% Pd/C (103 mg, 0.0969 mmol, 6.78 mol %) and $H_2$ gas was introduced into the reaction mixture with a balloon. After stirring for 1 hr at 23° C., the reaction mixture was filtered through a pad of CELITE®. The filtrate was concentrated in vacuo to afford a crude olefin reduction product, which was used in the next step without further purification.

To the above obtained residue in MeOH (10 mL) at 23° C. was added 15% NaOH aq (2.7 mL) under an atmosphere of air. After stirring for 20 min at 60° C., the reaction mixture was neutralized with 3N HCl and then concentrated in vacuo to remove the MeOH. The residual aqueous solution was extracted with EtOAc (3×10 mL) and the combined organic phases were washed with $NaHCO_3$ aq (2×5 mL), dried ($MgSO_4$), and filtered. The filtrate was concentrated in vacuo and the residue was purified by silica gel column chromatography eluting with $CH_2Cl_2$/MeOH to afford 280 mg of the title compound (45% yield over 3 steps).

NMR Spectroscopy: $^1$H NMR (300 MHz, $CDCl_3$): δ 8.79 (s, 2H), 7.24 (d, J=7.2 Hz, 1H), 6.25 (d, J=7.2 Hz, 1H), 3.48-3.40 (m, 2H), 3.38-3.32 (m, 1H), 2.75-2.52 (m, 4H), 1.95-1.80 (m, 4H), 1.75-1.58 (m, 4H), 1.40-1.18 (m, 6H). $^{19}$F NMR (282 MHz, CDCl$_3$): δ −70.1 (s, 3F).

Example 3. Synthesis of 3-(6-(difluoromethoxy) pyridin-3-yl)-9-(5,6,7,8-tetrahydro-1,8-naphthyridin-2-yl)nonanoic acid (Compound A3)

6-(difluoromethoxy)nicotinaldehyde

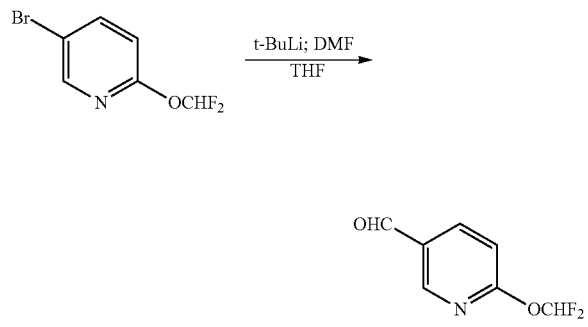

To 5-bromo-2-(difluoromethoxy)pyridine (448 mg, 2.00 mmol, 1.00 equiv; Ando, M. et al., *Org. Lett.* 2006, 8:3805-3808) in THF (10 mL) at −78° C. and under an atmosphere of N$_2$, was added t-BuLi (1.7 M in pentane, 2.35 mL, 4.00 mmol, 2.00 equiv) dropwise over 5 min. After stirring for 20 min at −78° C., DMF (0.54 mL, 7.0 mmol, 3.5 equiv) was added to the reaction mixture. After stirring for 20 min at −78° C., 1N HCl aq (10 mL) was added and the resulting mixture was warmed to 23° C. The phases were separated and the aqueous phase was extracted with EtOAc (3×5 mL). The combined organic phases were washed with brine (10 mL), dried (MgSO$_4$), and filtered. The filtrate was concentrated in vacuo and the resulting residue was purified by silica gel column chromatography eluting with hexanes/EtOAc to afford 105 mg of the title compound (30% yield).

NMR Spectroscopy: $^1$H NMR (300 MHz, CDCl$_3$): δ 10.05 (s, 1H), 8.69 (d, J=2.1 Hz, 1H), 8.24 (dd, J=8.4 Hz, 2.4 Hz, 1H), 7.56 (t, J=72.3 Hz, 1H), 7.04 (d, J=8.4 Hz, 1H). $^{19}$F NMR (282 MHz, CDCl$_3$): δ −89.8 (d, J=72.3 Hz, 2F).

(E)-1-(6-(difluoromethoxy)pyridin-3-yl)-7-(5,6,7,8-tetrahydro-1,8-naphthyridin-2-yl)hept-1-en-3-one

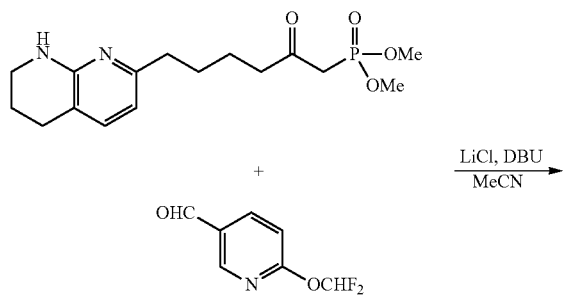

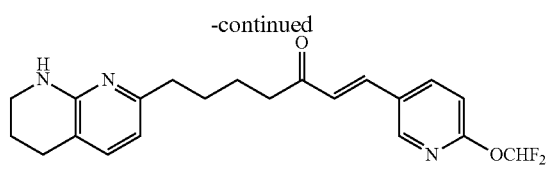

To dimethyl (2-oxo-6-(5,6,7,8-tetrahydro-1,8-naphthyridin-2-yl)hexyl)phosphonate (1.57 g, 4.62 mmol, 1.00 equiv) in MeCN (11 mL) at 23° C. and under an atmosphere of N$_2$, was added 6-(difluoromethoxy)nicotinaldehyde (800 mg, 4.62 mmol, 1.00 equiv), LiCl (196 mg, 4.62 mmol, 1.00 equiv) and DBU (0.725 mL, 4.85 mmol, 1.05 equiv). After stirring for 1 hr at 50° C., the reaction mixture was cooled to 23° C. and then filtered through a pad of CELITE®. The filtrate was concentrated in vacuo and the resulting residue was purified by silica gel column chromatography eluting with CH$_2$Cl$_2$/MeOH to afford 1.27 g of the title compound (71% yield).

NMR Spectroscopy: $^1$H NMR (300 MHz, CDCl$_3$): δ 8.32 (d, J=2.4 Hz, 1H), 7.92 (dd, J=8.4 Hz, 2.4 Hz, 1H), 7.49 (t, J=72.3 Hz, 1H), 7.47 (d, J=16.2 Hz, 1H), 7.06 (d, J=7.2 Hz, 1H), 6.93 (d, J=8.7 Hz, 1H), 6.70 (d, J=16.2 Hz, 1H), 6.35 (d, J=7.2 Hz, 1H), 4.89 (br s, 1H), 3.42-3.36 (m, 2H), 2.76-2.64 (m, 4H), 2.62-2.56 (m, 2H), 1.94-1.85 (m, 2H), 1.80-1.66 (m, 4H). $^{19}$F NMR (282 MHz, CDCl$_3$): δ −89.2 (d, J=72.3 Hz, 2F).

(E)-1-(6-(difluoromethoxy)pyridin-3-yl)-7-(5,6,7,8-tetrahydro-1,8-naphthyridin-2-yl)hept-1-en-3-ol

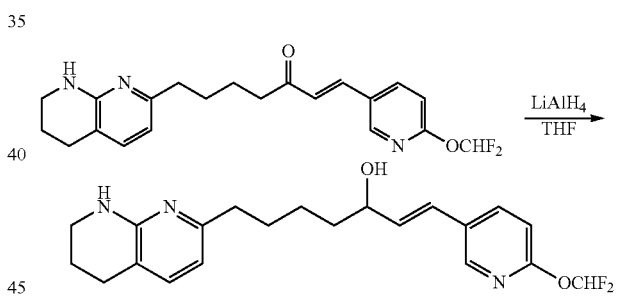

To (E)-1-(6-(difluoromethoxy)pyridin-3-yl)-'7-(5,6,7,8-tetrahydro-1,8-naphthyridin-2-yl)hept-1-en-3-one (1.27 g, 3.28 mmol, 1.00 equiv) in THF (33 mL) at 0° C. and under an atmosphere of N$_2$, was added LiAlH$_4$ (1.0 M in THF, 3.28 mL, 3.28 mmol, 1.00 equiv). After stirring for 10 min at 0° C., H$_2$O (124 µL), 15% NaOH aq (124 µL), and H$_2$O (372 µL) were added sequentially and the resulting mixture was warmed to 23° C. and filtered through a pad of CELITE®. The filtrate was concentrated in vacuo and the residue was purified by silica gel column chromatography eluting with CH$_2$Cl$_2$/MeOH to afford 1.05 g of the title compound (82% yield).

NMR Spectroscopy: $^1$H NMR (300 MHz, CDCl$_3$): δ 8.22 (d, J=2.4 Hz, 1H), 7.84 (dd, J=8.4 Hz, 2.4 Hz, 1H), 7.49 (t, J=72.3 Hz, 1H), 7.05 (d, J=7.2 Hz, 1H), 6.88 (d, J=8.7 Hz, 1H), 6.66 (d, J=16.2 Hz, 1H), 6.55 (dd, J=16.2 Hz, 4.5 Hz, 1H), 6.33 (d, J=7.2 Hz, 1H), 4.84 (br s, 1H), 4.52-4.43 (m, 1H), 3.40-3.37 (m, 2H), 2.72-2.51 (m, 4H), 1.95-1.40 (m, 8H). $^{19}$F NMR (282 MHz, CDCl$_3$): δ −89.0 (d, J=72.5 Hz, 2F).

3-(6-(difluoromethoxy)pyridin-3-yl)-9-(5,6,7,8-tetra-hydro-1,8-naphthyridin-2-yl)nonanoic acid (Compound A3)

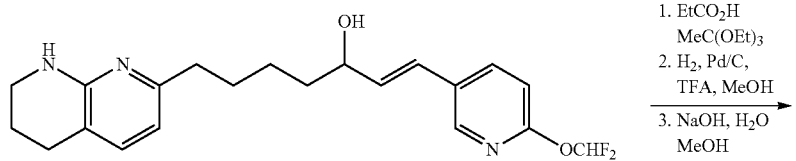

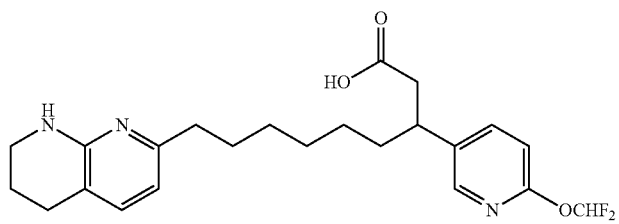

To (E)-1-(6-(difluoromethoxy)pyridin-3-yl)-7-(5,6,7,8-tetrahydro-1,8-naphthyridin-2-yl)hept-1-en-3-ol (1.05 g, 2.70 mmol, 1.00 equiv) in MeC(OEt)₃ (27 mL) at 23° C. and under an atmosphere of N₂, was added EtCO₂H (201 µL, 2.70 mmol, 1.00 equiv). After stirring for 2 hr at 140° C., the reaction mixture was directly loaded onto silica gel and purified by column chromatography on silica gel eluting with hexanes/EtOAc to afford a crude rearrangement product, which was used in the next step without further purification.

To the above obtained residue in MeOH-TFA (10 mL-1 mL) at 23° C. and under an atmosphere of air, was added 10% Pd/C (176 mg, 0.165 mmol, 6.11 mol %) and H₂ gas was introduced into the reaction mixture with a balloon. After stirring for 1 hr at 23° C., the reaction mixture was filtered through a pad of CELITE®. The filtrate was concentrated in vacuo to afford a crude olefin reduction product, which was used in the next step without further purification.

To the above obtained residue in MeOH (10 mL) at 23° C. and under an atmosphere of air, was added 15% NaOH aq (4.4 mL). After stirring for 20 min at 60° C., the reaction mixture was neutralized with 3N HCl and concentrated in vacuo to remove the MeOH. The residual aqueous solution was extracted with EtOAc (3×10 mL) and the combined organic phases were washed with NaHCO₃ aq (2×5 mL), dried (MgSO₄), and filtered. The filtrate was concentrated in vacuo and the residue was purified by silica gel column chromatography eluting with CH₂Cl₂/MeOH to afford 400 mg of the title compound (34% yield over 3 steps).

NMR Spectroscopy: ¹H NMR (300 MHz, CDCl₃): δ 8.06 (d, J=2.4 Hz, 1H), 7.66 (dd, J=8.4 Hz, 2.4 Hz, 1H), 7.43 (t, J=72.3 Hz, 1H), 7.20 (d, J=8.7 Hz, 1H), 6.84 (d, J=7.2 Hz, 1H), 6.25 (d, J=7.2 Hz, 1H), 3.46-3.40 (m, 2H), 3.38-3.28 (m, 1H), 2.79-2.40 (m, 4H), 1.95-1.80 (m, 4H), 1.75-1.62 (m, 4H), 1.40-1.20 (m, 6H). ¹⁹F NMR (282 MHz, CDCl₃): δ -88.3 (d, J=72.5 Hz, 2F).

Example 4. Synthesis of 3-(6-fluoroquinolin-3-yl)-9-(5,6,7,8-tetrahydro-1,8-naphthyridin-2-yl)nonanoic acid (Compound A4)

6-fluoroquinoline-3-carbaldehyde

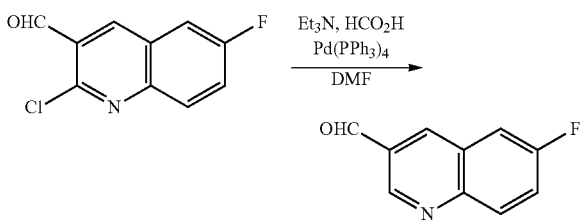

To 2-chloro-6-fluoroquinoline-3-carbaldehyde (2.03 g, 9.68 mmol, 1.00 equiv) in DMF (10 mL) at 23° C. and under an atmosphere of N₂, was added triethylamine (16.2 mL, 116 mmol, 12.0 equiv), Pd(PPh₃)₄ (559 mg, 0.484 mmol, 5.00 mol %), and formic acid (1.29 mL, 34.2 mmol, 5.40 equiv). After stirring for 1 hr at 100° C., the reaction mixture was cooled to 23° C. and water (40 mL) and EtOAc (30 mL) were added. The phases were separated and the aqueous phase was extracted with EtOAc (3×30 mL). The combined organic phases were washed with brine (50 mL), dried (MgSO₄), and filtered. The filtrate was concentrated in vacuo and the residue was purified by silica gel column chromatography eluting with hexanes/EtOAc to afford 734 mg of the title compound (43% yield).

NMR Spectroscopy: ¹H NMR (300 MHz, CDCl₃): δ 10.27 (s, 1H), 9.34 (d, J=2.1 Hz, 1H), 8.60 (d, J=1.8 Hz, 1H), 8.21 (dd, J=9.0 Hz, 4.8 Hz, 1H), 7.70-7.60 (m, 2H). ¹⁹F NMR (282 MHz, CDCl₃): δ -110.8 (m, 1F).

81
(E)-1-(6-fluoroquinolin-3-yl)-7-(5,6,7,8-tetrahydro-1,8-naphthyridin-2-yl)hept-1-en-3-one

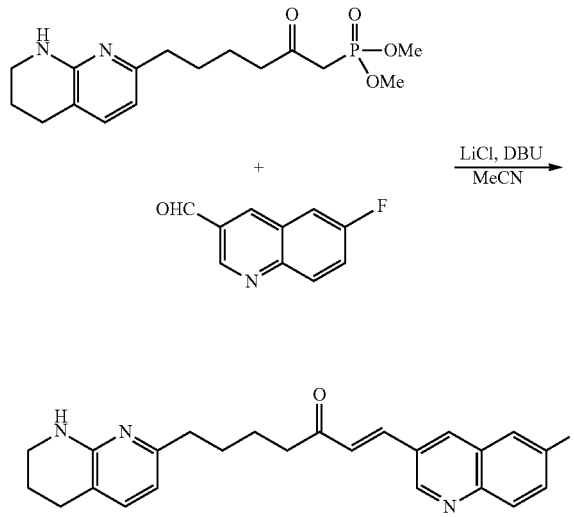

To dimethyl (2-oxo-6-(5,6,7,8-tetrahydro-1,8-naphthyridin-2-yl)hexyl)phosphonate (900 mg, 2.64 mmol, 1.10 equiv) in MeCN (22 mL) at 23° C. and under an atmosphere of N₂, was added 6-fluoroquinoline-3-carbaldehyde (420 mg, 2.40 mmol, 1.00 equiv), LiCl (101 mg, 2.40 mmol, 1.00 equiv) and DBU (0.377 mL, 2.52 mmol, 1.05 equiv). After stirring for 1 hr at 75° C., the reaction mixture was cooled to 23° C. and filtered through a pad of CELITE®. The filtrate was concentrated in vacuo and the residue was purified by silica gel column chromatography eluting with CH₂Cl₂/MeOH to afford 900 mg of the title compound (96% yield).

NMR Spectroscopy: ¹H NMR (300 MHz, CDCl₃): δ 9.06 (d, J=2.4 Hz, 1H), 8.21 (d, J=2.1 Hz, 1H), 8.11 (dd, J=10.6 Hz, 5.7 Hz, 1H), 7.66 (d, J=16.2 Hz, 1H), 7.58-7.43 (m, 2H), 7.06 (d, J=7.2 Hz, 1H), 6.96 (d, J=16.2 Hz, 1H), 6.37 (d, J=7.2 Hz, 1H), 4.76 (br s, 1H), 3.43-3.35 (m, 2H), 2.78-2.65 (m, 4H), 2.63-2.56 (m, 2H), 1.94-1.85 (m, 2H), 1.82-1.66 (m, 4H). ¹⁹F NMR (282 MHz, CDCl₃): δ −111.9 (m, 1F).

82
(E)-1-(6-fluoroquinolin-3-yl)-7-(5,6,7,8-tetrahydro-1,8-naphthyridin-2-yl)hept-1-en-3-ol

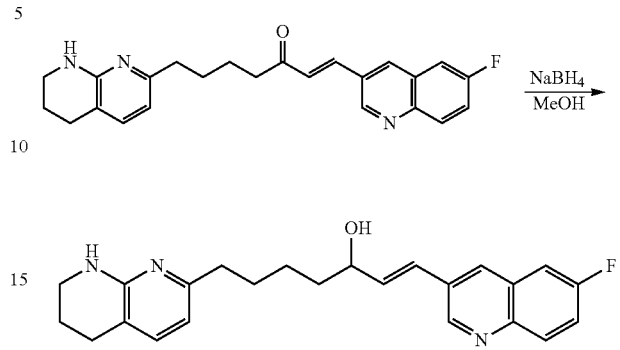

To (E)-1-(6-fluoroquinolin-3-yl)-7-(5,6,7,8-tetrahydro-1,8-naphthyridin-2-yl)hept-1-en-3-one (490 mg, 1.26 mmol, 1.00 equiv) in MeOH (29 mL) at 0° C. and under an atmosphere of air, was added NaBH₄ (71.5 mg, 1.89 mmol, 1.5 equiv). After stirring for 1 hr at 0° C., 1N HCl aq (10 mL) was added and the reaction mixture was then concentrated in vacuo to remove the MeOH. The residue was neutralized with NaHCO₃ aq and EtOAc (10 mL) was added. The phases were separated and the aqueous phase was extracted with EtOAc (3×20 mL). The combined organic phases were washed with brine (30 mL), dried (MgSO₄), and filtered. The filtrate was concentrated in vacuo and the residue was purified by silica gel column chromatography eluting with CH₂Cl₂/MeOH to afford 490 mg of the title compound (99% yield).

NMR Spectroscopy: ¹H NMR (300 MHz, CDCl₃): δ 8.95 (s, 1H), 8.06 (dd, J=10.6 Hz, 5.7 Hz, 1H), 7.99 (s, 1H), 7.50-7.40 (m, 2H), 7.06 (d, J=7.2 Hz, 1H), 6.75 (d, J=16.2 Hz, 1H), 6.49 (dd, J=16.2 Hz, 4.5 Hz, 1H), 6.34 (d, J=7.2 Hz, 1H), 4.94 (br s, 1H), 4.47-4.39 (m, 1H), 3.42-3.38 (m, 2H), 2.70-2.47 (m, 4H), 1.96-1.45 (m, 8H). ¹⁹F NMR (282 MHz, CDCl₃): δ −111.8 (m, 1F).

3-(6-fluoroquinolin-3-yl)-9-(5,6,7,8-tetrahydro-1,8-naphthyridin-2-yl)nonanoic acid (Compound A4)

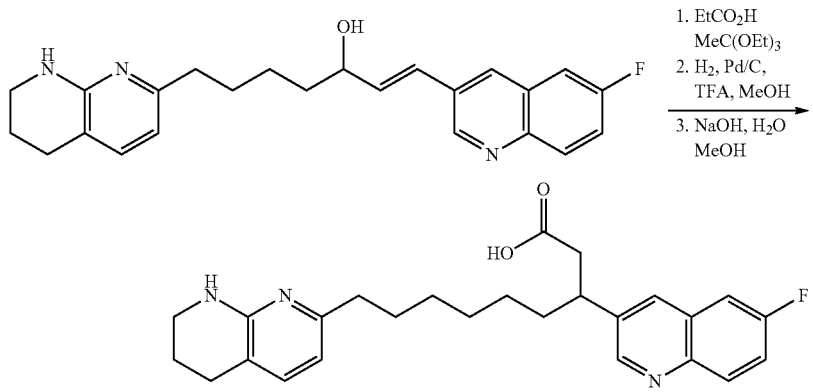

To (E)-1-(6-fluoroquinolin-3-yl)-'7-(5,6,7,8-tetrahydro-1,8-naphthyridin-2-yl)hept-1-en-3-ol (489 mg, 1.25 mmol, 1.00 equiv) in MeC(OEt)$_3$ (12 mL) at 23° C. and under an atmosphere of N$_2$, was added EtCO$_2$H (93.3 µL, 1.25 mmol, 1.00 equiv). After stirring for 2 hr at 140° C., the reaction mixture was purified by silica gel column chromatography eluting with hexanes/EtOAc to afford a crude rearrangement product, which was used in the next step without further purification.

To the above obtained residue in MeOH-TFA (10 mL-1 mL) at 23° C. and under an atmosphere of air, was added 10% Pd/C (128 mg, 0.121 mmol, 9.68 mol %) and H$_2$ gas was introduced into the reaction with a balloon. After stirring for 1 hr at 23° C., the reaction mixture was filtered through a pad of CELITE® and the filtrate was concentrated in vacuo to afford a crude olefin reduction product, which was used in the next step without further purification.

To the above obtained residue in MeOH (10 mL) at 23° C. and under an atmosphere of air, was added 15% NaOH aq (3.0 mL). After stirring for 20 min at 60° C., the reaction mixture was neutralized with 3N HCl and concentrated in vacuo to remove the MeOH. The residual aqueous solution was extracted with EtOAc (3×10 mL) and the combined organic phases were washed with NaHCO$_3$ aq (2×5 mL), dried (MgSO$_4$), and filtered. The filtrate was concentrated in vacuo and the residue was purified by silica gel column chromatography eluting with CH$_2$Cl$_2$/MeOH to afford 500 mg of the title compound (92% yield over 3 steps).

NMR Spectroscopy: $^1$H NMR (300 MHz, CD$_3$OD): δ 8.78 (s, 1H), 8.11 (s, 1H), 8.00-7.93 (m, 1H), 7.52-7.42 (m, 2H), 7.31 (d, J=7.2 Hz, 1H), 6.35 (d, J=7.2 Hz, 1H), 3.38-3.20 (m, 3H), 2.77-2.42 (m, 4H), 1.90-1.20 (m, 14H). $^{19}$F NMR (282 MHz, CD$_3$OD): δ −110.9 (m, 1F).

Example 5. Synthesis of 3-(7-fluoroquinolin-3-yl)-9-(5,6,7,8-tetrahydro-1,8-naphthyridin-2-yl)nonanoic acid (Compound A5)

(E)-1-(7-fluoroquinolin-3-yl)-7-(5,6,7,8-tetrahydro-1,8-naphthyridin-2-yl)hept-1-en-3-one

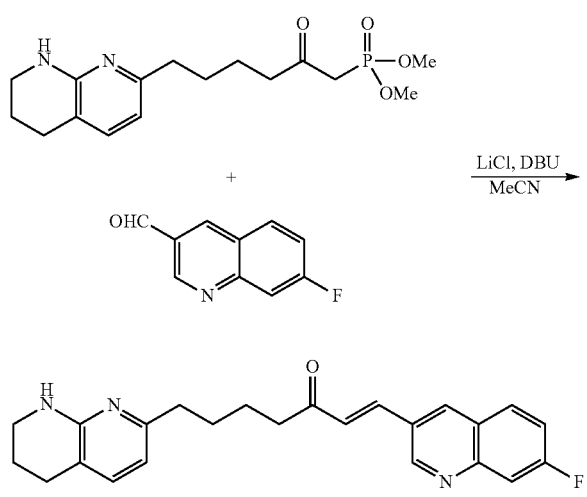

To dimethyl (2-oxo-6-(5,6,7,8-tetrahydro-1,8-naphthyridin-2-yl)hexyl)phosphonate (749 mg, 2.20 mmol, 1.10 equiv) in MeCN (22 mL) at 23° C. and under an atmosphere of N$_2$, was added 7-fluoroquinoline-3-carbaldehyde (350 mg, 2.00 mmol, 1.00 equiv; Sato, I. et al., Synthesis 2004, 9:1419-1428), LiCl (84.8 mg, 2.00 mmol, 1.00 equiv), and DBU (0.314 mL, 2.10 mmol, 1.05 equiv). After stirring for 1 hr at 75° C., the reaction mixture was cooled to 23° C. and then filtered through a pad of CELITE®. The filtrate was concentrated in vacuo and the residue was purified by silica gel column chromatography eluting with CH$_2$Cl$_2$/MeOH to afford 570 mg of the title compound (73% yield).

NMR Spectroscopy: $^1$H NMR (300 MHz, CDCl$_3$\): δ 9.10 (d, J=2.4 Hz, 1H), 8.28 (d, J=2.1 Hz, 1H), 7.87 (dd, J=9.0 Hz, 6.0 Hz, 1H), 7.74 (dd, J=9.9 Hz, 2.4 Hz, 1H), 7.69 (d, J=16.2 Hz, 1H), 7.42-7.33 (m, 1H), 7.11 (d, J=7.2 Hz, 1H), 6.94 (d, J=16.2 Hz, 1H), 6.37 (d, J=7.2 Hz, 1H), 5.41 (br s, 1H), 3.43-3.37 (m, 2H), 2.78-2.58 (m, 6H), 1.93-1.85 (m, 2H), 1.81-1.69 (m, 4H). $^{19}$F NMR (282 MHz, CDCl$_3$\): δ −107.0 (m, 1F).

(E)-1-(7-fluoroquinolin-3-yl)-7-(5,6,7,8-tetrahydro-1,8-naphthyridin-2-yl)hept-1-en-3-ol

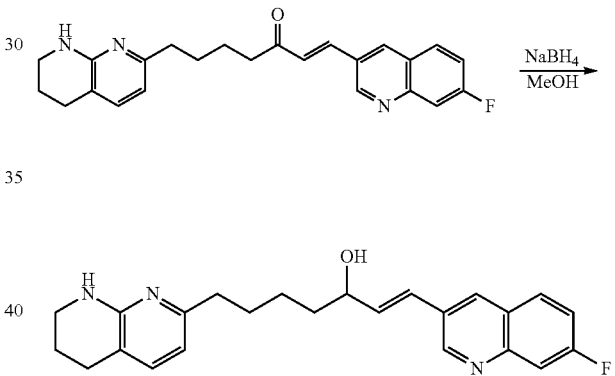

To (E)-1-(7-fluoroquinolin-3-yl)-'7-(5,6,7,8-tetrahydro-1,8-naphthyridin-2-yl)hept-1-en-3-one (300 mg, 0.770 mmol, 1.00 equiv) in MeOH (8 mL) at 0° C. and under an atmosphere of air, was added NaBH$_4$ (87.4 mg, 2.31 mmol, 3.00 equiv). After stirring for 30 min at 0° C., 1N HCl aq (10 mL) was added and the reaction mixture was concentrated in vacuo to remove the MeOH. The resulting residue was neutralized with NaHCO$_3$ aq and EtOAc (10 mL) was then added. The phases were separated and the aqueous phase was extracted with EtOAc (3×20 mL). The combined organic phases were washed with brine (30 mL), dried (MgSO$_4$), and filtered. The filtrate was concentrated in vacuo and the residue was purified by silica gel column chromatography eluting with CH$_2$Cl$_2$/MeOH to afford 210 mg of the title compound (70% yield). NMR Spectroscopy: $^1$H NMR (300 MHz, CDCl$_3$): δ 8.98 (s, 1H), 8.07 (s, 1H), 7.81 (dd, J=9.0 Hz, 6.0 Hz, 1H), 7.78 (dd, J=9.9 Hz, 2.4 Hz, 1H), 7.63 (br s, 1H), 7.39-7.28 (m, 1H), 6.78 (d, J=16.2 Hz, 1H), 6.47 (dd, J=16.2 Hz, 4.5 Hz, 1H), 6.36 (d, J=7.2 Hz, 1H), 4.48-4.41 (m, 1H), 3.48-3.41 (m, 2H), 2.79-2.67 (m, 4H), 1.97-1.48 (m, 8H). $^{19}$F NMR (282 MHz, CDCl$_3$): δ −109.9 (m, 1F).

3-(7-fluoroquinolin-3-yl)-9-(5,6,7,8-tetrahydro-1,8-naphthyridin-2-yl)nonanoic acid (Compound A5)

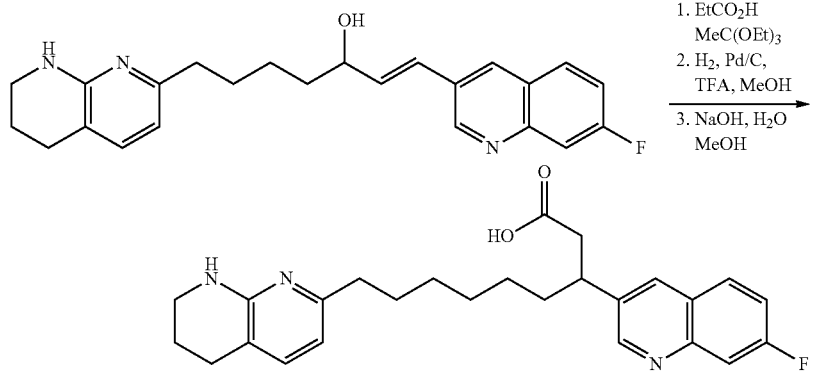

To (E)-1-(7-fluoroquinolin-3-yl)-7-(5,6,7,8-tetrahydro-1,8-naphthyridin-2-yl)hept-1-en-3-ol (730 mg, 1.71 mmol, 1.00 equiv) in MeC(OEt)$_3$ (17 mL) at 23° C. and under an atmosphere of N$_2$, was added EtCO$_2$H (128 μL, 1.71 mmol, 1.00 equiv). After stirring for 2 hr at 140° C., the reaction mixture was directly purified by silica gel column chromatography eluting with hexanes/EtOAc to afford a crude rearrangement product, which was used in the next step without further purification.

To the above obtained residue in MeOH-TFA (10 mL-1 mL) at 23° C. and under an atmosphere of air, was added 10% Pd/C (125 mg, 0.117 mmol, 6.84 mol %) and H$_2$ gas was introduced into the reaction mixture with a balloon. After stirring for 1 hr at 23° C., the reaction mixture was filtered through a pad of CELITE®. The filtrate was concentrated in vacuo to afford a crude olefin reduction product, which was used in the next step without further purification.

To the above obtained residue in MeOH (10 mL) at 23° C. and under an atmosphere of air, was added 15% NaOH aq (3.0 mL). After stirring for 20 min at 60° C., the reaction mixture was neutralized with 3N HCl and then concentrated in vacuo to remove the MeOH. The residual aqueous solution was extracted with EtOAc (3×10 mL) and the combined organic phases were washed with NaHCO$_3$ aq (2×5 mL), dried (MgSO$_4$), and filtered. The filtrate was concentrated in vacuo and the residue was purified by silica gel column chromatography eluting with CH$_2$Cl$_2$/MeOH to afford 480 mg of the title compound (64% yield over 3 steps).

NMR Spectroscopy: $^1$H NMR (300 MHz, CD$_3$OD): δ 8.79 (s, 1H), 8.21 (s, 1H), 8.00-7.91 (m, 1H), 7.62-7.57 (m, 1H), 7.48-7.38 (m, 2H), 6.47 (d, J=7.2 Hz, 1H), 3.48-3.30 (m, 3H), 2.80-2.52 (m, 4H), 1.90-1.20 (m, 14H). $^{19}$F NMR (282 MHz, CD$_3$OD): δ −111.9 (m, 1F).

Example 6. Synthesis of 3-(6,7-difluoroquinolin-3-yl)-9-(5,6,7,8-tetrahydro-1,8-naphthyridin-2-yl)nonanoic acid (Compound A6)

6,7-difluoroquinoline-3-carbaldehyde

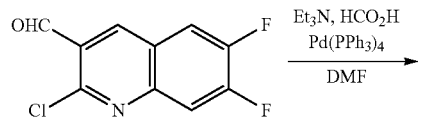

-continued

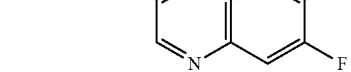

To 2-chloro-6,7-difluoroquinoline-3-carbaldehyde (1.44 g, 6.33 mmol, 1.00 equiv) in DMF (6.3 mL) at 23° C. and under an atmosphere of N$_2$, was added triethylamine (10.6 mL, 76.0 mmol, 12.0 equiv), Pd(PPh$_3$)$_4$ (366 mg, 0.317 mmol, 5.00 mol %), and formic acid (1.29 mL, 34.2 mmol, 5.40 equiv). After stirring for 1 hr at 100° C., the reaction mixture was cooled to 23° C. and water (30 mL) and EtOAc (20 mL) was added. The phases were separated and the aqueous phase was extracted with EtOAc (3×20 mL). The combined organic phases were washed with brine (50 mL), dried (MgSO$_4$), and filtered. The filtrate was concentrated in vacuo and the residue was purified by silica gel column chromatography eluting with hexanes/EtOAc to afford 500 mg of the title compound (41% yield).

NMR Spectroscopy: $^1$H NMR (300 MHz, CDCl$_3$): δ 10.26 (s, 1H), 9.35 (d, J=1.2 Hz, 1H), 8.60 (d, J=1.5 Hz, 1H), 7.97 (dd, J=10.8 Hz, 7.5 Hz, 1H), 7.97 (dd, J=9.0 Hz, 8.7 Hz, 1H). $^{19}$F NMR (282 MHz, CDCl$_3$): δ −125.3 (m, 1F), −132.3 (m, 1F).

(E)-1-(6,7-difluoroquinolin-3-yl)-7-(5,6,7,8-tetrahydro-1,8-naphthyridin-2-yl)hept-1-en-3-one

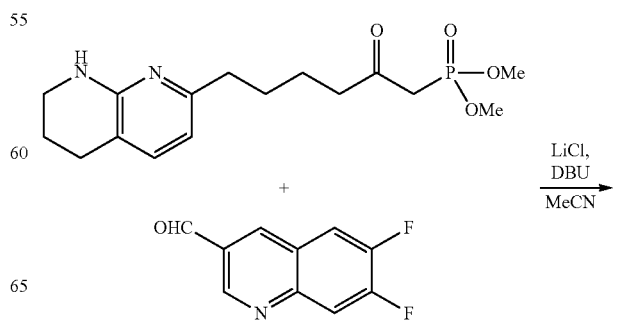

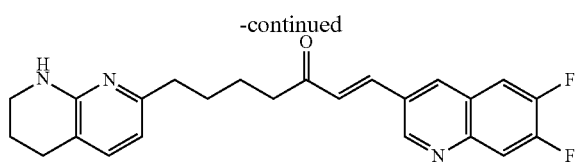

To dimethyl (2-oxo-6-(5,6,7,8-tetrahydro-1,8-naphthyridin-2-yl)hexyl)phosphonate (599 mg, 1.76 mmol, 1.10 equiv) in MeCN (5 mL) at 23° C. and under an atmosphere of N₂, was added 6,7-difluoroquinoline-3-carbaldehyde (310 mg, 1.60 mmol, 1.00 equiv), LiCl (67.8 mg, 1.60 mmol, 1.00 equiv), and DBU (0.251 mL, 1.68 mmol, 1.05 equiv). After stirring for 1 hr at 75° C., the reaction mixture was cooled to 23° C. and then filtered through a pad of CELITE®. The filtrate was concentrated in vacuo and the residue was purified by silica gel column chromatography eluting with CH₂Cl₂/MeOH to afford 570 mg of the title compound (84% yield).

NMR Spectroscopy: ¹H NMR (300 MHz, CDCl₃): δ 9.07 (d, J=2.4 Hz, 1H), 8.20 (d, J=2.1 Hz, 1H), 7.87 (dd, J=10.8 Hz, 7.5 Hz, 1H), 7.66 (d, J=16.2 Hz, 1H), 7.62-7.53 (m, 1H), 7.06 (d, J=7.2 Hz, 1H), 6.93 (d, J=16.2 Hz, 1H), 6.36 (d, J=7.2 Hz, 1H), 4.77 (br s, 1H), 3.43-3.38 (m, 2H), 2.79-2.58 (m, 6H), 1.96-1.85 (m, 2H), 1.81-1.69 (m, 4H). ¹⁹F NMR (282 MHz, CDCl₃): δ −129.1 (m, 1F), −133.6 (m, 1F).

(E)-1-(6,7-difluoroquinolin-3-yl)-7-(5,6,7,8-tetrahydro-1,8-naphthyridin-2-yl)hept-1-en-3-ol

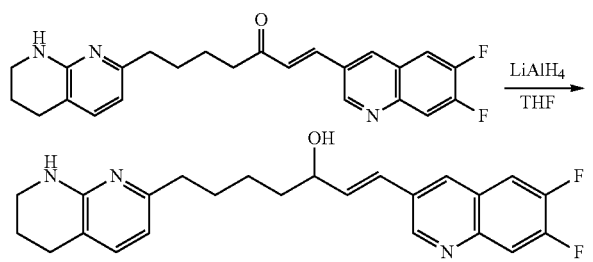

To (E)-1-(6,7-difluoroquinolin-3-yl)-7-(5,6,7,8-tetrahydro-1,8-naphthyridin-2-yl)hept-1-en-3-one (1.03 g, 2.53 mmol, 1.00 equiv) in THF (25 mL) at 0° C. and under an atmosphere of N₂, was added LiAlH₄ (1.0 M in THF, 2.53 mL, 2.53 mmol, 1.00 equiv). After stirring for 10 min at 0° C., H₂O (96 μL), 15% NaOH aq (96 μL), and H₂O (288 μL) were added sequentially. The reaction mixture was warmed to 23° C. and then filtered through a pad of CELITE®. The filtrate was concentrated in vacuo and the residue was purified by silica gel column chromatography eluting with CH₂Cl₂/MeOH to afford 780 mg of the title compound (75% yield).

NMR Spectroscopy: ¹H NMR (300 MHz, CDCl₃): δ 8.95 (d, J=2.4 Hz, 1H), 8.00 (d, J=2.1 Hz, 1H), 7.81 (dd, J=10.8 Hz, 7.5 Hz, 1H), 7.52 (d, J=16.2 Hz, 1H), 7.21 (d, J=7.2 Hz, 1H), 6.76 (d, J=16.2 Hz, 1H), 6.48 (dd, J=16.2 Hz, 4.5 Hz, 1H), 6.34 (d, J=7.2 Hz, 1H), 4.48-4.42 (m, 1H), 3.47-3.41 (m, 2H), 2.79-2.67 (m, 4H), 1.97-1.47 (m, 8H). ¹⁹F NMR (282 MHz, CDCl₃): δ −132.1 (m, 1F), −135.1 (m, 1F).

3-(6,7-difluoroquinolin-3-yl)-9-(5,6,7,8-tetrahydro-1,8-naphthyridin-2-yl)nonanoic acid (Compound A6)

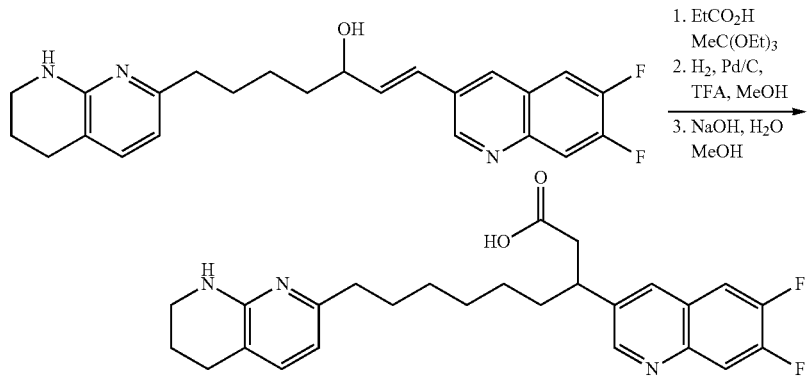

To (E)-1-(6,7-difluoroquinolin-3-yl)-7-(5,6,7,8-tetrahydro-1,8-naphthyridin-2-yl)hept-1-en-3-ol (780 mg, 1.90 mmol, 1.00 equiv) in MeC(OEt)₃ (19 mL) at 23° C. and under an atmosphere of N₂, was added EtCO₂H (142 μL, 1.90 mmol, 1.00 equiv). After stirring for 2 hr at 140° C., the reaction mixture was purified by silica gel column chromatography eluting with hexanes/EtOAc to afford a crude rearrangement product, which was used in the next step without further purification.

To the above obtained residue in MeOH-TFA (10 mL-1 mL) at 23° C. and under an atmosphere of air, was added 10% Pd/C (127 mg, 0.119 mmol, 6.26 mol %) and H₂ gas was introduced into the reaction with a balloon. After stirring for 1 hr at 23° C., the reaction mixture was filtered through a pad of CELITE®. The filtrate was concentrated in vacuo to afford a crude olefin reduction product, which was used in the next step without further purification.

To the above obtained residue in MeOH (10 mL) at 23° C. and under an atmosphere of air, was added 15% NaOH aq (3.2 mL). After stirring for 20 min at 60° C., the reaction mixture was neutralized with 3N HCl and then concentrated in vacuo to remove the MeOH. The residual aqueous solution was extracted with EtOAc (3×10 mL) and the combined organic phases were washed with NaHCO₃ aq (2×5 mL), dried (MgSO₄), and filtered. The filtrate was concentrated in vacuo and the residue was purified by silica gel column chromatography eluting with CH₂Cl₂/MeOH to afford 500 mg of the title compound (58% yield over 3 steps).

NMR Spectroscopy: $^1$H NMR (300 MHz, CDCl$_3$): δ 8.79 (s, 1H), 7.97 (s, 1H), 7.90-7.81 (m, 1H), 7.58-7.47 (m, 1H), 7.24 (d, J=7.2 Hz, 1H), 6.23 (d, J=7.2 Hz, 1H), 3.48-3.32 (m, 3H), 2.80-2.57 (m, 4H), 1.95-1.20 (m, 14H). $^{19}$F NMR (282 MHz, CDCl$_3$): δ −132.3 (m, 1F), −135.5 (m, 1F).

Example 7. Synthesis of 9-(5,6,7,8-tetrahydro-1,8-naphthyridin-2-yl)-3-(7-(trifluoromethyl)quinolin-3-yl)nonanoic acid (Compound A7)

2-chloro-7-iodoquinoline-3-carbaldehyde

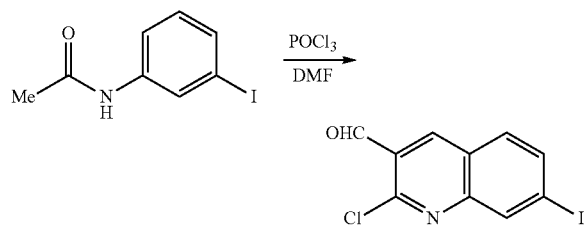

To POCl$_3$ (14.9 mL, 160 mmol, 7.00 equiv) at 0° C. and under an atmosphere of N$_2$, was added DMF (4.40 mL, 57.1 mmol, 2.50 equiv). After stirring for 10 min at 0° C., N-(3-iodophenyl)acetamide (5.96 g, 22.8 mmol, 1.00 equiv; Pialat, A. et al., *Org. Lett.* 2013, 15:1764-1767) was added. After stirring for 17 hr at 75° C., the reaction mixture was poured into ice. The phases were separated and the aqueous phase was extracted with CH$_2$Cl$_2$ (3×50 mL). The combined organic phases were washed with brine (100 mL), dried (MgSO$_4$), and filtered. The filtrate was concentrated in vacuo and the residue was purified by silica gel column chromatography eluting with CH$_2$Cl$_2$/MeOH to afford 2.9 g of the title compound (40% yield).

NMR Spectroscopy: $^1$H NMR (300 MHz, CDCl$_3$): δ 10.55 (s, 1H), 8.72 (s, 1H), 8.52 (s, 1H), 7.93 (dd, J=8.4 Hz, 1.5 Hz, 1H), 7.69 (d, J=8.4 Hz, 1H).

2-chloro-7-(trifluoromethyl)quinoline-3-carbaldehyde

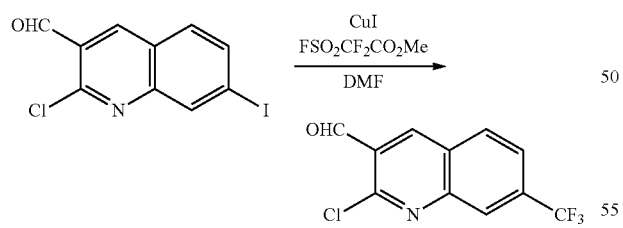

To 2-chloro-7-iodoquinoline-3-carbaldehyde (2.90 g, 9.13 mmol, 1.00 equiv) in DMF (18 mL) at 23° C. and under an atmosphere of N$_2$, was added CuI (4.35 g, 22.8 mmol, 2.50 equiv) and FSO$_2$CF$_2$CO$_2$Me (11.6 mL, 91.3 mmol, 10.0 equiv). After stirring for 2 hr at 95° C., the reaction mixture was cooled to 23° C. and filtered through a pad of CELITE®. The filtrate was concentrated in vacuo and the residue was purified by silica gel column chromatography eluting with hexanes/EtOAc to afford 1.5 g of the title compound (63% yield).

NMR Spectroscopy: $^1$H NMR (300 MHz, CDCl$_3$): δ 10.60 (s, 1H), 8.82 (s, 1H), 8.39 (s, 1H), 8.14 (d, J=8.4 Hz, 1H), 7.84 (d, J=8.4 Hz, 1H). $^{19}$F NMR (282 MHz, CDCl$_3$): δ −63.2 (s, 3F).

7-(trifluoromethyl)quinoline-3-carbaldehyde

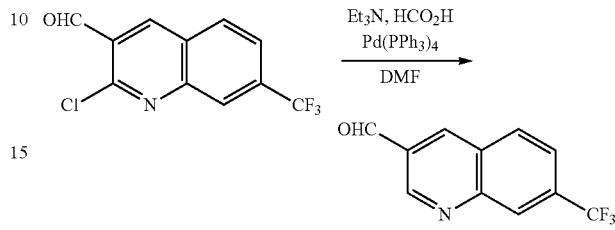

To 2-chloro-7-(trifluoromethyl)quinoline-3-carbaldehyde (1.50 g, 5.78 mmol, 1.00 equiv) in DMF (5.8 mL) at 23° C. and under an atmosphere of N$_2$, was added triethylamine (9.67 mL, 69.4 mmol, 12.0 equiv), Pd(PPh$_3$)$_4$ (334 mg, 0.289 mmol, 5.00 mol %), and formic acid (1.18 mL, 31.2 mmol, 5.40 equiv). After stirring for 1 hr at 100° C., the reaction mixture was cooled to 23° C. and water (30 mL) and EtOAc (20 mL) were added. The phases were separated and the aqueous phase was extracted with EtOAc (3×20 mL). The combined organic phases were washed with brine (50 mL), dried (MgSO$_4$), and filtered. The filtrate was concentrated in vacuo and the residue was purified by silica gel column chromatography eluting with hexanes/EtOAc to afford 412 mg of the title compound (32% yield).

NMR Spectroscopy: $^1$H NMR (300 MHz, CDCl$_3$): δ 10.32 (s, 1H), 9.48 (d, J=1.5 Hz, 1H), 8.71 (d, J=1.5 Hz, 1H), 8.51 (s, 1H), 8.15 (d, J=8.4 Hz, 1H), 7.86 (d, J=8.4 Hz, 1H). $^{19}$F NMR (282 MHz, CDCl$_3$): δ −63.1 (s, 3F).

(E)-7-(5,6,7,8-tetrahydro-1,8-naphthyridin-2-yl)-1-(7-(trifluoromethyl)quinolin-3-yl)hept-1-en-3-one

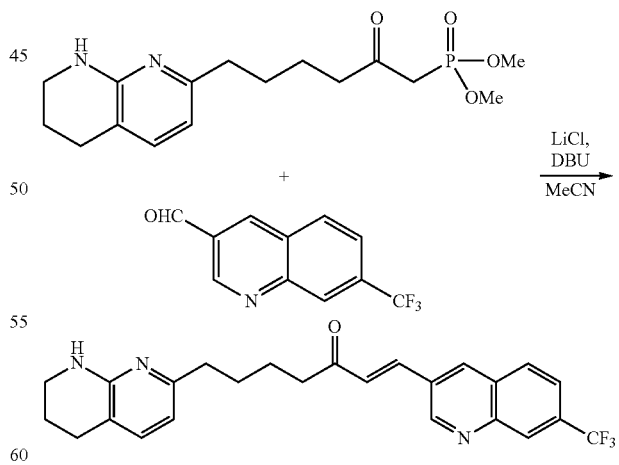

To dimethyl (2-oxo-6-(5,6,7,8-tetrahydro-1,8-naphthyridin-2-yl)hexyl)phosphonate (685 mg, 2.01 mmol, 1.10 equiv) in MeCN (9 mL) at 23° C. and under an atmosphere of N$_2$, was added 7-(trifluoromethyl)quinoline-3-carbaldehyde (412 mg, 1.83 mmol, 1.00 equiv), LiCl (77.6 mg, 1.83 mmol, 1.00 equiv), and DBU (0.287 mL, 1.92 mmol, 1.05 equiv). After stirring for 1 hr at 75° C., the reaction mixture was cooled to 23° C. and then filtered through a pad of CELITE®. The filtrate was concentrated in vacuo and the residue was purified by silica gel column chromatography eluting with CH₂Cl₂/MeOH to afford 706 mg of the title compound (88% yield).

NMR Spectroscopy: ¹H NMR (300 MHz, CDCl₃): δ 9.19 (d, J=2.4 Hz, 1H), 8.42 (d, J=2.1 Hz, 1H), 8.31 (d, J=2.1 Hz, 1H), 8.00 (d, J=9.0 Hz, 1H), 7.79 (d, J=9.0 Hz, 1H), 7.69 (d, J=16.2 Hz, 1H), 7.04 (d, J=7.2 Hz, 1H), 6.99 (d, J=16.2 Hz, 1H), 6.37 (d, J=7.2 Hz, 1H), 4.78 (br s, 1H), 3.41-3.37 (m, 2H), 2.80-2.58 (m, 6H), 1.93-1.85 (m, 2H), 1.81-1.69 (m, 4H). ¹⁹F NMR (282 MHz, CDCl₃): δ −62.8 (s, 3F).

(E)-7-(5,6,7,8-tetrahydro-1,8-naphthyridin-2-yl)-1-(7-(trifluoromethyl)quinolin-3-yl)hept-1-en-3-ol

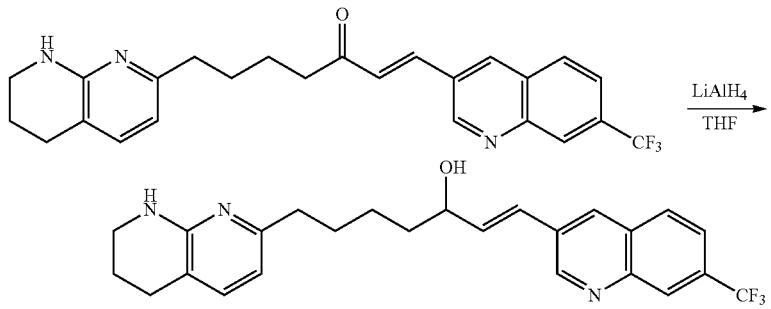

To (E)-7-(5,6,7,8-tetrahydro-1,8-naphthyridin-2-yl)-1-(7-(trifluoromethyl)quinolin-3-yl)hept-1-en-3-one (705 mg, 1.60 mmol, 1.00 equiv) in THF (16 mL) at 0° C. and under an atmosphere of N₂, was added LiAlH₄ (1.0 M in THF, 1.60 mL, 1.60 mmol, 1.00 equiv). After stirring for 10 min at 0° C., H₂O (54 μL), 15% NaOH aq (54 μL), and H₂O (162 μL) were added sequentially. The reaction mixture was warmed to 23° C. and then filtered through a pad of CELITE®. The filtrate was concentrated in vacuo and the residue was purified by silica gel column chromatography eluting with CH₂Cl₂/MeOH to afford 515 mg of the title compound (73% yield).

NMR Spectroscopy: ¹H NMR (300 MHz, CDCl₃): δ 9.08 (d, J=2.4 Hz, 1H), 8.37 (d, J=2.1 Hz, 1H), 8.08 (d, J=2.1 Hz, 1H), 7.91 (d, J=9.0 Hz, 1H), 7.71 (d, J=9.0 Hz, 1H), 7.06 (d, J=7.2 Hz, 1H), 6.79 (d, J=16.2 Hz, 1H), 6.53 (dd, J=16.2 Hz, 4.5 Hz, 1H), 6.34 (d, J=7.2 Hz, 1H), 4.89 (br s, 1H), 4.48-4.40 (m, 1H), 3.43-3.37 (m, 2H), 2.75-2.57 (m, 4H), 1.97-1.42 (m, 8H). ¹⁹F NMR (282 MHz, CDCl₃): δ −62.6 (s, 3F).

9-(5,6,7,8-tetrahydro-1,8-naphthyridin-2-yl)-3-(7-(trifluoromethyl)quinolin-3-yl)nonanoic acid (Compound A7)

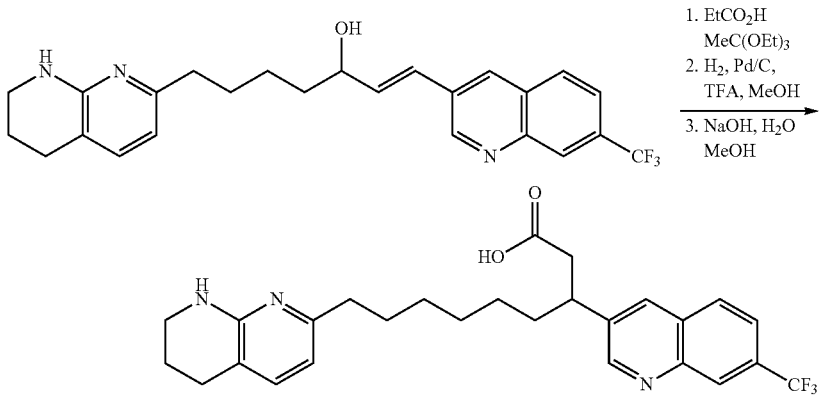

To (E)-7-(5,6,7,8-tetrahydro-1,8-naphthyridin-2-yl)-1-(7-(trifluoromethyl)quinolin-3-yl)hept-1-en-3-ol (515 mg, 1.17 mmol, 1.00 equiv) in MeC(OEt)₃ (12 mL) at 23° C. and under an atmosphere of N₂, was added EtCO₂H (87.3 µL, 1.17 mmol, 1.00 equiv). After stirring for 2 hr at 140° C., the reaction mixture was purified by silica gel column chromatography eluting with hexanes/EtOAc to afford a crude rearrangement product, which was used in the next step without further purification.

To the above obtained residue in MeOH-TFA (10 mL-1 mL) at 23° C. and under an atmosphere of air, was added 10% Pd/C 66.6 mg, 0.0626 mmol, 5.35 mol %) and H₂ gas was introduced into the reaction mixture with a balloon. After stirring for 1 hr at 23° C., the reaction mixture was filtered through a pad of CELITE®. The filtrate was concentrated in vacuo to afford a crude olefin reduction product, which was used in the next step without further purification.

To the above obtained residue in MeOH (10 mL) at 23° C. and under an atmosphere of air, was added 15% NaOH aq (4.4 mL). After stirring for 20 min at 60° C., the reaction mixture was neutralized with 3N HCl and concentrated in vacuo to remove the MeOH. The residual aqueous solution was extracted with EtOAc (3×10 mL) and the combined organic phases were washed with NaHCO₃ aq (2×5 mL), dried (MgSO₄), and filtered. The filtrate was concentrated in vacuo and the residue was purified by silica gel column chromatography eluting with CH₂Cl₂/MeOH to afford 300 mg of the title compound (53% yield over 3 steps).

NMR Spectroscopy: ¹H NMR (300 MHz, CDCl₃): δ 8.93 (s, 1H), 8.40 (s, 1H), 8.03 (s, 1H), 7.91 (d, J=9.0 Hz, 1H), 7.70 (d, J=9.0 Hz, 1H), 7.24 (d, J=7.2 Hz, 1H), 6.23 (d, J=7.2 Hz, 1H), 3.48-3.40 (m, 3H), 2.80-2.59 (m, 4H), 1.95-1.20 (m, 14H). ¹⁹F NMR (282 MHz, CDCl₃): δ −62.7 (s, 3F).

Example 8. Synthesis of 3-(4-chloro-3-(trifluoromethyl)phenyl)-9-(5,6,7,8-tetrahydro-1,8-naphthyridin-2-yl)nonanoic acid (Compound A23)

Compound A23 was made according to the synthesis scheme as shown in Scheme 3-1.

(E)-1-(4-chloro-3-(trifluoromethyl)phenyl)-7-(5,6,7, 8-tetrahydro-1,8-naphthyridin-2-yl)hept-1-en-3-one

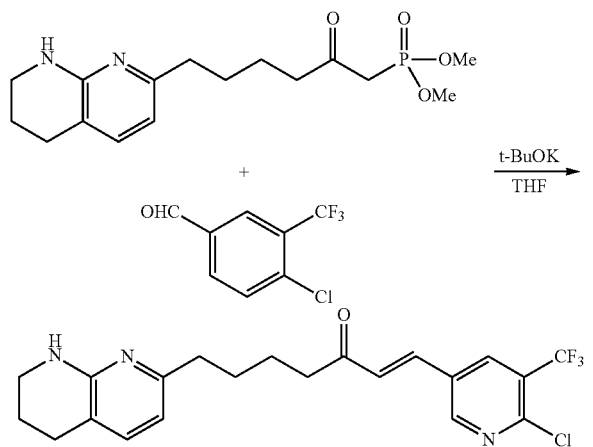

To dimethyl (2-oxo-6-(5,6,7,8-tetrahydro-1,8-naphthyridin-2-yl)hexyl)phosphonate (1.70 g, 5.00 mmol, 1.00 equiv) in THF (10 mL) at 23° C. and under an atmosphere of N₂, was added 4-chloro-3-(trifluoromethyl)benzaldehyde (1.09 g, 5.25 mmol, 1.5 equiv) and t-BuOK (533 mg, 4.75 mmol, 0.950 equiv). After stirring for 10 min at 23° C., water (15 mL) and EtOAc (20 mL) were added to the reaction mixture. The phases were separated and the aqueous phase was extracted with EtOAc (3×10 mL). The combined organic phases were washed with brine (30 mL), dried (MgSO₄), and filtered. The filtrate was concentrated in vacuo and the residue was purified by silica gel column chromatography eluting with CH₂Cl₂/MeOH to afford 1.90 g of the title compound (90% yield).

NMR Spectroscopy: ¹H NMR (300 MHz, CDCl₃): δ 7.81 (s, 1H), 7.61 (d, J=9.1 Hz, 1H), 7.55 (d, J=9.1 Hz, 1H), 7.48 (d, J=16.2 Hz, 1H), 7.04 (d, J=7.2 Hz, 1H), 6.75 (d, J=16.2 Hz, 1H), 6.36 (d, J=7.2 Hz, 1H), 4.96 (br s, 1H), 3.79-3.70 (m, 2H), 3.41-3.37 (m, 2H), 2.73-2.55 (m, 6H), 1.97-1.70 (m, 4H). ¹⁹F NMR (282 MHz, CDCl₃): δ −62.9 (s, 3F)

(E)-1-(4-chloro-3-(trifluoromethyl)phenyl)-7-(5,6,7, 8-tetrahydro-1,8-naphthyridin-2-yl)hept-1-en-3-ol

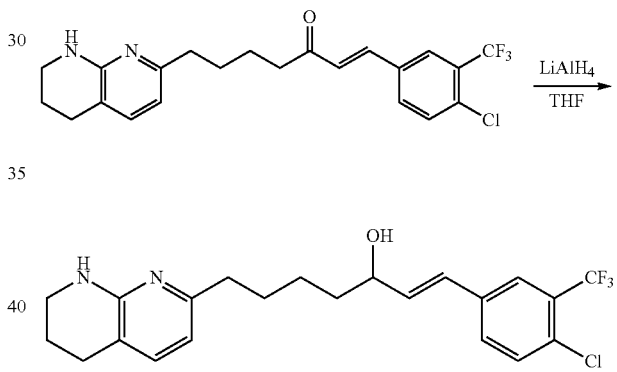

To (E)-1-(4-chloro-3-(trifluoromethyl)phenyl)-7-(5,6,7,8-tetrahydro-1,8-naphthyridin-2-yl)hept-1-en-3-one (1.90 g, 4.50 mmol, 1.00 equiv) in THF (25 mL) at −78° C. and under an atmosphere of N₂, was added LiAlH₄ (1.0 M in THF, 4.5 mL, 4.5 mmol, 1.0 equiv). After stirring for 10 min at −78° C., H₂O (171 µL), 15% NaOH aq (171 µL), and H₂O (513 µL) were added sequentially. The reaction mixture was warmed to 23° C. and then filtered through a pad of celite. The filtrate was concentrated in vacuo and the residue was purified by silica gel column chromatography eluting with CH₂Cl₂/MeOH to afford 800 mg of the title compound (42% yield).

NMR Spectroscopy: ¹H NMR (300 MHz, CDCl₃): δ 7.66 (s, 1H), 7.46-7.40 (m, 2H), 7.07 (d, J=7.2 Hz, 1H), 6.57 (d, J=16.2 Hz, 1H), 6.33 (d, J=7.2 Hz, 1H), 6.28 (dd, J=16.2 Hz, 6.0 Hz, 1H), 5.07 (br s, 1H), 4.40-4.30 (m, 1H), 3.40-3.33 (m, 2H), 2.82 (br s, 1H), 2.70-2.55 (m, 4H), 1.93-1.40 (m, 8H). ¹⁹F NMR (282 MHz, CDCl₃): δ −62.6 (s, 3F).

3-(4-chloro-3-(trifluoromethyl)phenyl)-9-(5,6,7,8-tetrahydro-1,8-naphthyridin-2-yl)nonanoic acid

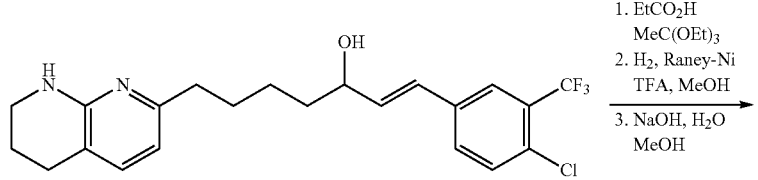

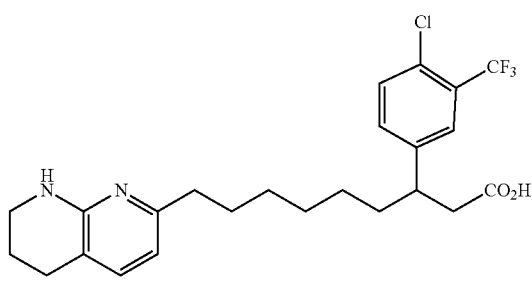

To (E)-1-(4-chloro-3-(trifluoromethyl)phenyl)-7-(5,6,7,8-tetrahydro-1,8-naphthyridin-2-yl)hept-1-en-3-ol (800 mg, 1.88 mmol, 1.00 equiv) in MeC(OEt)₃ (19 mL) at 23° C. and under an atmosphere of N₂, was added EtCO₂H (140 µL, 1.88 mmol, 1.00 equiv). After stirring for 2 hr at 140° C., the reaction mixture was directly purified by silica gel column chromatography eluting with hexanes/EtOAc to afford a crude rearrangement product, which was used in the next step without further purification.

To the above obtained residue in MeOH-TFA (10 mL-1 mL) at 23° C. and under an atmosphere of air, was added Raney®-Nickel (W.R. Grace and Co. Raney® 2800, slurry, in H₂O, active catalyst; 10 drops) and H₂ gas was introduced into the reaction with a balloon. After stirring for 3 hr at 23° C., the reaction mixture was filtered through a pad of celite. The filtrate was concentrated in vacuo to afford a crude olefin reduction product, which was used in the next step without further purification.

To the above obtained residue in MeOH (10 mL) at 23° C. and under an atmosphere of air, was added 15% NaOH aq (3.2 mL). After stirring for 20 min at 60° C., the reaction mixture was neutralized with 3N HCl and then concentrated in vacuo to remove the MeOH. The residual aqueous solution was extracted with EtOAc (3×10 mL) and the combined organic phases were washed with K₂CO₃ aq (2×5 mL), dried (MgSO₄), and filtered. The filtrate was concentrated in vacuo and the residue was purified by silica gel column chromatography eluting with CH₂Cl₂/MeOH to afford 300 mg of the title compound (34% yield over 3 steps).

NMR Spectroscopy: ¹H NMR (300 MHz, CDCl₃): δ 7.54 (s, 1H), 7.39 (d, J=9.1 Hz, 1H), 7.33 (d, J=9.1 Hz, 1H), 7.21 (d, J=7.2 Hz, 1H), 6.25 (d, J=7.2 Hz, 1H), 3.51-3.30 (m, 3H), 2.82-2.42 (m, 6H), 1.98-1.20 (m, 12H). ¹⁹F NMR (282 MHz, CDCl₃): δ −62.4 (s, 3F).

Example 9. Synthesis of 3-(3-chloro-5-(trifluoromethyl)phenyl)-9-(5,6,7,8-tetrahydro-1,8-naphthyridin-2-yl)nonanoic acid (Compound A24)

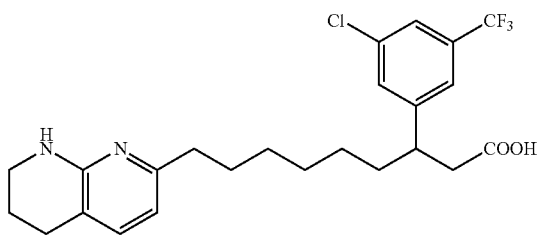 [SMILES: O=C(O)CC(CCCCCCc1ccc2c(n1)NCCC2)c1cc(Cl)cc(C(F)(F)F)c1]

NMR Spectroscopy: ¹H NMR (300 MHz, CDCl₃): δ 7.41-7.35 (m, 3H), 7.20 (d, J=7.2 Hz, 1H), 6.23 (d, J=7.2 Hz, 1H), 3.48-3.39 (m, 2H), 3.35-3.22 (m, 1H), 2.79-2.48 (m, 6H), 1.95-1.18 (m, 12H). ¹⁹F NMR (282 MHz, CDCl₃): δ −62.7 (s, 3F).

Example 10. Synthesis of 3-(3-chloro-5-(trifluoromethyl)phenyl)-9-(5,6,7,8-tetrahydro-1,8-naphthyridin-2-yl)nonanoic acid (Compound A28)

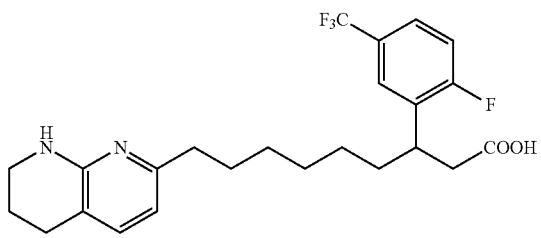 [SMILES: O=C(O)CC(CCCCCCc1ccc2c(n1)NCCC2)c1cc(C(F)(F)F)ccc1F]

NMR Spectroscopy: $^1$H NMR (300 MHz, CDCl$_3$): δ 7.51 (d, J=6.3 Hz, 1H), 7.47-7.40 (m, 1H), 7.20 (d, J=7.2 Hz, 1H), 7.09 (dd, J=9.0 Hz, 9.0 Hz, 1H), 6.24 (d, J=7.2 Hz, 1H), 3.79-3.62 (m, 1H), 3.49-3.39 (m, 2H), 2.84-2.49 (m, 6H), 1.98-1.21 (m, 12H). $^{19}$F NMR (282 MHz, CDCl$_3$): δ −61.8 (s, 3F), −111.9 (s, 1H).

Example 11. Synthesis of 3-(3-chloro-5-(trifluoromethyl)phenyl)-9-(5,6,7,8-tetrahydro-1,8-naphthyridin-2-yl)nonanoic acid (Compound A21)

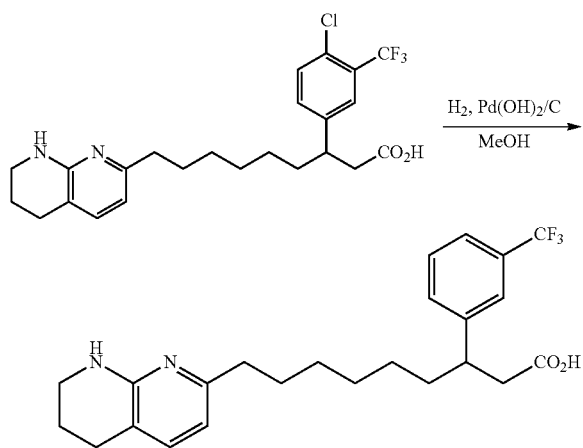

To 3-(4-chloro-3-(trifluoromethyl)phenyl)-9-(5,6,7,8-tetrahydro-1,8-naphthyridin-2-yl)nonanoic acid (1) (100 mg, 0.213 mmol, 1.00 equiv) in MeOH (10 mL) at 23° C. and under an atmosphere of N$_2$, was added 20% palladium hydroxide on carbon (30 mg, 0.043 mmol, 0.20 equiv) and H$_2$ gas was introduced into the reaction mixture with a balloon. After stirring for 3 hr at 23° C., the reaction mixture was filtered through a pad of celite. The filtrate was concentrated in vacuo and the residue was purified by silica gel column chromatography eluting with CH$_2$Cl$_2$/MeOH to afford 50 mg of the title compound (54% yield).

NMR Spectroscopy: $^1$H NMR (300 MHz, CDCl$_3$): δ 7.50-7.30 (m, 4H), 7.25 (d, J=7.2 Hz, 1H), 6.27 (d, J=7.2 Hz, 1H), 3.56-3.41 (m, 2H), 3.37-3.20 (m, 1H), 2.79-2.52 (m, 6H), 1.98-1.18 (m, 12H). $^{19}$F NMR (282 MHz, CDCl$_3$): δ −62.4 (s, 3F).

Example 12. Synthesis of (S)-3-(6-(difluoromethoxy)-pyridine-3-yl)-3-(2-oxo-3-(3-(5,6,7,8-tetrahydro-1,8-naphthyridin-2-yl)propyl)imidazolidin-1-yl) propanoic acid (Compound A15s)

Compound A15s was made according to the synthesis scheme as shown in Scheme 4.

(E)-tert-butyl 3-(4-chloro-3-(trifluoromethyl)phenyl) acrylate

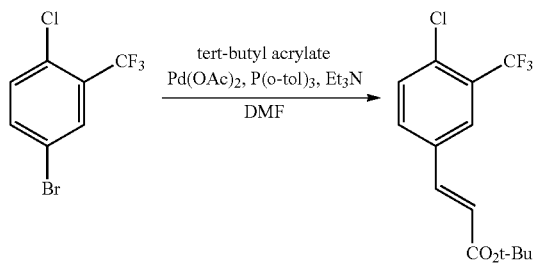

To 4-bromo-1-chloro-2-(trifluoromethyl)benzene (5.19 g, 20.0 mmol, 1.00 equiv) in DMF (10 mL) at 23° C. and under an atmosphere of air, was added tert-butyl acrylate (14.7 mL, 100 mmol, 5.00 equiv), Pd(OAc)$_2$ (269 mg, 1.20 mmol, 6.00 mol %), P(o-tol)$_3$ (730 mg, 2.40 mmol, 12.0 mol %), and Et$_3$N (8.37 mL, 60.0 mmol, 3.00 equiv). After stirring for 6 hr at 110° C., the reaction mixture was cooled to 23° C., filtered, and the filter cake was rinsed with Et$_2$O. The combined filtrate was concentrated, after which EtOAc (100 mL) and water (100 mL) were added to the residue. The phases were separated and the organic phase was washed with water (2×100 mL). The organic phase was dried (MgSO$_4$) and the filtrate was concentrated in vacuo. The residue was purified by silica gel column chromatography eluting with hexanes/EtOAc to afford 6.00 g of the title compound (98% yield).

NMR Spectroscopy: $^1$H NMR (300 MHz, CDCl$_3$): δ 7.80 (s, 1H), 7.61-7.43 (m, 3H), 6.40 (d, J=16.2 Hz, 1H), 1.53 (s, 9H). $^{19}$F NMR (282 MHz, CDCl$_3$): δ −63.0 (s, 3F).

(S)-tert-butyl 3-(benzyl((R)-1-phenylethyl)amino)-3-(4-chloro-3-(trifluoromethyl)phenyl)propanoate To (R)—N-benzyl-1-phenylethanamine (6.12 mL, 29.3 mmol, 1.50 equiv) in THF (90 mL) at 0° C. and under an atmosphere of N$_2$, was added i-PrMgCl (2.0 M in Et$_2$O, 29.3 mL, 58.5 mmol, 3.00 equiv). After stirring for 20 min at 0° C., the reaction mixture was cooled to −78° C., and (E)-tert-butyl 3-(4-chloro-3-(trifluoromethyl)phenyl)acrylate (5.98 g, 19.5 mmol, 1.00 equiv) in THF (20 mL) was added dropwise over 30 min. After stirring for 30 min, 10% AcOH (aq) (100 mL) and Et$_2$O (200 mL) were added and then the reaction mixture was warmed to 23° C. The phases were separated and the organic phase was washed with 10% AcOH (aq) (2×200 mL). The organic phase was dried (MgSO$_4$) and the filtrate was concentrated in vacuo, after which the residue was purified by silica gel column chromatography eluting with hexanes/EtOAc to afford 7.0 g of the title compound (69% yield).

NMR Spectroscopy: $^1$H NMR (300 MHz, CDCl$_3$): δ 7.71 (s, 1H), 7.61-7.18 (m, 12H), 4.44 (t, J=7.2 Hz, 1H), 3.92 (q, J=7.5 Hz, 1H), 3.62 (s, 2H), 2.46 (d, J=7.2 Hz, 2H), 1.35-1.26 (m, 3H), 1.26 (s, 9H). $^{19}$F NMR (282 MHz, CDCl$_3$): δ −62.5 (s, 3F).

(S)-tert-butyl 3-amino-3-(3-(trifluoromethyl)phenyl) propanoate

To (S)-tert-butyl 3-(benzyl((R)-1-phenylethyl)amino)-3-(4-chloro-3-(trifluoromethyl)phenyl)propanoate (7.00 g, 13.5 mmol, 1.00 equiv) in MeOH—AcOH (120 mL-12 mL) at 23° C. and under an atmosphere of air, was added 20% Pd(OH)$_2$/C (1.90 g, 2.70 mmol, 20.0 mol %) and H$_2$ gas was introduced into the reaction mixture with a balloon. After stirring for 7 hr at 60° C., the reaction mixture was filtered through a pad of celite. The filtrate was concentrated, after which EtOAc (100 mL) and K$_2$CO$_3$ (aq) (100 mL) were added to the residue. The phases were separated and the aqueous phase was extracted with EtOAc (2×100 mL). The combined organic phases were washed with brine (100 mL), dried (MgSO$_4$), and filtered. The filtrate was concentrated in vacuo and the residue was purified by silica gel column chromatography eluting with hexanes/EtOAc to afford 3.0 g of the title compound (77% yield) NMR Spectroscopy: $^1$H NMR (300 MHz, CDCl$_3$): δ 7.64 (s, 1H), 7.60-7.40 (m, 3H), 4.45 (t, J=7.2 Hz, 1H), 2.59 (d, J=7.2 Hz, 2H), 1.40 (s, 9H). $^{19}$F NMR (282 MHz, CDCl$_3$): δ −62.5 (s, 3F).

Enhancement of Enantiomeric Purity of (S)-tert-butyl 3-amino-3-(3-(trifluoromethyl)phenyl)-propanoate by recrystallization To (S)-tert-butyl 3-amino-3-(3-(trifluoromethyl)phenyl) propanoate (3.00 g, 10.4 mmol, 1.00 equiv) in i-PrOAc (50 mL) at 23° C. and under an atmosphere of air, was added a hot solution of (1R)-(−)-10-camphorsulfonic acid (2.41 g, 10.4 mmol, 1.00 equiv) in i-PrOAc (50 mL). The solution was cooled and kept at 23° C. for 3 hr. The crystals were collected by filtration and dried under vacuum. The obtained crystals were suspended in CH$_2$Cl$_2$ (30 mL) and K$_2$CO$_3$ (aq) (30 mL) was then added. The phases were separated and the aqueous phase was extracted with CH$_2$Cl$_2$ (2×30 mL). The combined organic phases were washed with brine (20 mL), dried (MgSO$_4$), and filtered. The filtrate was concentrated in vacuo to afford 2.22 g of the title compound (74% yield).

(S)-tert-butyl 3-((2,2-dimethoxyethyl)amino)-3-(3-(trifluoromethyl)phenyl)propanoate To (S)-tert-butyl 3-amino-3-(3-(trifluoromethyl)phenyl) propanoate (2.22 g, 7.67 mmol, 1.00 equiv) at 23° C. and under an atmosphere of air, in THF (30 mL) was added 2,2-dimethoxyacetaldehyde (60% wt in H$_2$O, 1.16 mL, 7.67 mmol, 1.00 equiv) and sodium triacetoxyborohydride (4.88 g, 23.0 mmol, 3.00 equiv). After stirring for 30 min at 23° C., HCl (aq) (50 mL) was added and the reaction mixture was neutralized by the addition of K$_2$CO$_3$. The phases were separated and the aqueous phase was extracted with EtOAc (3×50 mL). The combined organic phases were washed with brine (100 mL), dried (MgSO$_4$), and filtered. The filtrate was concentrated in vacuo and the residue was purified by silica gel column chromatography eluting with hexanes/EtOAc to afford 2.00 g of the title compound (69% yield).

NMR Spectroscopy: $^1$H NMR (300 MHz, CDCl$_3$): δ 8.18 (d, J=7.2 Hz, 1H), 7.76 (s, 1H), 7.70-7.59 (m, 2H), 4.92-4.85 (m, 1H), 4.71-4.58 (m, 1H), 3.59 (dd, J=16.8, 7.2 Hz, 1H), 3.51 (s, 3H), 3.40 (s, 3H), 3.13 (dd, J=16.8, 7.2 Hz, 1H), 2.91 (dd, J=12.3, 4.5 Hz, 1H), 2.75 (dd, J=12.3, 4.5 Hz, 1H), 1.36 (s, 9H). $^{19}$F NMR (282 MHz, CDCl$_3$): δ −62.8 (s, 3F).

(S)-tert-butyl 3-(2-oxo-3-(3-(5,6,7,8-tetrahydro-1,8-naphthyridin-2-yl)propyl)-2,3-dihydro-1H-imidazol-1-yl)-3-(3-(trifluoromethyl)phenyl)propanoate To triphosgene (629 mg, 2.12 mmol, 0.400 equiv) in THF (10 mL) at 0° C. and under an atmosphere of N$_2$, was added a solution of (S)-tert-butyl 3-((2,2-dimethoxyethyl)amino)-3-(3-(trifluoromethyl)phenyl)propanoate (2.00 g, 5.30 mmol, 1.00 equiv) and triethylamine (2.22 mL, 15.9 mmol, 3.00 equiv) in THF (10 mL). After stirring for 30 min at 23° C., 3-(5,6,7,8-tetrahydro-1,8-naphthyridin-2-yl)propan-1-amine (1.52 g, 7.95 mmol, 1.50 equiv) was added. After stirring for 3.0 hr at 40° C., EtOAc (30 mL) and H$_2$O (20 mL) were added to the reaction mixture. The phases were separated and the aqueous phase was extracted with EtOAc (3×20 mL). The combined organic phases were washed with brine (20 mL), dried (MgSO$_4$), and filtered. The filtrate was concentrated in vacuo to afford a crude urea, which was used in the next step without further purification.

To the above-obtained crude urea in THF (5.5 mL) under an atmosphere of air, was added 2M H$_2$SO$_4$ (aq) (5.5 mL). After stirring for 12 hr at 23° C., K$_2$CO$_3$ (aq) (10 mL) was added. The phases were separated and the aqueous phase was extracted with EtOAc (3×15 mL). The combined organic phases were washed with brine (20 mL), dried (MgSO$_4$), and filtered. The filtrate was concentrated in vacuo and the residue was purified by silica gel column chromatography eluting with CH$_2$Cl$_2$/MeOH to afford 1.60 g of the title compound (57% yield).

NMR Spectroscopy: $^1$H NMR (400 MHz, CDCl$_3$): δ 7.58-7.40 (m, 4H), 7.04 (d, J=7.2 Hz, 1H), 6.32 (d, J=7.2 Hz, 1H), 6.27 (d, J=2.7 Hz, 1H), 6.21 (d, J=2.7 Hz, 1H), 5.72 (dd, J=7.8, 7.8 Hz, 1H), 4.82 (br s, 1H), 3.64-3.58 (m, 2H), 3.40-3.36 (m, 2H), 3.14-2.98 (m, 2H), 2.70-2.50 (m, 4H), 2.03-1.80 (m, 4H), 1.38 (s, 9H). $^{19}$F NMR (375 MHz, CDCl$_3$): δ −62.6 (s, 3F).

(S)-tert-butyl 3-(2-oxo-3-(3-(5,6,7,8-tetrahydro-1,8-naphthyridin-2-yl)propyl) imidazolidin-1-yl)-3-(3-(trifluoromethyl)phenyl)propanoate To (S)-tert-butyl 3-(2-oxo-3-(3-(5,6,7,8-tetrahydro-1,8-naphthyridin-2-yl)propyl)-2,3-dihydro-1H-imidazol-1-yl)-3-(3-(trifluoromethyl)phenyl)propanoate (1.60 g, 3.02 mmol, 1.00 equiv) in MeOH (15 mL) at 23° C. and under an atmosphere of air, was added 20% Pd(OH)$_2$/C (424 mg, 0.604 mmol, 0.200 equiv) and H$_2$ gas was introduced into the reaction mixture with a balloon. After stirring for 18 hr at 60° C., the reaction mixture was concentrated in vacuo to afford 1.6 g of the title compound (99% yield).

NMR Spectroscopy: $^1$H NMR (400 MHz, CDCl$_3$): δ 7.59-7.40 (m, 4H), 7.06 (d, J=7.2 Hz, 1H), 6.35 (d, J=7.2 Hz, 1H), 5.52 (dd, J=7.8, 7.8 Hz, 1H), 3.40-3.18 (m, 8H), 3.00-2.82 (m, 2H), 2.70-2.50 (m, 4H), 1.96-1.80 (m, 4H), 1.34 (s, 9H). $^{19}$F NMR (375 MHz, CDCl$_3$): δ −62.5 (s, 3F).

(S)-3-(2-oxo-3-(3-(5,6,7,8-tetrahydro-1,8-naphthyridin-2-yl)propyl)imidazolidin-1-yl)-3-(3-(trifluoromethyl)phenyl)propanoic acid To (S)-tert-butyl 3-(2-oxo-3-(3-(5,6,7,8-tetrahydro-1,8-naphthyridin-2-yl)propyl)imidazolidin-1-yl)-3-(3-(trifluoromethyl)phenyl)propanoate (1.60 g, 3.00 mmol, 1.00 equiv) in CH$_2$Cl$_2$ (3 mL) at 23° C. and under an atmosphere of air, was added TFA (3 mL). After stirring for 1 hr at 23° C., the reaction mixture was concentrated in vacuo, after which EtOAc (10 mL) and K$_2$CO$_3$ (aq) (10 mL) were added to the residue. The phases were separated and the aqueous phase was extracted with EtOAc (3×10 mL). The combined organic phases were washed with brine (10 mL), dried (MgSO$_4$), and filtered. The filtrate was concentrated in vacuo and the residue was purified by silica gel column chromatography eluting with CH$_2$Cl$_2$/MeOH to afford 400 mg of the title compound (28% yield).

NMR Spectroscopy: $^1$H NMR (400 MHz, CDCl$_3$): δ 7.60 (s, 1H), 7.58-7.40 (m, 3H), 7.22 (d, J=7.2 Hz, 1H), 6.27 (d, J=7.2 Hz, 1H), 5.68 (d, J=9.9 Hz, 1H), 3.78-3.38 (m, 5H), 3.20-3.08 (m, 1H), 3.00-2.60 (m, 8H), 1.99-1.75 (m, 4H). $^{19}$F NMR (375 MHz, CDCl$_3$): δ −62.5 (s, 3F).

Example 12. Testing of the Compounds of Present Invention in Cell Adhesion Assays The ability of compounds to block adhesion of three primary cell cultures: human dermal microvascular endothelial (HMVEC), rat lung microvascular endothelial (RLMVEC), and rabbit aortic endothelial (RAEC) cells, to vitronectin coated plates was determined using the following procedure. This test demonstrates inhibition of the interaction of αv integrin on the cell surface with the ligand, vitronectin.

Adhesion Plates Preparation.

96-well plates were coated with vitronectin in PBS, pH7.4 by incubating 50 μL of the solution (10 μg/ml) for 1.5 h at room temperature or overnight at 4° C. The plates then were blocked with 1% BSA in PBS (30 min at room temperature) and washed with PBS.

Cell Culturing and Loading.

HMVEC cells (passages p 9-14) (from Lonza, Allendale, N.J.) RLMVEC cells (p 4-14) (from Vec Technology, Rensselaer, N.Y.) and RAEC cells (p 4-14) (from CellBiologics, Chicago, Ill.) were used for the compound testing. Cells were grown in T175 tissue culture flasks and dislodged by gentle 3 min treatment with Accutase (Life Technologies). After washing, the cells in suspension in RPMI-1640 (Life Technologies) were loaded with calcein-AM (5 μM) (Life Technologies) for 30 min at 37° C. and re-suspended into RPMI w/o phenol red medium containing 10% FBS.

Adhesion Assay.

The cell suspension was aliquoted into the wells at a density of $1.0 \times 10^5$ cells/well (RLMVEC) and $5.0 \times 10^4$ (HMVEC, and RAEC). The test compounds were added at the same time with the cells. The plates were incubated for 1.5 h at 37° C. The cells that did not adhere during this incubation were removed by gentle washing. The wash was performed by 2 cycles of aspiration of the supernatant and addition of 100 μL of the pre-warmed fresh DPBS (Life Technologies). A fluorescence of the remaining cells is measured using multimode plate reader (Victor 2V, PerkinElmer) at an excitation/emission wavelengths of 485/535 nm. The compounds were tested starting with maximal concentration of 1 μM with half-log dilution schedule. $IC_{50}$ values were calculated with Prism 5 (GraphPad, CA) by fixing the bottom of the curves to a value of blank for empty wells fluorescence.

Example 13. Testing of the Compounds of Present Invention in $\alpha_V$ Integrin Binding Assays All $\alpha_V$ Integrins are known to bind to proteins with a RGD motif. Two RGD ligands were used in this study: Vitronectin (VN) as a ligand for $\alpha_V\beta_3$ and $\alpha_V\beta_5$ (Wayner et al., *J. Cell Biol.*, 113 (4), 919-929, 1991), and LAP TGF-β1 (LAP1) as a ligand for $\alpha_V\beta_6$ and $\alpha_V\beta_8$ (Rognoni et al., *Nat. Med.*, 20(4): 350-359, 2014). CWHM12 was used as a positive control for $\alpha_V\beta_6$ and $\alpha_V\beta_8$ (Henderson et al., *Nat. Med.* 19(12), 10.1038/nm.3282 2013), and Cilengitide as a positive control for $\alpha_V\beta_3$ and $\alpha_V\beta_5$ (Kumar et al., *J. Pharmacol. Exp. Ther.*, 283, 843-853, 1997).

The integrin coupled Dyna beads were allowed to interact with respective ligands. The integrin-ligand complex was detected with either Primary/Secondary Antibody conjugated with Fluorescein Isothiocyanate (FITC). For $\alpha_V\beta3$ and $\alpha_V\beta5$, Vitronectin was used as a ligand and a primary antibody conjugated with FITC (Anti-VN-FITC Ab) was used to detect the interaction. For $\alpha_V\beta6$ and $\alpha_V\beta8$, LAP-TGF (31 was used as ligand and a primary antibody against LAP1 (Anti-LAP1 Ab) and a secondary antibody conjugated with FITC were used to detect the $\alpha_V\beta6/\alpha_V\beta8$-LAP-TGF (31 complex. Fluorescence was measured by Flow Cytometry analysis.

Activation of Beads.

5 mg of Dyna beads were weighed in a low protein binding microfuge (Eppendorf) tube (1.5 mL volume). The beads were re-suspended in 1 mL of Sodium Phosphate Buffer and vortexed at high speed for 30 seconds. The tube was then placed in a tube roller and tilt rotated for 10 min. After tilt rotation, the tube was placed on the Magna Spin and the beads were allowed to settle. The supernatant was discarded and the beads were washed three times. The beads were then re-suspended in 100 μL of Sodium Phosphate Buffer and 20 μL of washed beads were distributed into 5 low protein binding Eppendorf tubes (1 mg of beads in each tube). The beads were used for coupling integrins.

Coupling of Dyna Beads with Integrins.

20 μL of (1 mg) of beads were mixed with 20 μL of integrins (20 μg) and 20 μL of 3 M Ammonium Sulfate solution (final concentration of ammonium sulfate was 1M) to achieve a Bead: Protein ratio of 5 mg:100 μg. The solution was mixed gently and placed in a tube roller and incubated at 37° C. for 16 hours.

Quantification of Coupling.

The tubes were taken out and subjected to a quick spin. The tubes were placed in the magna spin and the supernatant (60 μL) was collected (Supernatant). The beads were re-suspended in 60 μL of PBS and vortexed for 10 seconds. The beads were allowed to settle in the magna spin and the supernatant was collected as Wash 1 (W1) to remove the loosely bound proteins. The beads were washed three more times with 30 of PBS each time, and the supernatant was collected as W2, W3 and W4. The beads were finally re-suspended in 25 μL of PBS and stored at 4° C. until use. The amount of protein bound to beads was quantified by measuring the sum of protein left in the Supernatant, W1, W2, W3 and W4 through the Micro BCA method.

Micro BCA Method.

BSA was used as standard. The concentration range of BSA was 1 μg/mL to 20 μg/mL in PBS. 10 μL of the Supernatant was mixed with 40 μL of PBS in a 96 well plate, and then with 100 μL of Micro BCA reagent. The plate was shaked at 37° C. for 3 hours. After incubation, the OD at 562 nm was measured to determine the amount of protein in the Supernatant. The amounts of protein in W1, W2, W3 and W4 were determined with the same procedure.

The amounts of protein in the Supernatant, W1, W2, W3 and W4 were added and subtracted from the initial amount of the protein that was used for beads coupling, which provided the amount of protein bound to the beads and molarity of the protein was calculated.

αVβ6/αVβ8—LAP-TGF β1 Interaction:

αVβ6/αVβ8 coupled beads were treated with the ligand LAP TGF-β1 (LAP1) at room temperature for 3 hours. The complex (Integrin+Ligand) was then treated with primary Ab (Anti-LAP1 Ab) overnight at 4° C. The whole complex (Integrin+Ligand+Primary Ab) was treated with Secondary Ab conjugated with FITC and incubated for 2 hours. The complex was analyzed by either plate reader or Flow Cytometer.

10 μL of αVβ6/αVβ8 coupled beads were taken for the experiment. The concentration of integrins was 10 nM. 10 μL of LAP1 was taken (10 nM for aVβ6 and 20 nM for aVβ8). Reaction between integrin coupled beads and LAP1 was considered as the full reaction, and reaction without LAP1 or a compound of the disclosure was considered as the blank reaction. The samples were incubated in low protein binding tubes at room temperature for 3 hours. The tubes were briefly spun and placed in a Magna spin. The supernatant was removed. The beads were washed with assay buffer twice to remove excess LAP1 and then re-suspended in 150 of assay buffer containing 1:200 anti-LAP1 Ab (primary Ab). The tubes were placed in a tube roller and incubated at 4° C. overnight. After a brief spin, the tubes were then placed in a Magna spin and the supernatant was removed. The beads were washed with assay buffer twice to remove excess primary Ab and then re-suspended in 150 µL of assay buffer containing 1:500 secondary Ab conjugated with FITC. The tubes were incubated at room temperature for 2 hours in a tube roller. After a brief spin, the tubes were placed in a Magna spin and the supernatant was removed. The beads were washed with assay buffer twice followed by PBS. The beads were then re-suspended in 300 µL of PBS and analyzed by a Flow Cytometer (BD FACSCalibur, Software—BDcell Quest Pro Version 6).

αVβ3/αVβ5—LAP-TGF β1 Interaction:

αVβ3/αVβ5 coupled beads were treated with the ligand at room temperature for 3 hours. The complex (Integrin+Ligand) was then treated with Anti-Vitronectin Ab conjugated with FITC overnight at 4° C. The complex was analyzed by either plate reader or Flow Cytometer.

10 µL of αVβ3/αVβ5 coupled beads were taken for the experiment. The concentration of integrins was 10 nM. 10 µL of vitronectin was taken. The concentration was 10 nM. Reaction between integrin coupled beads and vitronectin was considered as the full reaction, and reaction without vitronectin or a compound of the disclosure was considered as the blank reaction. The samples were incubated in low protein binding tubes at room temperature for 3 hours. The tubes were briefly spun and placed in a Magna spin. The supernatant was then removed. The beads were washed with assay buffer twice to remove excess vitronectin and then re-suspended in 150 µL of assay buffer containing 1:500 Anti-vitronectin Ab conjugated with FITC. The tubes were placed in a tube roller and incubated at 4° C. overnight. After a brief spin, the tubes were placed in a Magna spin and the supernatant was discarded. The beads were washed with assay buffer twice followed by PBS. The beads were then re-suspended in 300 of PBS and analyzed by a Flow Cytometer (BD FACSCalibur, Software—BD Cell Quest Pro Version 6).

Quantification:

The samples were acquired using a BD FACSCalibur system and analyzed with BD Cell quest pro Version 6. Median values for the following were extracted from the software: Full reaction (Integrin+Ligand) with or without compound, Control: Without Ligand (LAP1/Vitronectin), and Vehicle Control: Full reaction with DMSO. Blank=Test Median value−control Median value. Percentage Inhibition=100−[(Blanked Test Median/Blanked vehicle Median)*100]. Percentage of binding was calculated with respect to full reaction. The value was subtracted from 100 to get percentage of inhibition. All the plotted values were average of triplicates. SD was determined for each experiment. $IC_{50}$ was determined with Graph Pad Prism.

Inhibition of Integrin-Ligand Interaction by Reference Inhibitors:

The optimized protocol was validated by employing reference compounds such as Cilengitide (αVβ3/αVβ5-VN interaction) and CWHM12 (αVβ6/αVβ8-LAP1 interaction). The full reaction (Integrin-Ligand Interaction) was optimized as above. Integrin coupled beads were taken for the experiment.

2 µL of 10 nM/20 nM of Ligand was taken and mixed with 8 µL of the compound (i.e., Cilengitide or CWHM12, each diluted from a 10 mM stock). Reaction, with or without DMSO (0.08%), between Integrin and Ligand in the absence of the compound was considered as the full reaction. Reaction with DMSO (0.08%) in the absence of compound and Ligand was considered as the blank reaction.

The samples incubated in low protein binding tubes at room temperature for 3 hours. The tubes were placed in a Magna spin and the supernant was discarded. The beads were washed with assay buffer twice to remove the excess Ligand and then re-suspended in 150 µL of assay buffer containing the primary antibody (1:500 of Anti-VN-FITC or 1:200 of Anti-LAP1 Ab). The tubes were placed in a tube roller and incubated at 4° C. overnight. After a brief spin, the tubes were placed in a Magna spin, and the supernatant was discarded. In the case of αVβ3/αVβ5-VN interaction, the beads were washed with assay buffer twice and finally washed with PBS. The beads were then re-suspended in 300 µL of PBS and analyzed by a Flow Cytometer. In the case of αVβ6/αVβ8-LAP1 interaction, the beads were washed with assay buffer twice and treated with 150 µL of Secondary Antibody (1:500) for two hours at room temperature, washed twice with assay buffer and PBS, and finally re-suspended in 300 µL of PBS and analyzed by a Flow Cytometer.

Table 3 shows the integrin inhibition activity of compounds of the invention.

TABLE 3

Integrin Inhibition Assay Results

| Cmpd # | αvβ6 $IC_{50}$ (nM) | αvβ8 $IC_{50}$ (nM) | αvβ8/αvβ6 | αvβ3 $IC_{50}$ (nM) |
|---|---|---|---|---|
| A30s | 9.57 | 17.56 | 1.83 | |
| A1 | 8.30 | 13.20 | 1.59 | |
| A4 | 5.69 | 21.35 | 3.75 | 1.4 |
| A2 | 11.64 | 78.14 | 6.71 | 9.0 |
| A3 | 18.16 | 79.31 | 4.37 | 0.57 |
| A5 | 9.97 | 63.90 | 6.41 | 65.7 |
| A6 | 8.25 | 24.02 | 2.91 | 190.1 |
| A7 | 11.63 | 80.63 | 6.93 | |
| A23 | 14.80 | 150.70 | 10.18 | 4.3 |
| A24 | 17.51 | 35.37 | 2.02 | |
| A28 | 16.88 | 34.39 | 2.04 | |
| A15s | 9.28 | 5.92 | 0.64 | |
| A21 | 7.64 | 88.16 | 11.54 | |
| A21-1 | NA | NA | NA | |
| A21-2 | 4.60 | 50.30 | 10.93 | |

Example 14. Anti-Angiogenic Activity Using Chick Chorioallantoic Membrane (CAM) Assay CAM surfaces were grafted with gelatin sponges impregnated with the concentrations of test compounds and 50 ng VEGF dissolved in PBS. Untreated CAM received only VEGF and PBS. Error bars represent SEM, N=5, P values for the treated groups were calculated by comparing with the untreated group (*$p<0.05$, $p<0.01$, *$p<0.001$).

Test Substance Preparation:

Test samples and standards were dissolved in PBS and sterilized by passing through a syringe filter (0.22 µm). hVEGF (SIGMA) 50 ng/µl was prepared in sterile PBS.

Grafting:

Gelatin sponge (Abogel) was cut in approximately 2 mm$^3$ pieces and loaded with required test substance or PBS and VEGF. The graft was placed on the CAM.

Eggs:

Fertile hen eggs were procured from a hatchery and were cleaned and decontaminated using alcohol. 1 ml of albumin was removed using a syringe and incubated for 8 days. Grafts were placed on developing CAMs and further incubated to day 12. On day 12, CAMs were fixed with 4% formaldehyde in PBS, dissected and imaged.

Imaging:

Fixed CAMs were imaged under constant illumination and magnification under a stereomicroscope fitted with a digital camera (CANON).

Image Analysis:

Images were analyzed on MS PowerPoint keeping the image size constant. A ring was drawn around the graft and the size was kept constant. Blood vessels crossing the ring were counted for each test group.

Statistical Analysis:

Data were analyzed on MS Excel 2007.

Example 15. Distribution in Plasma, Aqueous Humor, Vitreous Humor, and Retina after Topical Ocular Administration in Dutch Belted Rabbits The plasma concentrations and ocular distribution (aqueous humor, vitreous humor, and retina) of Compounds A1, A2, and A3 were determined following topical ocular administration in Dutch Belted rabbits. The test compounds were administered in each eye at a volume of 50 μL/eye at a concentration of 1.0-2.5 mg/mL (Compound A2, 1.0 mg/mL; Compounds A1 and A3 at 2.5 mg/mL). Plasma and different ocular tissue samples were collected at pre-determined time points (1.0 and 8.0 hours for compound A1; 0.5 and 8 hours for Compounds A2 and A3). Aqueous humor, vitreous humor, and retina were collected from each eye at each time point post-dose. Also, weights were recorded. Plasma and ocular sample concentrations of the compounds were determined by LC-MS/MS.

Animal Dosing:

The exposure of Compounds A1, A2, and A3 was evaluated in Dutch Belted rabbits. The study was not blinded. Each compound was dosed as n=3/time point for a total of nine rabbits. Rabbits were housed one per cage. Animals were not fasted, and food and water were supplied ad libitum.

Animals were anesthetized following the 13IA5 IACUC protocol for the dosing. Each rabbit received a bolus dose of test formulation via topical ocular administration into both eyes at time zero on the day of dosing. Plasma and ocular samples were collected at pre-determined time points. Animals for the 30-minute and 1-hour time points were anesthetized for the entire duration of the study. The animals for the 8-hour time point were recovered after dosing and then euthanized for sampling purposes.

At each time point, approximately 0.5 mL of blood was collected and placed into chilled Na-heparin tubes containing citric acid. Blood samples were centrifuged at a speed of 3,000 g for 5 minutes to obtain plasma as quickly as possible. Samples were stored frozen at −80° C. until analysis. Animals were euthanized per the 13IA5 IACUC protocol and both eyes were enucleated immediately. Following enucleation, each eye was rinsed with PBS. Ocular samples from both eyes of each animal were collected and weights were recorded. All the samples were frozen immediately on dry ice, and stored at −60° C. to −80° C. for analysis.

Analysis of Plasma and Ocular Samples:

An LC-MS/MS method was developed for the determination of the concentration of Compounds A1, A2, and A3 in rabbit plasma and ocular samples. A pre-study standard curve was analyzed to determine the specificity, range, and lower limit of quantitation of the method.

The following examples of ophthalmic formulations are given by way of illustration:

Example 16. Evaluation of the Safety and Efficacy of Topically Applied Test Compounds in the Laser-Induced Choroidal Neovascularization (CNV) Model in Dutch Belted Rabbits Healthy male animals weighing between 1.5 kg and 2.0 kg were used in these studies. Animals were weighed prior to dosing and at euthanasia, and more often if needed. Baseline fundus photography and fluorescein angiography was performed on each animal prior to CNV induction.

Animals were anesthetized with an intramuscular injection of ketamine hydrochloride (20 mg/kg) and xylazine (2 mg/kg) for CNV induction, fundus photography, fluorescein angiography, and intravitreal (IVT) injections. Rabbits were maintained on isoflurane (approximately 1 to 3%) in oxygen (approximately 1 to 2 L/min) as necessary. One drop of topical proparacaine hydrochloride anesthetic (0.5%) was placed in each eye before procedures. Additional topical ocular anesthesia was utilized during the procedure if needed.

CNV was induced by laser photocoagulation treatment. An external diode laser was applied to the retina using a laser contact lens and a slit lamp biomicroscope. On Day 1, both eyes of each animal underwent laser photocoagulation treatment using the following laser settings:

Number of Spots: 12-15 spots per eye
Power Range: 50-200 mW
Spot Size: 20-100 μm
Time: 0.05-0.1 seconds Following laser treatment, 50 μL of a 25-μg/mL VEGF solution (1.25 μg dose) was intravitreally injected into each eye. Daily gross ocular exams were performed throughout the study period.

Clinical ophthalmic exams (slit-lamp biomicroscopy and indirect ophthalmoscopy), fundus photography, and fluorescein angiography were performed at baseline and then weekly for up to 6 weeks post-induction. Exams were scored using the McDonald-Shadduck Score System. Optical Coherence Tomography OCT imaging was performed weekly for diagnostic imaging during the exams.

On the last day of the study, blood sampling was performed just prior to administration of the AM dose and at 2 hours post dosing. Blood samples were centrifuged at a speed of 3,000 g for 5 minutes to obtain plasma as quickly as possible. Samples were stored frozen at −80° C. until analysis. At the conclusion of the study, animals were euthanized per the 13C232Q3 IACUC protocol and both eyes enucleated immediately. Following enucleation, each eye was rinsed with phosphate-buffered saline. Ocular samples (aqueous humor, vitreous humor retina and choroid) from both eyes of each animal were collected and weights were recorded. All the samples were frozen immediately on dry ice, and stored at −60° C. to −80° C. for analysis.

Example 17. Diagnosing Fibrosis

Fibrosis is a pathophysiological process in response to tissue injury due to viral or bacterial infection, inflammation, autoimmune disease, trauma, drug toxicity, and so on. During this process, an excess amount of collagen is expressed and fibrous material forms in the extracellular space of the affected tissue. Thus, fibrosis can be generally recognized based on the distinct morphology of fibrous tissue in a biopsy of the organ in which fibrosis is suspected.

Other means for detecting the presence of fibrosis or developing fibrosis include computerized axial tomography (CAT or CT) scan, ultrasound, magnetic resonance imaging (MRI), and monitoring the level of one or more serum markers known to be indicative of fibrosis (e.g., various types of collagens).

The precise manner of diagnosing fibrosis also varies depending on the organ where the fibrotic process takes place. For instance, biopsies are generally effective for diagnosing fibrosis of most organs, whereas endoscopy involving a fiber optic instrument (e.g., a sigmoidoscope or a colonoscope) can be a less traumatic alternative to detect fibrosis of certain organs such as the intestine.

Biopsy for Detecting Fibrosis

Standard procedures have been established for obtaining biopsy from a given organ or tissue. For example, a specimen can be obtained during exploratory surgery, but is more often obtained by inserting a biopsy needle through the skin and into the organ or tissue. Before this procedure is performed, the person receives a local anesthetic. Ultrasound or CT scans may be used to locate the abnormal area from which the specimen is to be taken.

Upon obtaining an organ or tissue biopsy, the sample is examined and given a score to indicate the presence and level of fibrosis in the sample. Most frequently used scoring systems include the METAVIR or modified HAI (ISHAK) scoring system. The Knodell scoring system can also be used for analyzing the liver sample. The criteria used in scoring are well established and known to those of skilled in the art. For example, the METAVIR system provides five gradings: F0 indicates the absence of fibrosis; F1 indicates portal fibrosis without septa; F2 indicates portal fibrosis and some septa; F3 indicates septal fibrosis without cirrhosis; and F4 indicates the presence of cirrhosis.

Biopsy is not only useful for the diagnosis of fibrosis, it can also aid physicians to assess the effectiveness of fibrosis treatment/prevention methods of the present invention by monitoring the progression of fibrosis using methodologies known in the art. See, e.g., Poynard et al., Lancet 349:825, 1997.

Fibrosis Markers

There are numerous known serum markers whose level can be indicative of the presence and/or severity of fibrosis. Blood tests measuring markers, e.g., hyaluronic acid, laminin, undulin (type IV collagen) pro-peptides from types I, II, and IV collagens, lysyl oxidase, prolyl hydroxylase, lysyl hydroxylase, PIIINP, PICP, collagen VI, tenascin, collagen XIV, laminin P1, TIMP-1, MMP-2, $\alpha 2$ macroglobulin, haptoglobin, gamma glutamyl transpeptidase, $\gamma$ globulin, total bilirubin, apolipoprotein A1, etc., according to the established methods can thus be useful for both the diagnosis of fibrosis and monitoring of fibrosis progression. Additional markers, such as nucleic acid markers, can be used for detecting and/or monitoring fibrosis. For instance, Wnt-4 has recently been indicated in laboratory experiments as a gene that plays an important role in renal fibrosis, where its mRNA expression is significantly increased in the fibrotic tissue in the kidney (See, e.g., Surendran et al., *Pediatr.* 140:119-24, 2002). The quantitative detection of gene expression of this type of markers can be useful in the diagnosis and monitoring of fibrosis Example 18. Bleomycin Induced Mouse Pulmonary Fibrosis Model Ninety-five male C57BL/6 mice were randomly and prospectively assigned to one group of fifteen animals and eight groups of ten animals each. On day 0 and at least one hour prior to bleomycin induction, animals were administered the first dose of vehicle or test-article (i.e., a compound of the present disclosure). At least one hour following dosing, all mice were anesthetized with isoflurane and placed on their backs lying on a table at approximately 60°. A small diameter cannula was inserted into the trachea, and saline or bleomycin was slowly infused into the lungs in a volume of 40 µL.

Group 1 served as an untreated control group and received saline only (no bleomycin) on day 0. Groups 2-9 received 2.25 U/kg of bleomycin on day 0. The animals were then released into a recovery cage and allowed to wake up. From day 0 through day 21, treatments were administered once or twice daily via oral gavage (PO). Vehicle treated animals (Group 2) received 0.4% methylcellulose. Remaining animals received either Pirfenidone at 100 mg/kg (Group 3), Compound A15s at 100 mg/kg (Group 4), 30 mg/kg (Group 5) or 10 mg/kg (Group 6), or Compound A21 at 100 mg/kg (Group 7), 30 mg/kg (Group 8) or 10 mg/kg (Group 9).

All animals were weighed and evaluated daily for respiratory distress (defined as an increase in respiratory rate and/or obvious respiratory effort). Animals with severe respiratory distress, or animals that lost greater than 30% of their total starting body weight, were euthanized within 2 hours of observation.

On Day 21, prior to sacrifice, mice were anesthetized with IP injection of ketamine/xylazine (100 mg/kg, 10 mg/kg). Once the animal was determined to be non-responsive a shallow 2 cm vertical incision was made starting from 1 cm below the chin. The trachea was isolated and a transverse cut was made between tracheal rings approximately half-way through the trachea. A tracheotomy was performed by the insertion of an 18 gauge polyethylene cannula through the incision secured with surgical suture to the trachea. Following cannulation, the adapter end of the cannula was attached to the flexiVent mechanical ventilator. The animal was ventilated at 10 ml/kg tidal volume ($V_T$), 150 breaths per minute and 3 cm $H_2O$ positive end expiratory pressure (PEEP). Following a 2-minute acclimation period, lung volume was standardized with 1, 6-second deep inflation to a pressure of 30 cm $H_2O$ followed by 2 pressure-volume measurements up to 40 ml/kg. Each animal then underwent a measure of total respiratory impedance by applying a 3-second pseudorandom frequency oscillation to the airway opening at 3, 6, 9 and 12 cm $H_2O$ PEEP. If at any time during this procedure the animal became responsive as demonstrated by a response to stimuli or spontaneous breathing efforts the animal received a supplemental dose of 50 mg/kg ketamine.

Compounds A15s and A21 reversed bleomycin induced lung stiffness at all doses tested, as compared to the vehicle control group. The mid- and high-dose groups of Compound A15s produced a significant reversal of bleomycin induced lung stiffness, and both groups were superior to the positive control pirfenidone given at 100 mg/kg BID. The mid-dose group of Compound A15s was indistinguishable from the saline treated animal group (i.e., animals not treated with bleomycin). The mid- and high-dose groups of Compound A21 also produced similar, if not better, reversal of bleomycin induced lung stiffness, as compared to the positive control pirfenidone given at 100 mg/kg BID.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

The invention claimed is:

1. A compound selected from the group consisting of:

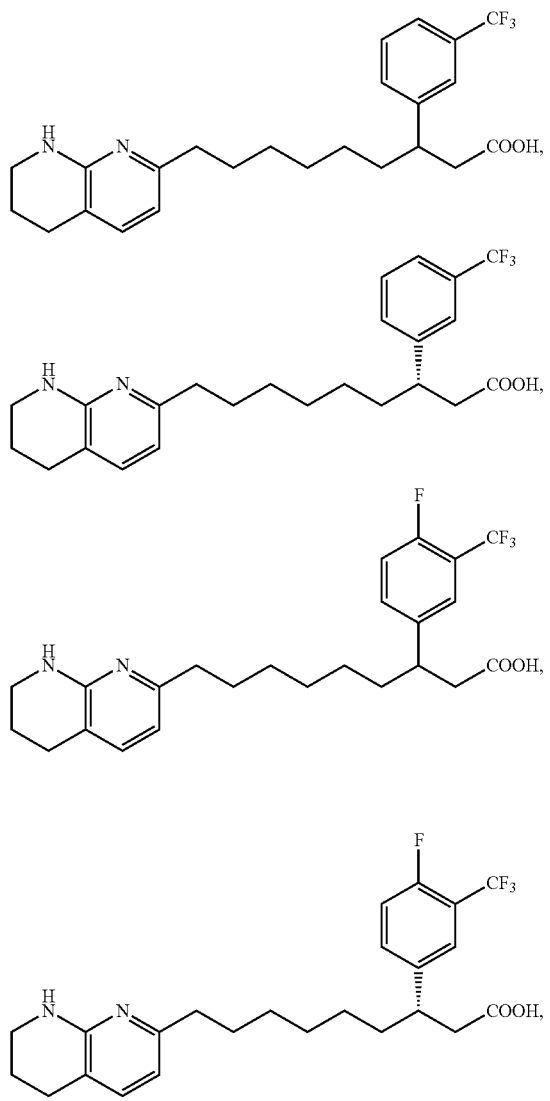

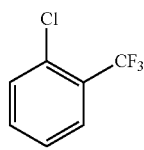
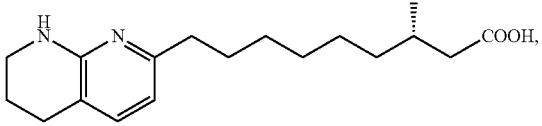
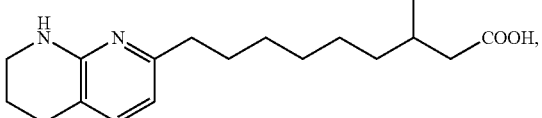
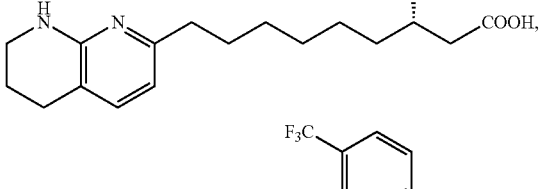
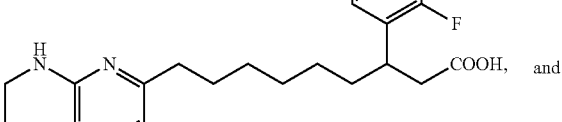
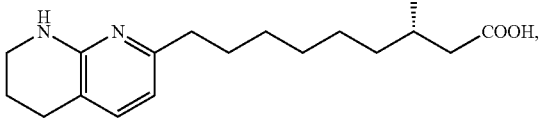

or a pharmaceutically acceptable salt or solvate thereof.

2. A compound selected from the following or a pharmaceutically acceptable salt thereof:

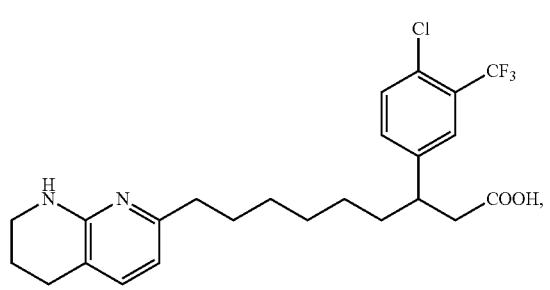

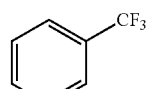
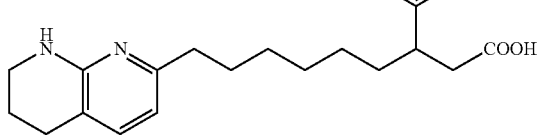

-continued

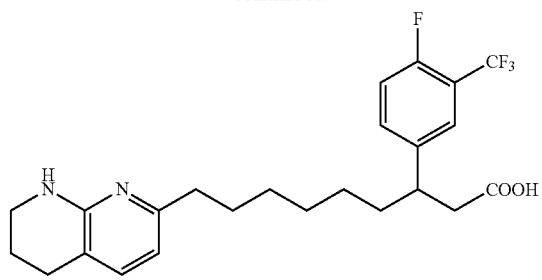

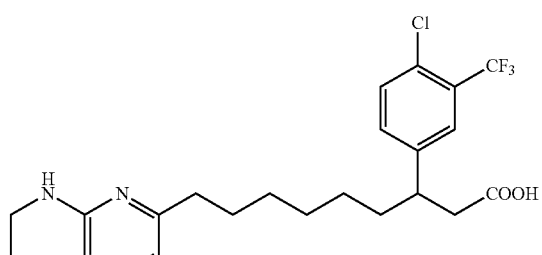

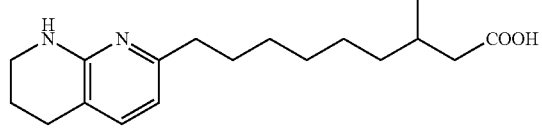

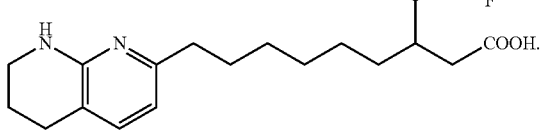

3. The compound of claim 2, wherein the compound is

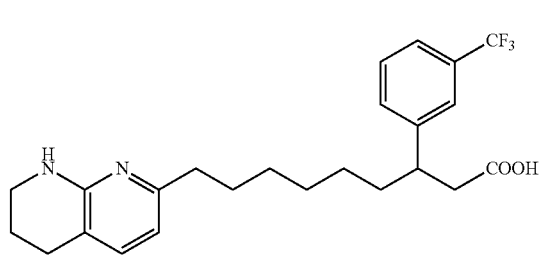 [SMILES: O=C(O)CC(CCCCCCc1ccc2c(n1)NCCC2)c1cccc(C(F)(F)F)c1]

or a pharmaceutically acceptable salt thereof.

4. The compound of claim 2, wherein the compound is

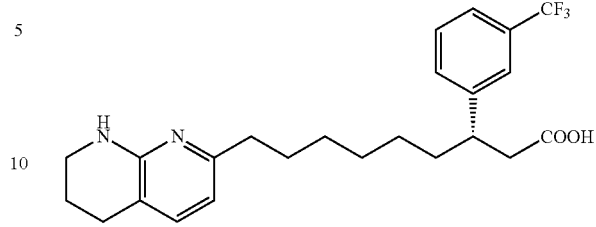

or a pharmaceutically acceptable salt thereof.

5. The compound of claim 2, wherein the compound is

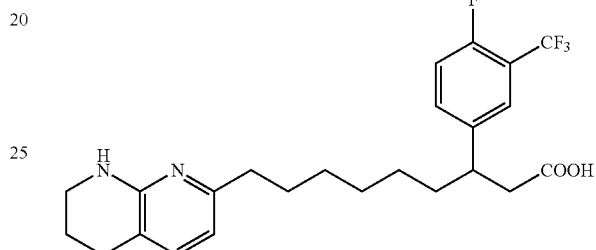

or a pharmaceutically acceptable salt thereof.

6. The compound of claim 2, wherein the compound is

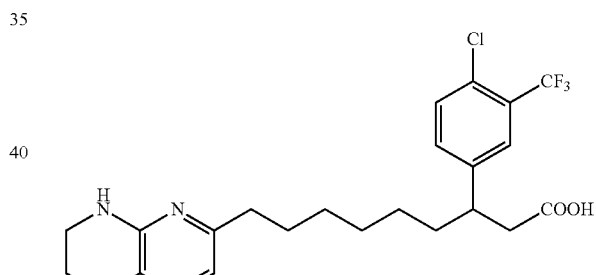

or a pharmaceutically acceptable salt thereof.

7. The compound of claim 2, wherein the compound is

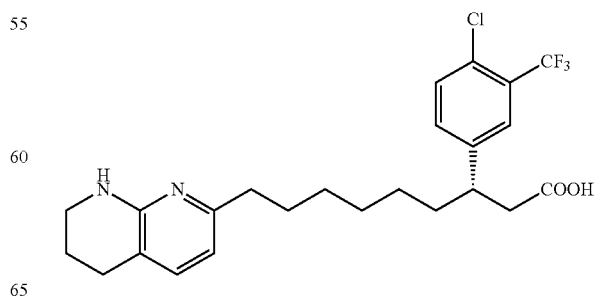

or a pharmaceutically acceptable salt thereof.

8. The compound of claim 2, wherein the compound is

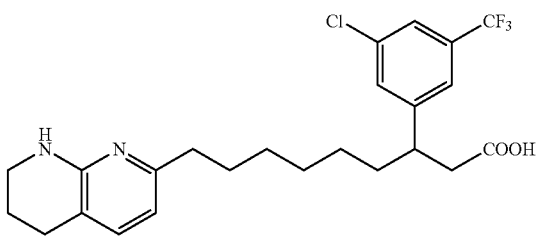

or a pharmaceutically acceptable salt thereof.

9. The compound of claim 2, wherein the compound is

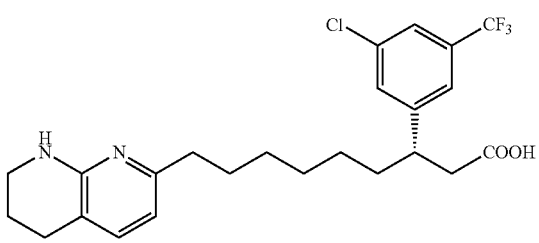 [SMILES: O=C(O)CC(CCCCCCc1ccc2c(n1)NCCC2)c1cc(Cl)cc(C(F)(F)F)c1]

or a pharmaceutically acceptable salt thereof.

10. The compound of claim 2, wherein the compound is

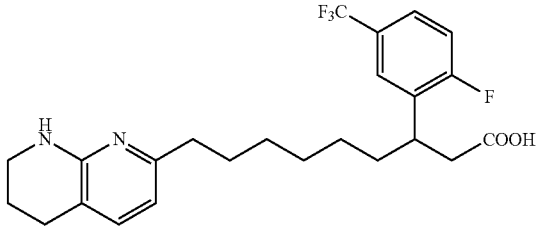 [SMILES: O=C(O)CC(CCCCCCc1ccc2c(n1)NCCC2)c1cc(C(F)(F)F)ccc1F]

or a pharmaceutically acceptable salt thereof.

11. The compound of claim 2, wherein the compound is

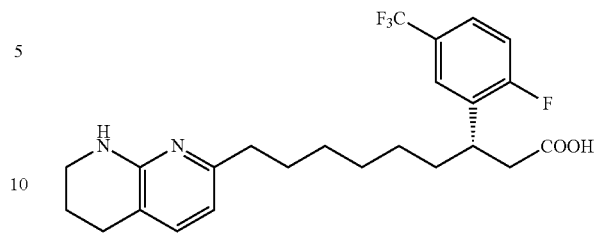

or a pharmaceutically acceptable salt thereof.

12. A pharmaceutical composition comprising a compound of claim 2 and a pharmaceutically acceptable carrier or excipient.

13. A pharmaceutical composition comprising a compound of claim 3 and a pharmaceutically acceptable carrier or excipient.

14. A pharmaceutical composition comprising a compound of claim 6 and a pharmaceutically acceptable carrier or excipient.

15. A pharmaceutical composition comprising a compound of claim 8 and a pharmaceutically acceptable carrier or excipient.

16. A pharmaceutical composition comprising a compound of claim 10 and a pharmaceutically acceptable carrier or excipient.

17. A method of treating fibrosis in a subject, comprising administering to a subject in need thereof a therapeutically effective amount of a compound of claim 2 to treat the fibrosis.

18. A method of treating fibrosis in a subject, comprising administering to a subject in need thereof a therapeutically effective amount of a compound of claim 3 to treat the fibrosis.

19. A method of treating a disease or condition selected from macular degeneration, age-related macular degeneration, diabetic retinopathy, diabetic macular edema, retinopathy of prematurity, or macular edema following retinal vein occlusion in a subject, comprising administering to a subject in need thereof a therapeutically effective amount of a compound of claim 2 to treat the disease or condition.

20. A method of treating a disease or condition selected from macular degeneration, age-related macular degeneration, diabetic retinopathy, diabetic macular edema, retinopathy of prematurity, or macular edema following retinal vein occlusion in a subject, comprising administering to a subject in need thereof a therapeutically effective amount of a compound of claim 3 to treat the disease or condition.

* * * * *